(12) United States Patent
Lau et al.

(10) Patent No.: US 9,963,496 B2
(45) Date of Patent: May 8, 2018

(54) STABLE GLUCAGON ANALOGUES AND USE FOR TREATMENT OF HYPOGLYCAEMIA

(71) Applicant: Novo Nordisk A/S, Bagsvaerd (DK)

(72) Inventors: Jesper F. Lau, Farum (DK); Thomas Kruse, Herlev (DK); Peter Kresten Nielsen, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days. days.

(21) Appl. No.: 15/117,993

(22) PCT Filed: Feb. 18, 2015

(86) PCT No.: PCT/EP2015/053394
§ 371 (c)(1),
(2) Date: Aug. 10, 2016

(87) PCT Pub. No.: WO2015/124612
PCT Pub. Date: Aug. 27, 2015

(65) Prior Publication Data
US 2017/0008943 A1  Jan. 12, 2017

(30) Foreign Application Priority Data
Feb. 18, 2014  (EP) .................................... 14155497

(51) Int. Cl.
*A61K 38/00*  (2006.01)
*C07K 14/605*  (2006.01)
*C07K 19/00*  (2006.01)

(52) U.S. Cl.
CPC ............ *C07K 14/605* (2013.01); *C07K 19/00* (2013.01); *A61K 38/00* (2013.01)

(58) Field of Classification Search
None
See application file for complete search history.

(56) References Cited

U.S. PATENT DOCUMENTS

| | | |
|---|---|---|
| 7,314,859 B2 | 1/2008 | Green et al. |
| 8,450,270 B2 | 5/2013 | Dimarchi et al. |
| 8,541,368 B2 | 9/2013 | Lau et al. |
| 9,486,505 B2 | 11/2016 | Lau et al. |
| 2009/0137456 A1 | 5/2009 | Dimarchi et al. |
| 2010/0190699 A1 | 7/2010 | Dimarchi et al. |
| 2011/0166062 A1 | 7/2011 | Dimarchi et al. |
| 2013/0035285 A1 | 2/2013 | Lau et al. |

FOREIGN PATENT DOCUMENTS

| | | |
|---|---|---|
| EP | 0926159 | 6/1999 |
| JP | 2008-533105 | 8/2008 |
| JP | 2008-533106 A | 8/2008 |
| WO | 96/29342 | 9/1996 |
| WO | 98/19698 A1 | 5/1998 |
| WO | 2005/012347 A2 | 2/2005 |
| WO | 2007056362 A2 | 5/2007 |
| WO | 2008086086 A2 | 7/2008 |
| WO | 2008101017 A2 | 8/2008 |
| WO | 2008152403 A1 | 12/2008 |
| WO | 2009/030771 A1 | 3/2009 |
| WO | 2009/058662 A2 | 5/2009 |
| WO | 2009/155258 A2 | 12/2009 |
| WO | 2009155257 A1 | 12/2009 |
| WO | 2010/011439 A2 | 1/2010 |
| WO | 2010096052 A1 | 8/2010 |
| WO | 2010/148089 A1 | 12/2010 |
| WO | 2011006497 A1 | 1/2011 |
| WO | 2011/117415 A1 | 9/2011 |
| WO | 2011/117416 A1 | 9/2011 |
| WO | 2012130866 A1 | 10/2012 |
| WO | 2012167744 A1 | 12/2012 |
| WO | 2013041678 A1 | 3/2013 |
| WO | 2013/167454 A1 | 11/2013 |
| WO | 2013192129 A1 | 12/2013 |

OTHER PUBLICATIONS

Wermuth, et al "Glossary of Terms used in Medicinal Chemistry," Pure and Appl. Chem., vol. 70, No. 5, pp. 1129-1143, (1998).*
Beaven G H et al. Formation and Structure of Gels and Fibrils from Glucagon, "European Journal Biochemistry", Jun. 1969, vol. 11, pp. 37-42.
Chabenne J R et al. Optimization of the Native Glucagon Sequence for Medicinal Purposes, "Journal of Diabetes Science and Technology", Nov. 2010, vol. 4, No. 6, pp. 1322-1331.
Harris G et al. Glucagon administration underevaluated and undertaught "Practical Diabetes Int", Jan./Feb. 2001, vol. 18, No. 1, pp. 22-25.
Lefebvre P J, Glucagon I, II, III, Handbook of experiemental Pharmacology, vol. 66/I, vol. 66/II, and vol. 123, P.J Springer-verlag, Year 1983 71 pgs.
Mulhauser I et al. Incidence and Management of Severe Hypoglycemia in 434 Adults with Insulin dependent Diabetes Mellitus, "Diabetes Care", May 1985, vol. 8, No. 3, pp. 268-273.
Persson E et al. Assignment of molecular properties of a superactive coagulation; factor VIIa variant to individual amino acid changes, "Eur. J. Biochem", Year 2002, vol. 269, pp. 5950-5955.
Persson E et al. Rational design of coagulation factor VIIa variants with substantially increased intrinsic activity, "PNAS", Year 2001, vol. 98, No. 24, pp. 13583-13588.
Petersen M T et al. Amino acid neighbours and detailed conformational analysis of cysteines in proteins, "Protein Engineering", Year 1999, vol. 12, pp. 535-548.
Suchanek M et al. Photo-leucine and photo-methionine allow identification of protein-protein interactions in living cells, "Nature Methods", Year 2005, vol. 2, pp. 261-267.
Xie J et al. An expanding genetic code, "Methods", year 2005, vol. 36, pp. 227-238.
Beaven G. H. et al., European Journal of Biochemistry, "Formation and Structure of Gels and Fibrils From Glucagon", 1969, vol. 11, pp. 37-42.
Schade DS et al., Acta Diabetologica, "Modulation of the Catabolic Activity of Glucagon by Endogenous Insulin Secretion in Obese Man", 1977, vol. 14, No. 1-2, pp. 62-72.

* cited by examiner

*Primary Examiner* — Thomas S Heard
(74) *Attorney, Agent, or Firm* — Leon Y. Lum

(57) ABSTRACT

The invention relates to derivatives of glucagon analogs comprising the substitutions Imp1 and His3, a substituent having three to ten negatively charged moieties covalently attached to a side chain of a lysine as well as intermediates and compositions thereof and their use in medicine.

26 Claims, 1 Drawing Sheet

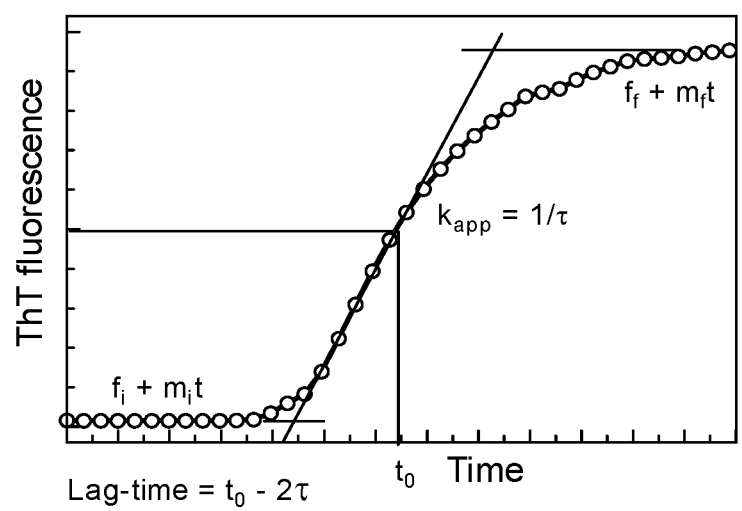

STABLE GLUCAGON ANALOGUES AND USE FOR TREATMENT OF HYPOGLYCAEMIA

CROSS-REFERENCE TO RELATED APPLICATIONS

This application is a 35 U.S.C. § 371 National Stage application of International Application PCT/EP2015/053394 (WO 2015/124612), filed Feb. 18, 2015, which claims priority to European Patent Application 14155497.2, filed Feb. 18, 2014; the contents of which are incorporated herein by reference.

The present invention is directed to novel derivatives of glucagon analogues and their use in medicine, such as treatment of hypoglycaemia.

SEQUENCE LISTING

The instant application contains a Sequence Listing which has been submitted in ASCII format via EFS-Web and is hereby incorporated by reference in its entirety. Said ASCII copy, created on Jul. 25, 2016, is named Seq_List130077US01.txt and is 12,157 bytes in size.

BACKGROUND

Glucagon has long been known to be effective in treating hypoglycaemia caused by insulin action. The hyperglycaemic effects of glucagon is a result of stimulating the breakdown of hepatic glycogen into glucose (glycogenolysis) and increasing the glucose production derived from amino acid precursors (gluconeogenesis) resulting in increased glucose output from the liver.

The commercially available glucagon for treatment of severe hypoglycaemia is supplied as a kit consisting of a vial with freeze dried glucagon and a disposable syringe prefilled with water (Eli Lilly and Novo Nordisk). Before use, glucagon has to be reconstituted by adding water from the syringe to the vial with glucagon. The vial must then be gently shaken until all glucagon has dissolved and the resulting solution should be drawn back into the syringe and injected to the person in need. In a severe hypoglycaemic event the patient is unconscious or semi-unconscious and is therefore dependent on an assisting person to administer glucagon.

The reconstitution step is considered troublesome by relatives to diabetics, and it delays or may even prevent treatment of severe hypoglycaemic events.

The main obstacle for a prefilled ready-to-use device is the inherent instability of glucagon. Solutions of glucagon form gels or fibrils within a few hours after dissolution. In addition, glucagon has an inherently low solubility in the pH range of 3-9. It contains several labile amino acids and the chemical stability of a glucagon composition is very poor, mainly due to deamidation, isomerization, oxidation and hydrolytic cleavage.

In order to enable the development of a prefilled ready-to-use device, a new non-fibrillating glucagon analogue needs to be developed. In addition, improved chemical stability of glucagon is required to enable a solution to be kept at room temperature for an extended period of time. Furthermore, such a glucagon analogue should have a fast onset of action (such as hyperglycaemic effect) after subcutaneous (SC) or intramuscular (IM) administration.

BRIEF DESCRIPTION OF THE DRAWINGS

FIG. 1: ThT fibrillation assay in which F is the ThT fluorescence at time t.

SUMMARY

In one embodiment the invention relates to a derivative of a glucagon analogue comprising formula I (SEQ ID NO: 21):

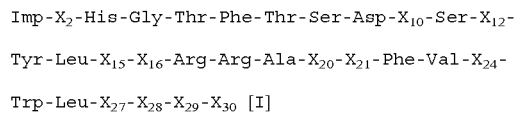

wherein
$X_2$ is Ser or Aib;
$X_{10}$ is Tyr, Leu, Ile or Val;
$X_{12}$ is Lys or Arg;
$X_{15}$ is Asp or Glu;
$X_{16}$ is Ser, Ala, Leu, Thr, Aib, Ile, Val or Lys;
$X_{20}$ is Gln, Glu, Aib or Lys;
$X_{21}$ is Asp, Glu or Lys;
$X_{24}$ is Gln, Ala, Glu, Aib or Lys;
$X_{27}$ is Met, Leu or Val;
$X_{28}$ is Asn, Ser, Thr, Gln, Ala, Gly, Glu or Lys;
$X_{29}$ is Thr, Gly, Ser, Gln, Ala, Glu or Lys; and
$X_{30}$ is absent or is Lys;
and wherein said derivative comprises a substituent covalently attached to the nitrogen atom of the side chain of a lysine in position $X_{12}$, $X_{16}$, $X_{20}$, $X_{21}$, $X_{24}$, $X_{28}$, $X_{29}$ or $X_{30}$ of formula I, wherein said substituent has the formula II:

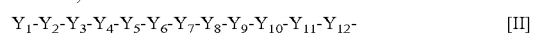

wherein $Y_1$ is hydrogen or represents a $C_{2-6}$ acyl group or a succinoyl moiety, and wherein $Y_2$, $Y_3$, $Y_4$, $Y_5$, $Y_6$, $Y_7$, $Y_8$, $Y_9$, $Y_{10}$, $Y_{11}$ or $Y_{12}$ is individually absent or individually represents an amino acid residue selected from the group consisting of a Ser residue, an Ala residue, a Gly residue, formula i, formula ii, formula iii, formula iv and formula v:

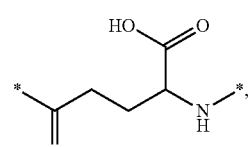

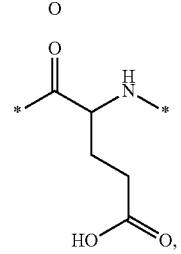

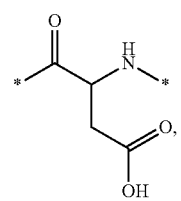

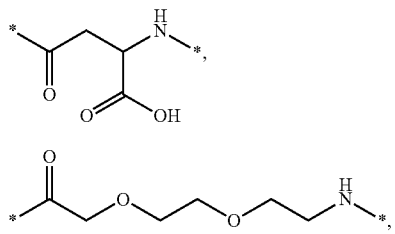

wherein formula i, ii, iii, and iv individually has the stereochemistry L or D, and provided that said substituent has three to ten negatively charged moieties, or a pharmaceutically acceptable salt, amide, or ester of said derivative.

In one embodiment the invention relates to an intermediate product in the form of a glucagon analogue which comprises the following modifications as compared to glucagon (SEQ ID NO: 1):
(i) [Imp1, Aib2, His3, Leu16, Lys24, Leu27, Ser28]-Glucagon;
(ii) [Imp1, Aib2, His3, Glu15, Lys24, Leu27, Ser28]-Glucagon;
(iii) [Imp1, Aib2, His3, Leu10, Glu15, Lys24, Leu27, Ser28]-Glucagon;
(iv) [Imp1, Aib2, His3, Glu15, Ala24, Leu27, Lys28]-Glucagon;
(v) [Imp1, His3, Glu15, Lys24, Leu27, Ser28]-Glucagon;
(vi) [Imp1, His3, Glu15, Glu21, Lys24, Leu27, Ser28]-Glucagon;
(vii) [Imp1, Aib2, His3, Glu15, Glu21, Lys24, Leu27, Ser28]-Glucagon;
(viii) [Imp1, His3, Leu16, Glu21, Lys24, Leu27, Ser28]-Glucagon;
(ix) [Imp1, His3, Leu16, Lys24, Leu27, Ser28]-Glucagon;
(x) [Imp1, Aib2, His3, Val16, Lys24, Leu27, Ser28]-Glucagon;
(xi) [Imp1, His3, Glu15, Lys16, Glu21, Leu27, Ser28]-Glucagon;
(xii) [Imp1, His3, Glu15, Lys20, Glu21, Leu27, Ser28]-Glucagon;
(xiii) [Imp1, His3, Glu15, Lys21, Leu27, Ser28]-Glucagon;
(xiv) [Imp1, His3, Glu15, Glu21, Leu27, Lys28]-Glucagon;
(xv) [Imp1, His3, Glu15, Glu21, Leu27, Ser28, Lys29]-Glucagon;
(xvi) [Imp1, His3, Glu15, Glu21, Leu27, Ser28, Lys30]-Glucagon;
or a pharmaceutically acceptable salt, amide, or ester thereof.

In one embodiment the invention relates to a composition comprising the derivative of the invention and one or more pharmaceutically acceptable excipients.

In one embodiment the invention relates to a derivative as defined of the invention for use in medicine.

DESCRIPTION

In one embodiment the present invention relates to novel fast-acting derivatives of glucagon analogues, i.e. derivatives of glucagon analogues which may be used in treatment of e.g. hypoglycaemia where a rapid onset of biological action after administration is required.

The inventors surprisingly found that the derivatives of the invention have improved chemical and physical stability in solution while maintaining good potency on the human glucagon receptor and a fast onset of hyperglycaemic effect.

Accordingly, the derivatives of the invention enable a liquid composition with long term storage stability of said liquid composition comprising said derivatives.

The derivatives comprise the amino acid substitutions imidazopropionyl (Imp) in position 1 and histidine in position 3. The derivatives further comprise a substituent having 3-10 negatively charged moieties, wherein said substituent is covalently attached to the side chain of an amino acid, such as the nitrogen atom of the side chain of a lysine.

In one embodiment the invention relates to a derivative of a glucagon analogue comprising formula I (SEQ ID NO: 21):

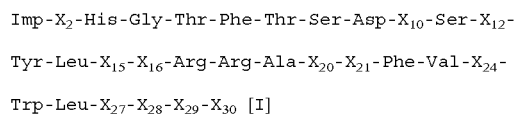

wherein
$X_2$ is Ser or Aib;
$X_{10}$ is Tyr, Leu, Ile or Val;
$X_{12}$ is Lys or Arg;
$X_{15}$ is Asp or Glu;
$X_{16}$ is Ser, Ala, Leu, Thr, Aib, Ile, Val or Lys;
$X_{20}$ is Gln, Glu, Aib or Lys;
$X_{21}$ is Asp, Glu or Lys;
$X_{24}$ is Gln, Ala, Glu, Aib or Lys;
$X_{27}$ is Met, Leu or Val;
$X_{28}$ is Asn, Ser, Thr, Gln, Ala, Gly, Glu or Lys;
$X_{29}$ is Thr, Gly, Ser, Gln, Ala, Glu or Lys; and
$X_{30}$ is absent or is Lys;
and wherein said derivative comprises a substituent covalently attached to the nitrogen atom of the side chain of a lysine in position $X_{12}$, $X_{16}$, $X_{20}$, $X_{21}$, $X_{24}$, $X_{28}$, $X_{29}$ or $X_{30}$ of formula I,
wherein said substituent has the formula II:

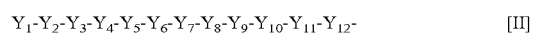

wherein $Y_1$ is hydrogen or represents a $C_{2-6}$ acyl group or a succinoyl moiety, and
wherein $Y_2$, $Y_3$, $Y_4$, $Y_5$, $Y_6$, $Y_7$, $Y_8$, $Y_9$, $Y_{10}$, $Y_{11}$ or $Y_{12}$ is individually absent or individually represents an amino acid residue selected from the group consisting of a Ser residue, an Ala residue, a Gly residue, formula i, formula ii, formula iii, formula iv and formula v:

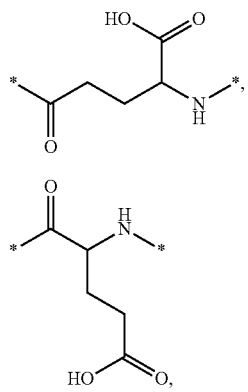

-continued

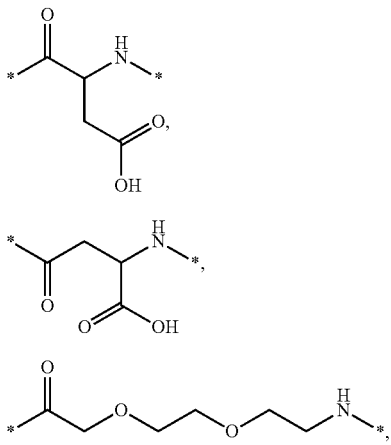

wherein formula i, ii, iii, and iv individually has the stereochemistry L or D, and provided that said substituent has three to ten negatively charged moieties,
or a pharmaceutically acceptable salt, amide, or ester of said derivative.

In one embodiment, the symbol "*" (or alternatively a waved line) when used herein in a drawing of a chemical structure represents the point of attachment to the neighbouring position in the derivative.

Glucagon Peptides and Analogues

The term "glucagon peptide" as used herein refers to human glucagon, the sequence of which is included in the sequence listing as SEQ ID NO: 1, or an analogue thereof (e.g. a glucagon analogue of formula I). The peptide having the sequence of SEQ ID NO: 1 may also be referred to as "glucagon" herein. In one embodiment as used herein the term "glucagon" refers to His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1).

The derivative of the invention comprises a glucagon analogue. The term "glucagon analogue" as used herein refers to a peptide, or a compound, which is a variant of glucagon (SEQ ID NO: 1). In one embodiment the glucagon analogue comprises formula I:

```
Imp-X2-His-Gly-Thr-Phe-Thr-Ser-Asp-X10-Ser-X12-

Tyr-Leu-X15-X16-Arg-Arg-Ala-X20-X21-Phe-Val-X24-

Trp-Leu-X27-X28-X29-X30  [I]
``` wherein
$X_2$ is Ser or Aib;
$X_{10}$ is Tyr, Leu, Ile or Val;
$X_{12}$ is Lys or Arg;
$X_{15}$ is Asp or Glu;
$X_{16}$ is Ser, Ala, Leu, Thr, Aib, Ile, Val or Lys;
$X_{20}$ is Gln, Glu, Aib or Lys;
$X_{21}$ is Asp, Glu or Lys;
$X_{24}$ is Gln, Ala, Glu, Aib or Lys;
$X_{27}$ is Met, Leu or Val;
$X_{28}$ is Asn, Ser, Thr, Gln, Ala, Gly, Glu or Lys;
$X_{29}$ is Thr, Gly, Ser, Gln, Ala, Glu or Lys; and
$X_{30}$ is absent or is Lys.

Glucagon analogues of the derivatives of the invention may be described by reference to i) the number of the amino acid residue in human glucagon (SEQ ID NO: 1) which corresponds to the amino acid residue which is modified (i.e. the corresponding position in glucagon (SEQ ID NO: 1)), and to ii) the actual modification. The following are non-limiting examples of suitable analogue nomenclature.

In other words, the glucagon analogue is a glucagon peptide which a number of modifications of amino acid residues when compared to human glucagon (SEQ ID NO: 1). These modifications may represent, independently, one or more amino acid substitutions, additions, and/or deletions. For example, "[Imp1, His3, Glu15, Lys24, Leu27, Ser28]-Glucagon" designates glucagon (SEQ ID NO: 1), wherein the amino acid in position 1 has been substituted with Imp, the amino acid in position 3 has been substituted with His, the amino acid in position 15 has been substituted with Glu, the amino acid in position 24 has been substituted with Lys, the amino acid in position 27 has been substituted with Leu, and the amino acid in position 28 has been substituted with Ser.

Analogues "comprising" certain specified changes may comprise further changes, when compared to SEQ ID NO: 1. In a particular embodiment, the analogue "has" the specified changes.

As is apparent from the above examples, amino acid residues may be identified by their full name, their one-letter code, and/or their three-letter code. These three ways are fully equivalent. In one embodiment peptide analogues and derivatives thereof are drawn using standard one-letter or three-letter codes according to IUPAC-IUB nomenclature.

The expressions "position" or "corresponding position" may be used to characterise the site of change in a glucagon analogue sequence by reference to glucagon (SEQ ID NO: 1). The position, as well as the number of changes, are easily deduced, e.g. by simple handwriting and eyeballing.

The term "peptide", as e.g. used in the context of the glucagon analogues of the derivatives of the invention, refers to a compound which comprises a series of amino acids interconnected by amide (or peptide) bonds. The peptides of the invention comprise at least five constituent amino acids connected by peptide bonds. In particular embodiments, the peptide is a) composed of, or b) consists of i) 29 or ii) 30 amino acids. In a still further particular embodiment the peptide consists of amino acids interconnected by peptide bonds.

Amino acids are molecules containing an amino group and a carboxylic acid group, and, optionally, one or more additional groups, often referred to as a side chain. The term "amino acid" as used herein includes coded amino acids (amongst those the 20 standard amino acids), as well as non-coded amino acids. Coded amino acids are those which are encoded by the genetic code (IUPAC Table 1 section 3AA-1, http://www.chem.qmul.ac.uk/iupac/AminoAcid/AA1n2.html#AA1). Non-coded amino acids are either not found in native peptides and/or proteins, or not produced by standard cellular machinery (e.g., they may have been subject to post-translational modification). Non-limiting examples of non-coded amino acids are Aib (alpha-aminoisobutyric acid), des-amino-histidine (alternative name imidazopropionic acid, abbreviated Imp), as well as the D-isomers of the coded amino acids. Herein, Imp is referred to as an amino acid although it does not contain an amino group.

In what follows, all amino acids of the glucagon peptide for which the optical isomer is not stated is to be understood to mean the L-isomer (unless otherwise specified).

The glucagon peptide may be a glucagon analogue (SEQ ID NO: 1) having a total of up to 15 amino acid differences (also referred to herein as modifications) as compared to glucagon, for example one or more additions, one or more deletions and/or one or more substitutions.

In one embodiment the glucagon analogue consists of formula I. In one embodiment $X_2$ is Ser. In one embodiment $X_{10}$ is Tyr. In one embodiment $X_{12}$ is Lys. In one embodiment $X_{15}$ is Asp. In one embodiment $X_{16}$ is Ser. In one embodiment $X_{20}$ is Gln. In one embodiment $X_{21}$ is Asp. In one embodiment $X_{24}$ is Gln. In one embodiment $X_{27}$ is Met. In one embodiment $X_{28}$ is Asn. In one embodiment $X_{29}$ is Thr. In one embodiment $X_{30}$ is absent. In one embodiment $X_2$ is Aib. In one embodiment $X_{10}$ is Leu. In one embodiment $X_{15}$ is Glu. In one embodiment $X_{16}$ is Leu. In one embodiment $X_{16}$ is Val. In one embodiment $X_{20}$ is Lys. In one embodiment $X_{21}$ is Glu. In one embodiment $X_{24}$ is Lys. In one embodiment $X_{24}$ is Ala. In one embodiment $X_{27}$ is Leu. In one embodiment $X_{28}$ is Ser. In one embodiment $X_{28}$ is Lys. In one embodiment $X_{29}$ is Lys. In one embodiment the glucagon analogue does not comprise a C-terminal amide. In one embodiment the glucagon analogue or derivative comprises no amino acid residues added to the C-terminal of $X_{30}$.

In one embodiment the glucagon analogue comprises 3-15 amino acid residue modifications, such as substitutions or additions, in said glucagon analogue as compared to glucagon (SEQ ID NO: 1). In one embodiment the glucagon analogue comprises 3-15 amino acid residue modifications, such as substitutions or additions, as compared to glucagon (SEQ ID NO: 1). In one embodiment the derivative comprises up to 14, such as up to 13 or up to 12, amino acid residue modifications, such as substitutions or additions, in said glucagon analogue as compared to glucagon (SEQ ID NO: 1). In one embodiment the glucagon analogue comprises up to 11, such as up to 10 or up to 9, amino acid residue modifications, such as substitutions or additions, in said glucagon analogue as compared to glucagon (SEQ ID NO: 1). In one embodiment the glucagon analogue comprises up to 8, such as up to 7 or up to 6, amino acid residue modifications, such as substitutions or additions, in said glucagon analogue as compared to glucagon (SEQ ID NO: 1).

Glucagon Derivatives

The invention relates to derivatives of glucagon analogues. The term "derivative" as used herein in the context of a glucagon peptide, such as a glucagon analogue, means a chemically modified glucagon peptide in which one or more substituents have been covalently attached to the glucagon peptide. The term "substituent" as used herein, means a chemical moiety or group replacing a hydrogen atom. The derivative may comprise one or more modifications selected from amides, carbohydrates, alkyl groups, acyl groups, esters and the like.

In one embodiment the comprises a substituent covalently attached to the nitrogen atom of the side chain of a lysine in position $X_{12}$, $X_{16}$, $X_{20}$, $X_{21}$, $X_{24}$, $X_{28}$, $X_{29}$ or $X_{30}$ of formula I. In one embodiment the substituent has the formula II:

$$Y_1\text{-}Y_2\text{-}Y_3\text{-}Y_4\text{-}Y_5\text{-}Y_6\text{-}Y_7\text{-}Y_8\text{-}Y_9\text{-}Y_{10}\text{-}Y_{11}\text{-}Y_{12}\text{-} \quad [\text{II}]$$

wherein $Y_1$ is hydrogen or represents a $C_{2-6}$ acyl group or a succinoyl moiety, and wherein $Y_2$, $Y_3$, $Y_4$, $Y_5$, $Y_6$, $Y_7$, $Y_8$, $Y_9$, $Y_{10}$, $Y_{11}$ or $Y_{12}$ is individually absent or individually represents an amino acid residue selected from the group consisting of a Ser residue, an Ala residue, a Gly residue, formula i, formula ii, formula iii, formula iv and formula v:

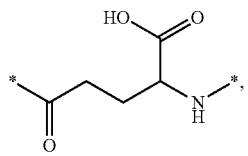
[i]

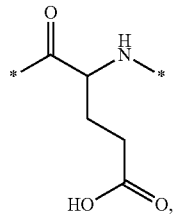
[ii]

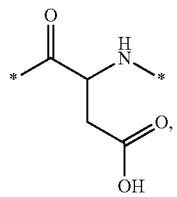
[iii]

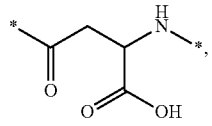
[iv]

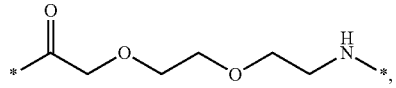
[v]

wherein formula i, ii, iii, and iv individually has the stereochemistry L or D.

In one embodiment $Y_{12}$ is attached to the nitrogen atom of the side chain of a lysine in position $X_{12}$, $X_{16}$, $X_{20}$, $X_{21}$, $X_{24}$, $X_{28}$, $X_{29}$ or $X_{30}$ of the derivative. In one embodiment the substituent is covalently attached to the epsilon-nitrogen atom of the side chain of a lysine. In one embodiment the substituent is attached to a lysine in position $X_{12}$, $X_{16}$ or $X_{20}$. In one embodiment the substituent is attached to a lysine in position $X_{21}$, $X_{24}$ or $X_{28}$. In one embodiment the substituent is attached to a lysine in position $X_{29}$ or $X_{30}$. In one embodiment the substituent is attached to a lysine in position $X_{24}$. The substituent may be covalently attached via $Y_{12}$ to the epsilon-nitrogen atom of the side chain of a lysine. The substituent may be attached via $Y_{12}$ to a lysine in position $X_{12}$, $X_{16}$ or $X_{20}$. The substituent may be attached via $Y_{12}$ to a lysine in position $X_{21}$, $X_{24}$ or $X_{28}$. The substituent may be attached via $Y_{12}$ to a lysine in position $X_{29}$ or $X_{30}$. The substituent may be attached via $Y_{12}$ to a lysine in position $X_{24}$.

In one embodiment $Y_1$ is hydrogen or represents a $C_{2-6}$ acyl group or a succinoyl moiety. The term "$C_{2-6}$ acyl group" as used herein refers to a branched or unbranched acyl group with two to six carbon atoms such as:

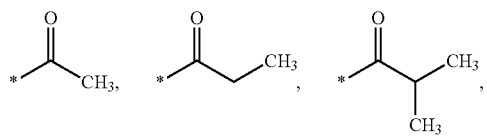

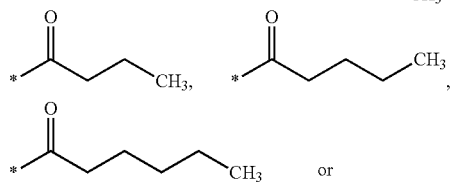

or

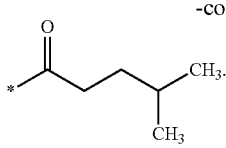

In one embodiment $Y_1$ is an acetyl group. The term "succinoyl" as used herein refers to the following moiety:

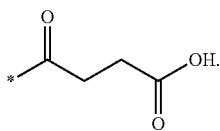 [SMILES: *C(=O)CCC(=O)O]

In one embodiment $Y_1$ is a succinoyl moiety. In one embodiment $Y_1$ is hydrogen.

In one embodiment $Y_2$, $Y_3$, $Y_4$, $Y_5$, $Y_6$, $Y_7$, $Y_8$, $Y_9$, $Y_{10}$, $Y_{11}$ and $Y_{12}$, if present, are connected via amide bonds. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is absent. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is a Ser residue. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is an Ala residue. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is a Gly residue. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is formula i. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is formula ii. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is formula iii. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is formula iv. In one embodiment $Y_2$, $Y_3$, $Y_4$, $Y_5$, $Y_6$, $Y_7$, $Y_8$, $Y_9$, $Y_{10}$, $Y_{11}$ or $Y_{12}$ is formula v. In one embodiment the substituent comprises 3-10, such as 3-5 or 4, residues of formula i.

In one embodiment the substituent has three to ten negatively charged moieties. In one embodiment the substituent has 3, 4, 5, 6, 7, 8, 9 or 10 negatively charged moieties. In one embodiment the substituent has three to ten negatively charged moieties. In one embodiment the substituent has 3-10, such as 3-7 or 3-5, negatively charged moieties. The term "negatively charged moiety" as used herein, means a negatively chargeable chemical moiety, such as, but not limited to an amino acid moiety (e.g. Glu, gamma-Glu, Asp or beta-Asp, a carboxylic acid, sulphonic acid or a tetrazole moiety). In one embodiment the number of "negatively charged moieties" is determined at physiological pH (pH 7.4). In one embodiment the "negatively charged moiety" is a carboxylic acid group.

In one embodiment the substituent is the moiety

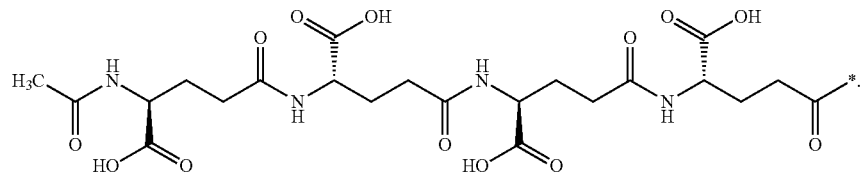

In one embodiment the substituent is the moiety

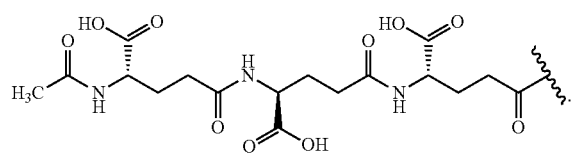 [SMILES: *C(=O)CC[C@H](NC(=O)CC[C@H](NC(=O)CC[C@H](NC(C)=O)C(=O)O)C(=O)O)C(=O)O]

In one embodiment the substituent is the moiety

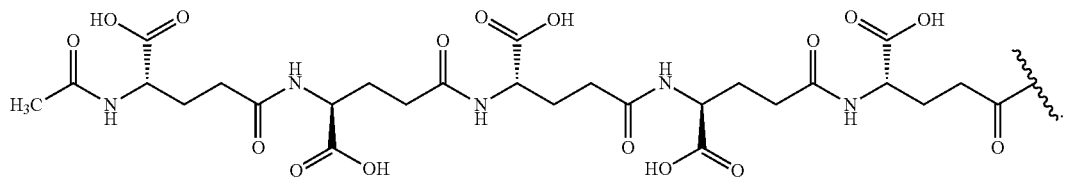 [SMILES: *C(=O)CC[C@H](NC(=O)CC[C@H](NC(=O)CC[C@H](NC(=O)CC[C@H](NC(=O)CC[C@H](NC(C)=O)C(=O)O)C(=O)O)C(=O)O)C(=O)O)C(=O)O]

In one embodiment the substituent is the moiety

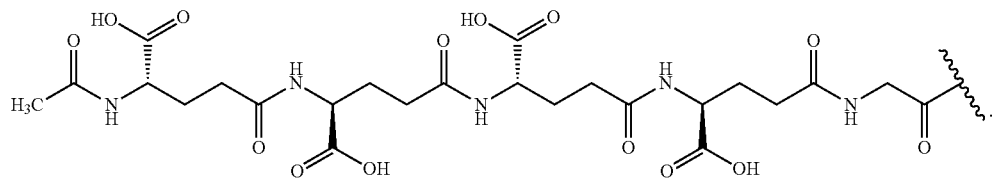 [SMILES: *C(=O)CNC(=O)CC[C@H](NC(=O)CC[C@H](NC(=O)CC[C@H](NC(=O)CC[C@H](NC(C)=O)C(=O)O)C(=O)O)C(=O)O)C(=O)O]

In one embodiment the derivative is $N^{\epsilon 24}$-[(4S)-4-[[(4S)-4-[[(4S)-4-[[(4S)-4-acetamido-4-carboxybutanoyl]amino]-

4-carboxybutanoyl]amino]-4-carboxybutanoyl]amino]-4-carboxybutanoyl]-[Imp1, Aib2, His3, Leu16, Lys24, Leu27, Ser28]-Glucagon Chem. 1 (SEQ ID NO: 2)

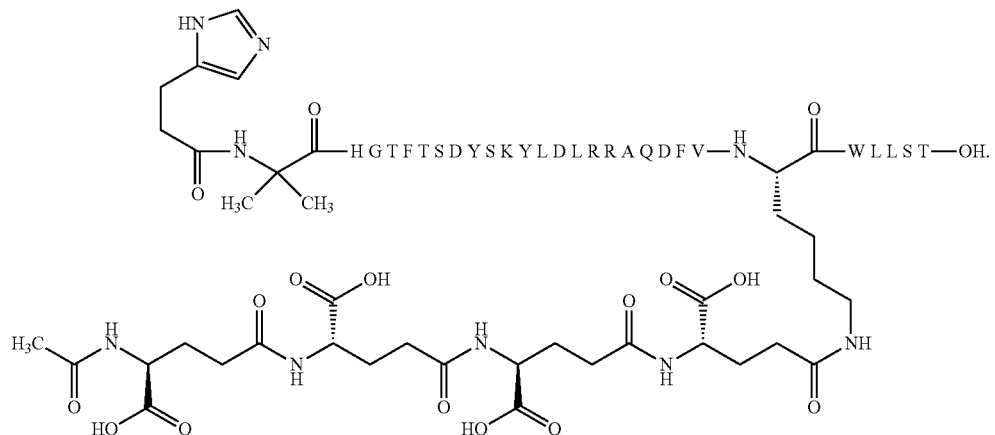

In one embodiment the derivative is $N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Lys24, Leu27, Ser28]-Glucagon Chem. 2 (SEQ ID NO: 3)

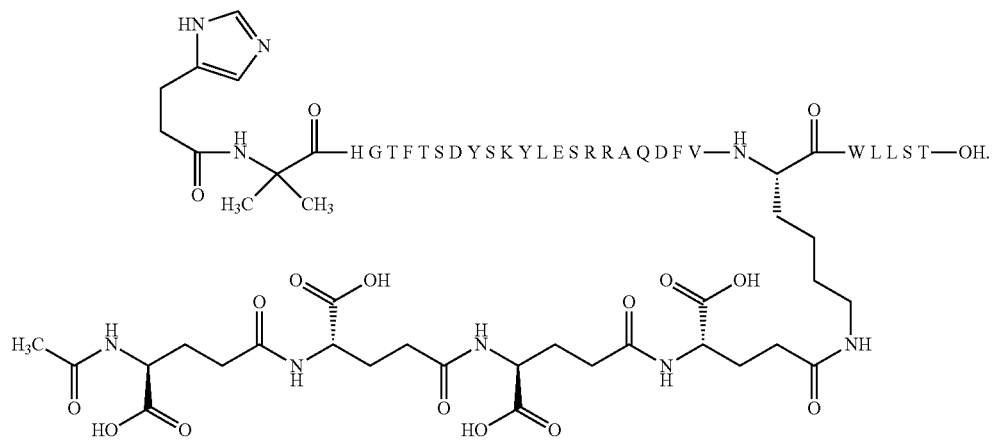

In one embodiment the derivative is $N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Leu10, Glu15, Lys24, Leu27, Ser28]-Glucagon Chem. 3 (SEQ ID NO: 4)

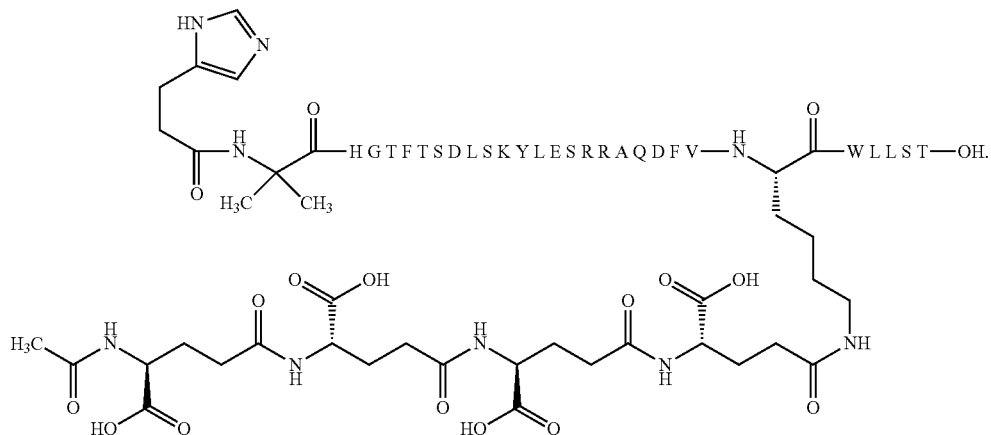

In one embodiment the derivative is N$^{\epsilon 28}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Ala24, Leu27, Lys28]-Glucagon Chem. 4 (SEQ ID NO: 5)

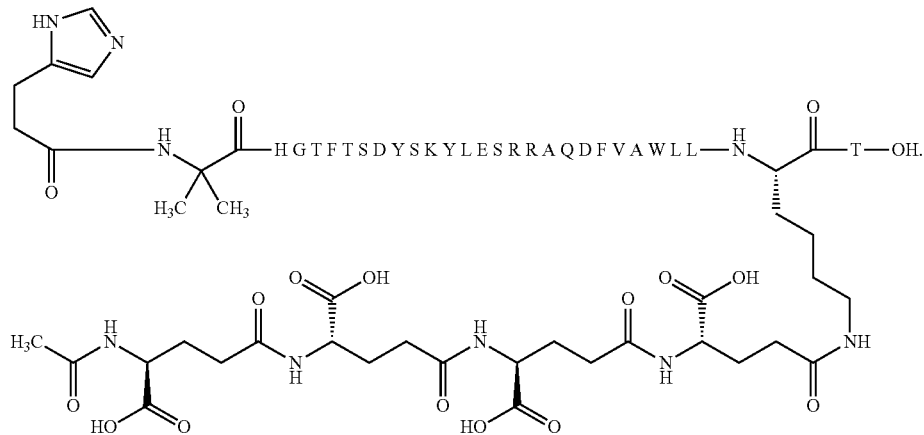

In one embodiment the derivative is N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys24, Leu27, Ser28]-Glucagon Chem. 5 (SEQ ID NO: 6)

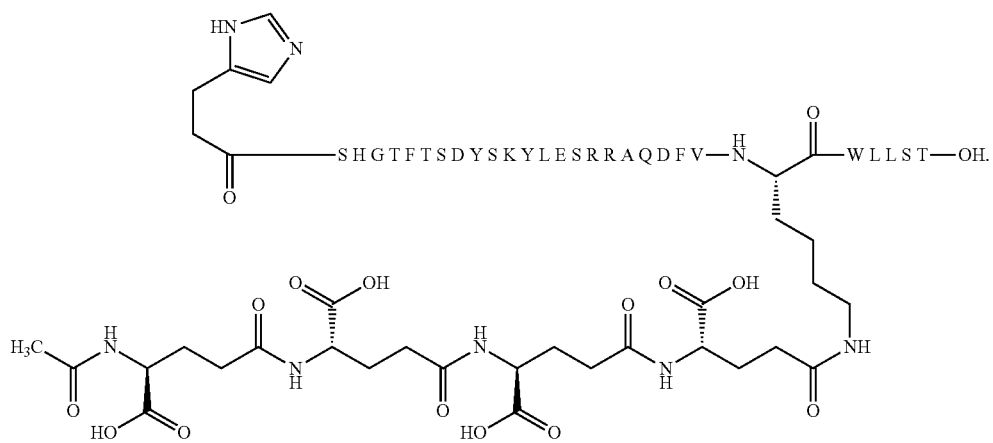

In one embodiment the derivative is $N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Ser28]-Glucagon Chem. 6 (SEQ ID NO: 7)

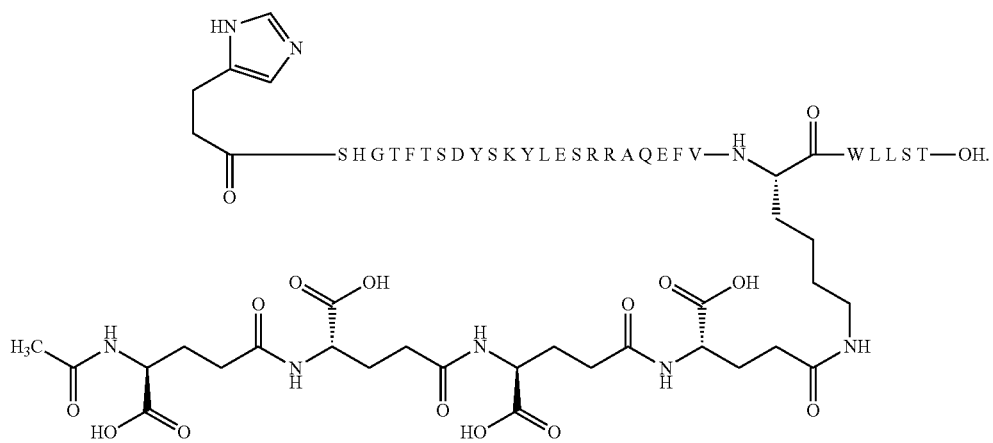

In one embodiment the derivative is $N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Glu21, Lys24, Leu27, Ser28]-Glucagon Chem. 7 (SEQ ID NO: 8)

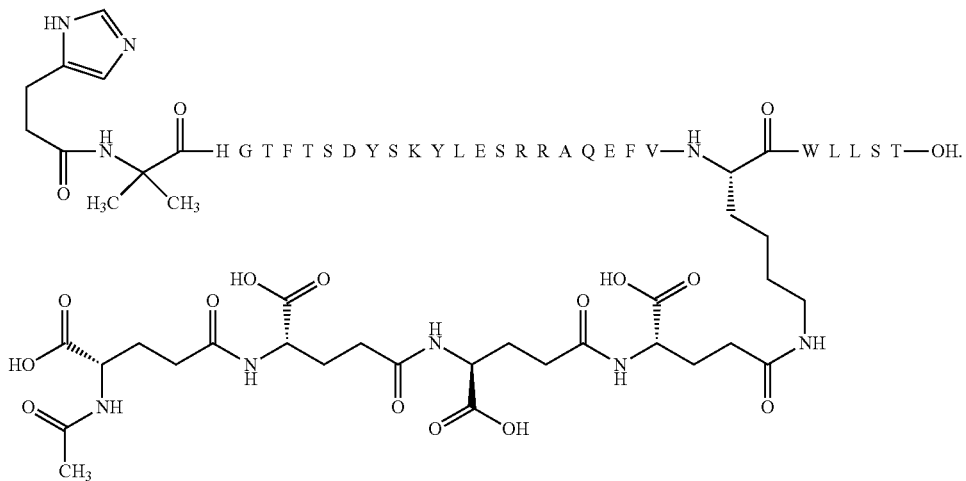

In one embodiment the derivative is $N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Leu16, Glu21, Lys24, Leu27, Ser28]-Glucagon Chem. 8 (SEQ ID NO: 9)

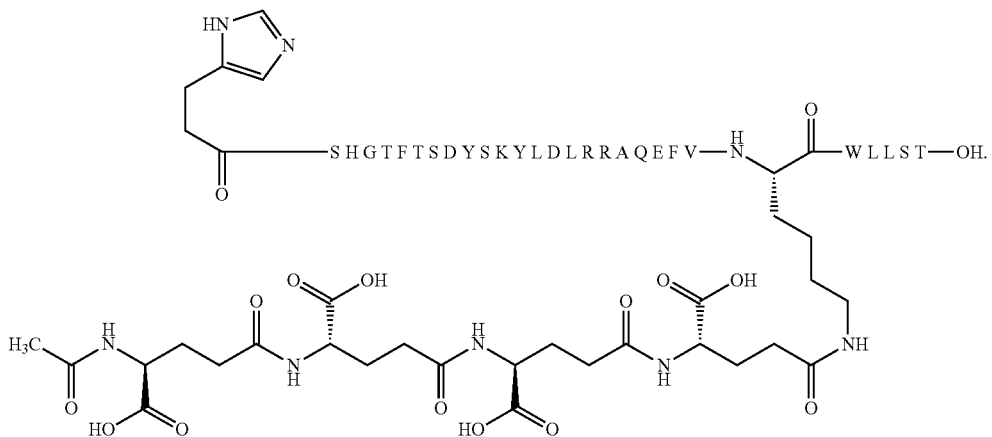

In one embodiment the derivative is $N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Leu16, Lys24, Leu27, Ser28]-Glucagon Chem. 9 (SEQ ID NO: 10)

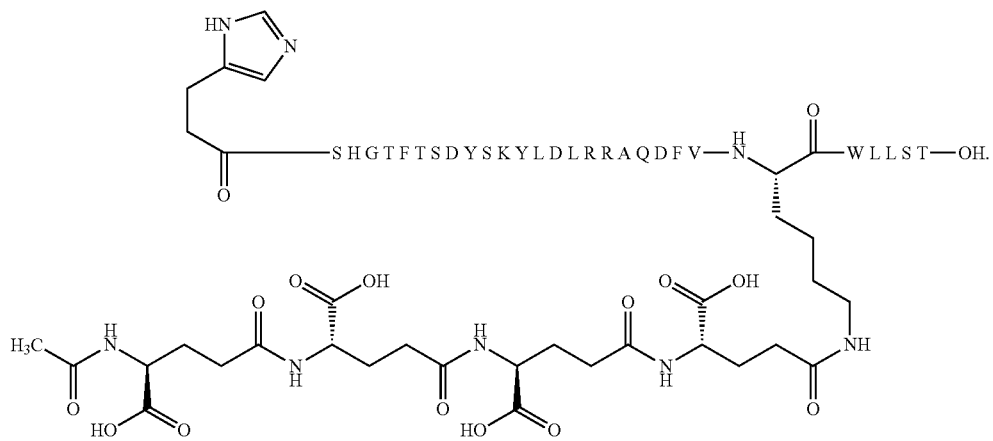

In one embodiment the derivative is N^ε24-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Val16, Lys24, Leu27, Ser28]-Glucagon Chem. 10 (SEQ ID NO: 11)

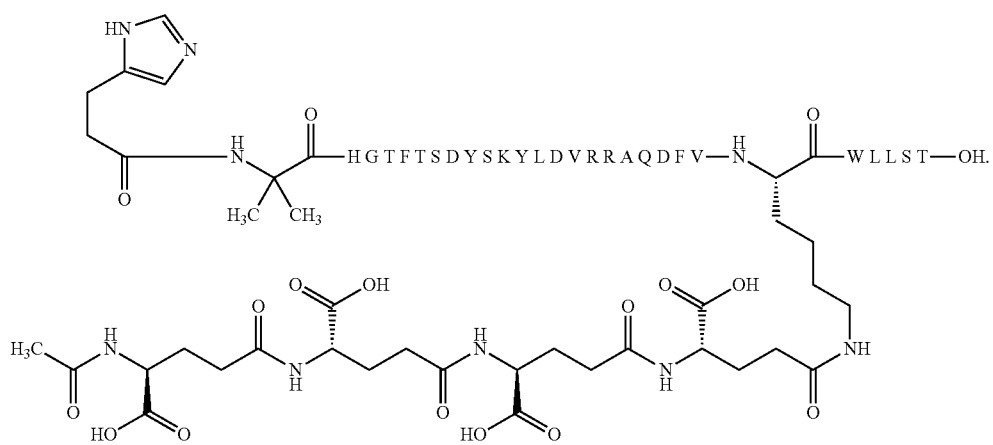

In one embodiment the derivative is N^ε16-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys16, Glu21, Leu27, Ser28]-Glucagon Chem. 11 (SEQ ID NO: 12)

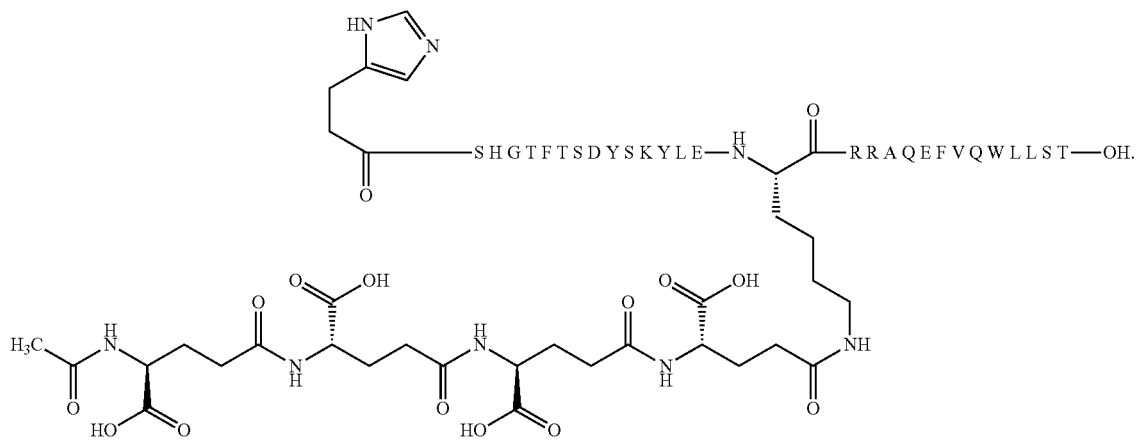

In one embodiment the derivative is $N^{\epsilon 20}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys20, Glu21, Leu27, Ser28]-Glucagon Chem. 12 (SEQ ID NO: 13)

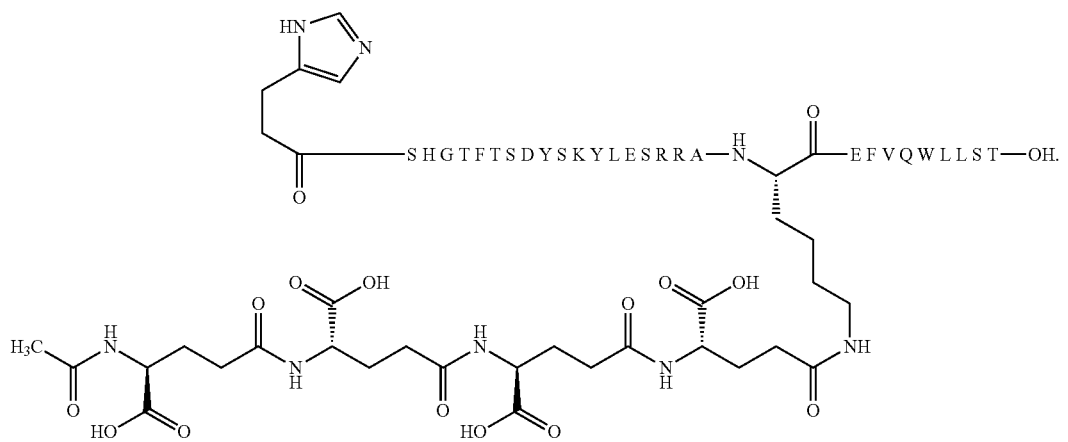

In one embodiment the derivative is $N^{21}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys21, Leu27, Ser28]-Glucagon Chem. 13 (SEQ ID NO: 14)

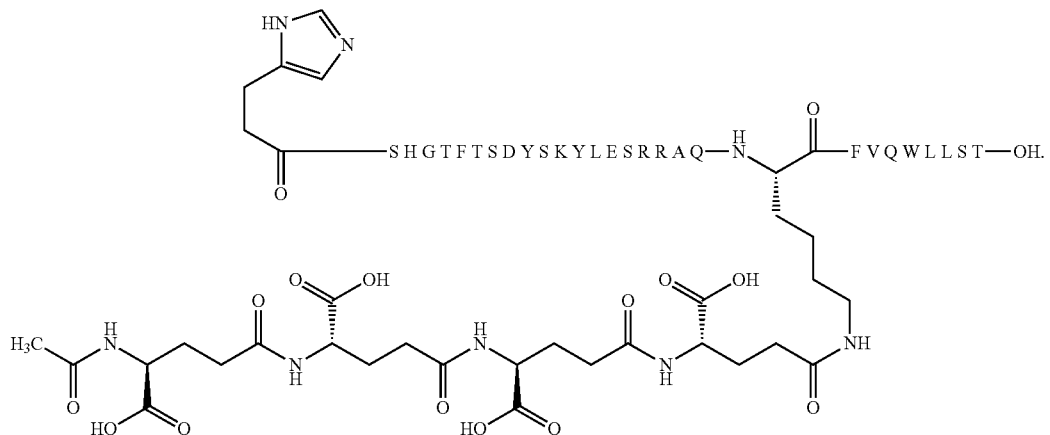

In one embodiment the derivative is $N^{\epsilon 28}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Leu27, Lys28]-Glucagon Chem. 14 (SEQ ID NO: 15)

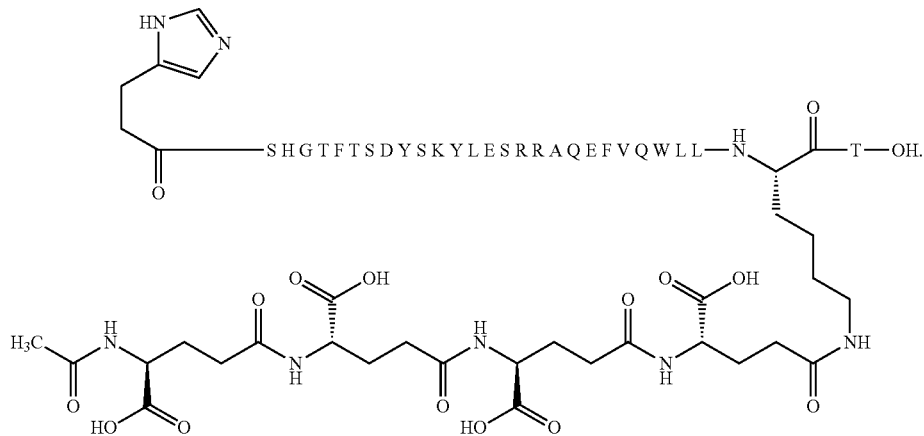

In one embodiment the derivative is $N^{\epsilon 29}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Leu27, Ser28, Lys29]-Glucagon Chem. 15 (SEQ ID NO: 16)

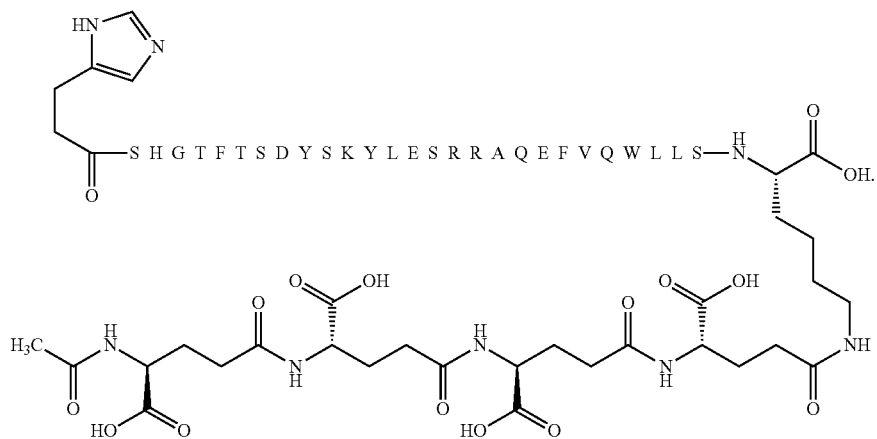

In one embodiment the derivative is N^α([Imp1, His3, Glu15, Glu21, Leu27, Ser28]-Glucagonyl)-N^ε[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]Lys Chem. 16 (SEQ ID NO: 17)

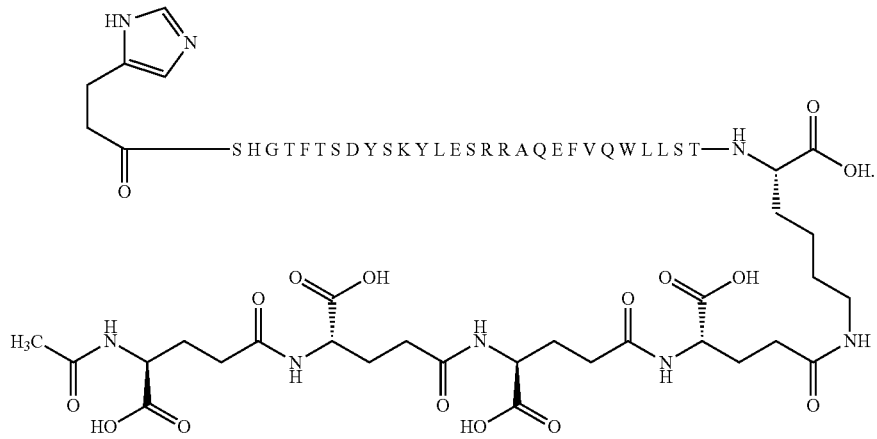

In one embodiment the derivative is N^ε24-[2-[[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]amino]acetyl]-[Imp1, His3, Glu15, Glu21, Lys24, Leu27, Ser28]-Glucagon Chem. 17 (SEQ ID NO: 7)

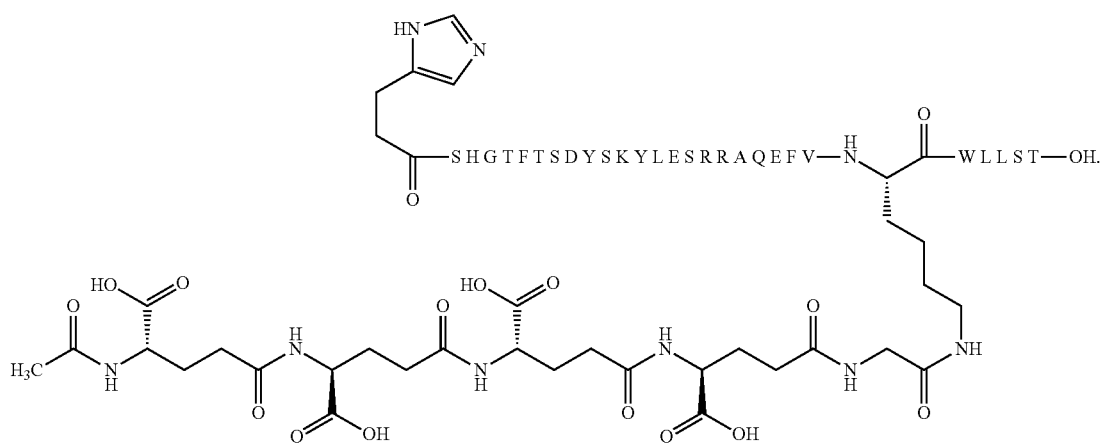

In one embodiment the derivative is $N^{\epsilon 24}$-[(4S)-4-[[(4S)-4-[[(4S)-4-acetamido-4-carboxybutanoyl]amino]-4-carboxybutanoyl]amino]-4-carboxybutanoyl]-[Imp1, His3, Glu15, Glu21, Lys24, Leu27, Ser28]-Glucagon Chem. 18 (SEQ ID NO: 7)

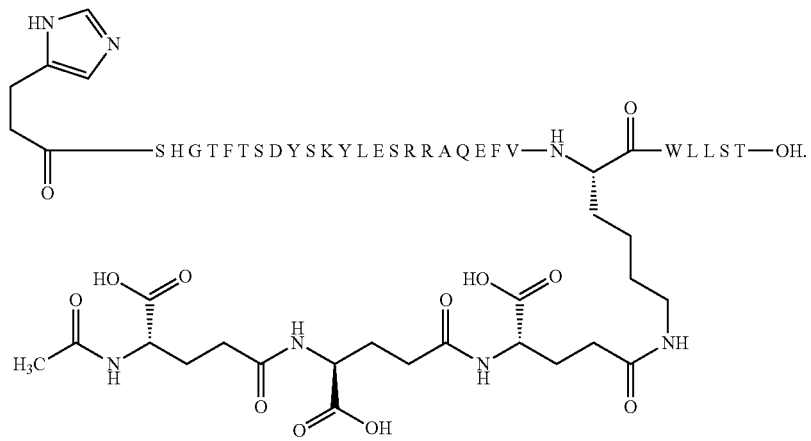

In one embodiment the derivative is $N^{\epsilon 24}$-[(4S)-4-[[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Ser28]-Glucagon Chem. 19 (SEQ ID NO: 7)

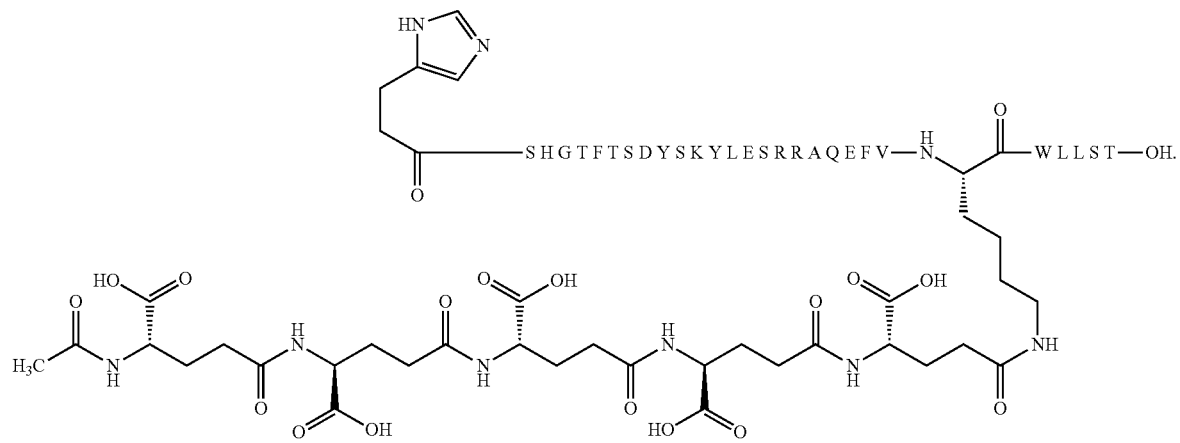

In one embodiment the derivative is $N^{\epsilon24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Ala16, Lys24, Leu27, Ser28]-Glucagon Chem. 20 (SEQ ID NO: 18)

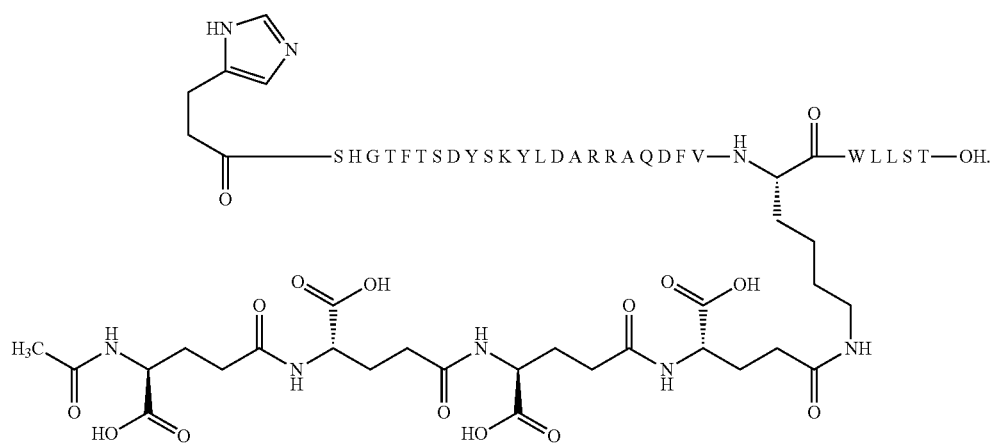

In one embodiment the derivative is $N^{\epsilon24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Aib16, Lys24, Leu27, Ser28]-Glucagon Chem. 21 (SEQ ID NO: 19)

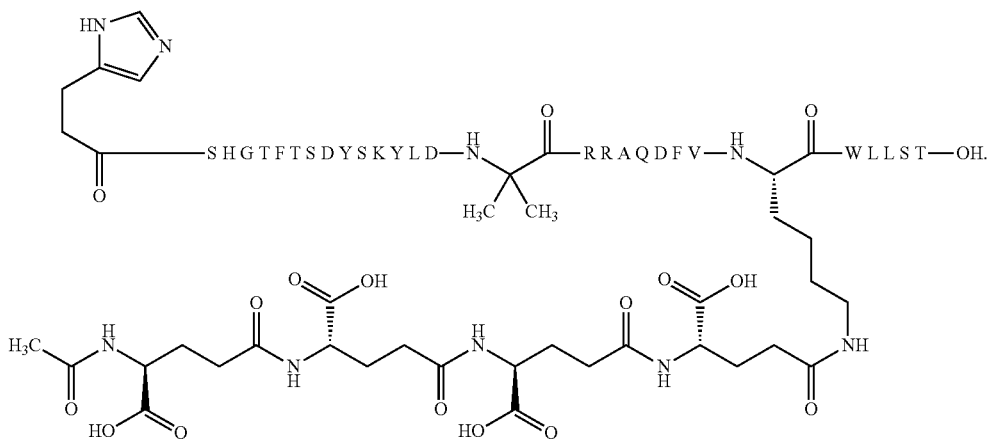

In one embodiment the derivative is N^ε24-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Glu28]-Glucagon substituent, if any, as well as in the glucagon analogue moiety. The glucagon analogue moiety often includes a free carboxylic acid group at the C-terminus, and it may also include free carboxylic groups at internal acid amino acid residues such as Asp and Glu.

Chem. 22 (SEQ ID NO: 20)

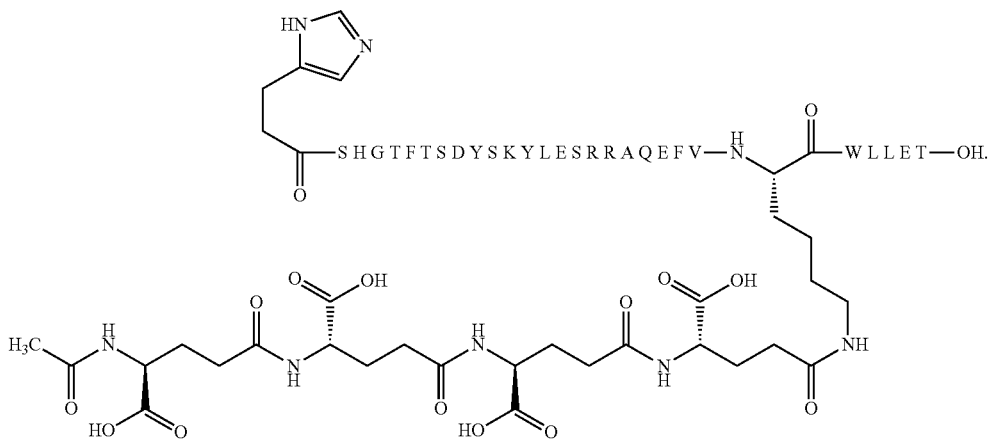

Pharmaceutically Acceptable Salt, Amide, Ester or Carboxylic Acid

The derivatives, analogues, and intermediate products of the invention may be in the form of a pharmaceutically acceptable salt, amide, carboxylic acid or ester. Salts are e.g. formed by a chemical reaction between a base and an acid, e.g.: $2NH_3 + H_2SO_4 \rightarrow (NH_4)_2SO_4$. The salt may be a basic salt, an acid salt, or it may be neither nor (i.e. a neutral salt). Basic salts produce hydroxide ions and acid salts hydronium ions in water. In one embodiment the derivative is a pharmaceutically acceptable salt, amide, or ester of said derivative.

The salts of the derivatives of the invention may be formed with added cations or anions between anionic or cationic groups, respectively. These groups may be situated in the glucagon analogue moiety, and/or in the substituent of the derivatives of the invention.

Non-limiting examples of anionic groups of the derivatives of the invention include free carboxylic groups in the Non-limiting examples of cationic groups in the glucagon analogue moiety include any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group.

The ester formation may involve the free carboxylic group at the C-terminus of the glucagon analogue, and/or any free carboxylic group in the substituent.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the glucagon analogue, any free carboxylic group in the substituent, the free amino group at the N-terminus of the glucagon analogue, and/or any free or substituted amino group of the glucagon analogue and/or the substituent. In one embodiment the derivative does not comprise a C-terminal amide of the glucagon analogue.

In one embodiment, unless otherwise stated, the derivative of the invention comprises a C-terminal carboxylic acid group. In one embodiment the invention relates to a pharmaceutically acceptable salt, amide or ester of the derivative. The term "pharmaceutically acceptable salt" is intended to indicate a salt which is not harmful to the patient. In one embodiment the derivative is in the form of a pharmaceutically acceptable salt. In one embodiment the carboxylic acid of the derivative is a derivative comprising an amide group at the C-terminus of the glucagon analogue, i.e. the glucagon analogue. In another particular embodiment, the derivative is in the form of a pharmaceutically acceptable amide, preferably with an amide group at the C-terminus of the glucagon analogue. In a still further particular embodiment, the glucagon analogue or derivative is in the form a pharmaceutically acceptable ester.

Preparation of Derivatives of Glucagon Peptides

The derivative of the invention may be prepared by the method described below.

SPPS General Methods

The Fmoc-protected amino acid derivatives to be used may be the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)-OH, Fmoc-Met-OH, Fmoc-Phe-OH, Fmoc-Pro-OH, Fmoc-Ser(tBu)-OH, Fmoc-Thr(tBu)-OH, Fmoc-Trp(BOC)-OH, Fmoc-Tyr(tBu)-OH, Fmoc-Val-OH and Fmoc-Lys(Mtt)-OH supplied from e.g. Anaspec, Bachem, Iris Biotech, or NovabioChem. 3-(N-1-Trityl-imidazol-4-yl)-propionic acid is used for incorporating Imp.

SPPS may be performed using Fmoc based chemistry on a Prelude Solid Phase Peptide Synthesizer from Protein Technologies (Tucson, Ariz. 85714 U.S.A.). A suitable resin for the preparation of C-terminal carboxylic acids is a Wang resin preloaded with an amino acid such as Fmoc-Thr(tBu)-Wang resin (Low Load, 0.35 mmol/g). In cases where the substituent is attached to the C-terminal lysine, a suitable resin is a pre-loaded fmoc-Lys(Mtt)-Wang. A suitable resin for the preparation of C-terminal peptide amides is H-Rink Amide-ChemMatrix resin (loading e.g. 0.52 nmol/g) or Rink Amide AM polystyrene resin (Novabiochem, loading e.g. 0.62 mmol/g) or the like. Fmoc-deprotection is achieved with 20% piperidine in NMP. Peptide couplings are performed by using either DIC/HOAt/collidine or DIC/Oxyma Pure/collidine without preactivation. Amino acid/HOAt or amino acid/Oxyma Pure solutions (0.3 M/0.3 M in NMP at a molar excess of 3-10 fold) are added to the resin followed by the same molar equivalent of DIC (3 M in NMP) followed by collidine (3 M in NMP). For example, the following amounts of 0.3 M amino acid/HOAt solution can be used per coupling for the following scale reactions: Scale/mL, 0.05 mmol/1.5 mL, 0.10 mmol/3.0 mL, 0.25 mmol/7.5 mL. The Mtt group may be removed by washing the resin with HFIP/DCM (75:25) (2×2 min), washing with DCM and suspending the resin in HFIP/DCM (75:25)(2×20 min) and subsequently washing in sequence with Piperidine/NMP (20:80), DCM(1×), NMP(1×), DCM(1×), NMP(1×).

Attachment of the Substituent

The substituent can be introduced in a stepwise procedure by the Prelude peptide synthesizer as described above using suitably protected building blocks, with the modification that the amino acids and carboxylic acid derivatives including Fmoc-Ado-OH, Fmoc-Glu-OtBu and acetic acid, propionic acid, isobutyric acid, butyric acid, pentanoic acid, hexanoic acid or 4-methyl pentanoic acid. After each coupling step, unreacted peptide intermediate can be capped using acetic acid anhydride and collidine in excess (>10 eq.).

The introduction of a substituent on the epsilon-nitrogen of a lysine is achieved using a Lysine protected with Mtt (Fmoc-Lys(Mtt)-OH). Alternatively, the epsilon-nitrogen of a lysine could be protected with an ivDde group (Fmoc-Lys (ivDde)-OH). The incorporation of gamma-Glu moieties in the substituent may be achieved by coupling with the amino acid Fmoc-Glu-OtBu.

Introduction of each moiety in the substituent can be achieved using prolonged coupling time (1×6 hours) followed by capping with acetic anhydride or alternatively acetic acid/DIC/HOAt/collidine. Acetylation of the terminal nitrogen on the substituent is achieved using acetic anhydride (10 eq.) and collidine (20 eq.) in NMP.

Cleavage from the Resin

After synthesis the resin is washed with DCM, and the peptide is cleaved from the resin by a 2-3 hour treatment with TFA/TIS/water (95/2.5/2.5) followed by precipitation with diethylether. The precipitate is washed with diethylether.

Purification and Quantification

The crude peptide is dissolved in a suitable mixture of water and MeCN, such as water/MeCN (4:1), and purified by reversed-phase preparative HPLC (Waters Deltaprep 4000 or Gilson) on a column containing C18-silica gel. Elution is performed with an increasing gradient of MeCN in water containing 0.1% TFA. Relevant fractions are checked by analytical HPLC or UPLC. Fractions containing the pure target peptide are mixed and concentrated under reduced pressure. The resulting solution is analyzed (HPLC, LCMS) and the product (i.e. the derivative) is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying affords the peptide trifluoroacetate as a white solid.

Intermediate Products

In one embodiment the invention relates to an intermediate product in the form of a glucagon analogue which comprises the following modifications as compared to glucagon (SEQ ID NO: 1):

(i) [Imp1, Aib2, His3, Leu16, Lys24, Leu27, Ser28]-Glucagon;

(ii) [Imp1, Aib2, His3, Glu15, Lys24, Leu27, Ser28]-Glucagon;

(iii) [Imp1, Aib2, His3, Leu10, Glu15, Lys24, Leu27, Ser28]-Glucagon;

(iv) [Imp1, Aib2, His3, Glu15, Ala24, Leu27, Lys28]-Glucagon;

(v) [Imp1, His3, Glu15, Lys24, Leu27, Ser28]-Glucagon;

(vi) [Imp1, His3, Glu15, Glu21, Lys24, Leu27, Ser28]-Glucagon;

(vii) [Imp1, Aib2, His3, Glu15, Glu21, Lys24, Leu27, Ser28]-Glucagon;

(viii) [Imp1, His3, Leu16, Glu21, Lys24, Leu27, Ser28]-Glucagon;

(ix) [Imp1, His3, Leu16, Lys24, Leu27, Ser28]-Glucagon;

(x) [Imp1, Aib2, His3, Val16, Lys24, Leu27, Ser28]-Glucagon;

(xi) [Imp1, His3, Glu15, Lys16, Glu21, Leu27, Ser28]-Glucagon;

(xii) [Imp1, His3, Glu15, Lys20, Glu21, Leu27, Ser28]-Glucagon;

(xiii) [Imp1, His3, Glu15, Lys21, Leu27, Ser28]-Glucagon;

(xiv) [Imp1, His3, Glu15, Glu21, Leu27, Lys28]-Glucagon;
(xv) [Imp1, His3, Glu15, Glu21, Leu27, Ser28, Lys29]-Glucagon;
(xvi) [Imp1, His3, Glu15, Glu21, Leu27, Ser28, Lys30]-Glucagon;
or a pharmaceutically acceptable salt, amide, or ester thereof. In one embodiment the invention relates to an intermediate product in the form of a glucagon analogue which comprises the following modifications as compared to glucagon (SEQ ID NO: 1):
(xvii) [Imp1, His3, Ala16, Lys24, Leu27, Ser28]-Glucagon;
(xviii) [Imp1, His3, Aib16, Lys24, Leu27, Ser28]-Glucagon;
(xix) [Imp1, His3, Glu15, Glu21, Lys24, Leu27, Glu28]-Glucagon;
or a pharmaceutically acceptable salt, amide, or ester thereof.

In one embodiment the invention relates to an intermediate product, wherein the glucagon analogue is selected from the following analogues of glucagon (SEQ ID NO: 1):
(i-a) [Imp1, Aib2, His3, Leu16, Lys24, Leu27, Ser28]-Glucagon;
(ii-a) [Imp1, Aib2, His3, Glu15, Lys24, Leu27, Ser28]-Glucagon;
(iii-a) [Imp1, Aib2, His3, Leu10, Glu15, Lys24, Leu27, Ser28]-Glucagon;
(iv-a) [Imp1, Aib2, His3, Glu15, Ala24, Leu27, Lys28]-Glucagon;
(v-a) [Imp1, His3, Glu15, Lys24, Leu27, Ser28]-Glucagon;
(vi-a) [Imp1, His3, Glu15, Glu21, Lys24, Leu27, Ser28]-Glucagon;
(vii-a) [Imp1, Aib2, His3, Glu15, Glu21, Lys24, Leu27, Ser28]-Glucagon;
(viii-a) [Imp1, His3, Leu16, Glu21, Lys24, Leu27, Ser28]-Glucagon;
(ix-a) [Imp1, His3, Leu16, Lys24, Leu27, Ser28]-Glucagon;
(x-a) [Imp1, Aib2, His3, Val16, Lys24, Leu27, Ser28]-Glucagon;
(xi-a) [Imp1, His3, Glu15, Lys16, Glu21, Leu27, Ser28]-Glucagon;
(xii-a) [Imp1, His3, Glu15, Lys20, Glu21, Leu27, Ser28]-Glucagon;
(xiii-a) [Imp1, His3, Glu15, Glu21, Lys21, Leu27, Ser28]-Glucagon;
(xiv-a) [Imp1, His3, Glu15, Glu21, Leu27, Lys28]-Glucagon;
(xv-a) [Imp1, His3, Glu15, Glu21, Leu27, Ser28, Lys29]-Glucagon;
(xvi-a) [Imp1, His3, Glu15, Glu21, Leu27, Ser28]-Glucagon;
or a pharmaceutically acceptable salt, amide, or ester thereof. In one embodiment the invention relates to an intermediate product, wherein the glucagon analogue is selected from the following analogues of glucagon (SEQ ID NO: 1):
(xvii-a) [Imp1, His3, Ala16, Lys24, Leu27, Ser28]-Glucagon;
(xviii-a) [Imp1, His3, Aib16, Lys24, Leu27, Ser28]-Glucagon;
(xix-a) [Imp1, His3, Glu15, Glu21, Lys24, Leu27, Glu28]-Glucagon;
or a pharmaceutically acceptable salt, amide, or ester thereof.

The glucagon derivatives of the invention may be prepared by the following a stepwise synthesis method comprising (i) preparation of the intermediate glucagon analogue followed by (ii) attachment of the substituent. Step (i) of this method can be achieved using standard solid phase synthesis as described in the experimental section using protected amino acids; after cleavage from the resin the glucagon analogue can be subjected to purification using preparative HPLC as described in the experimental section herein to give the intermediate product. Alternatively, step (i) of this method, preparation of the intermediate product, can be carried out using a semi-recombinant synthesis as described in WO2009/083549. Step (ii) of this method, i.e. the attachment of the substituent to the intermediate product leading to the final product, as well as preparation of the substituent itself can be achieved using methods described in WO2009/083549.

Functional Properties

In a first functional embodiment, the derivative of the invention is chemically stable. Also, or alternatively, in a second functional embodiment, the derivative is physically stable. Also, or alternatively, in a third functional embodiment, the derivative has a good receptor binding and potency on the glucagon receptor. Also, or alternatively, in a fourth functional embodiment, the derivative is a fast-acting derivative. Also, or alternatively, in a fourth functional embodiment, the derivative has a high solubility. Also, or alternatively, in a sixth functional embodiment, the derivative has a high ratio (or a ratio equivalent to that of human glucagon (SEQ ID NO: 1)) between its EC50 on the GLP-1 receptor and its EC50 on the glucagon receptor. In one embodiment the effects in the functional embodiments are determined relative to human glucagon (SEQ ID NO: 1).

Chemical Stability

The term "chemical stability" of the peptide composition as used herein refers to chemical covalent changes in the peptide structure leading to formation of chemical degradation products with potential less biological potency and/or potential increased immunogenic properties compared to the native peptide (e.g. human glucagon) structure. Various chemical degradation products can be formed depending on the type and nature of the native peptide and the environment to which the peptide is exposed. Chemical degradation can most likely not be completely avoided and increasing amounts of chemical degradation products is often seen during prolonged storage. Most peptides are prone to deamidation, a process in which the side chain amide group in glutaminyl or asparaginyl residues is hydrolysed to form a free carboxylic acid. Other degradations pathways involves formation of high molecular weight transformation products where two or more peptide molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. Asparagine or aspartic acid containing peptides may be prone to isomerization via the formation of an intermediate aspartimide giving rise to the corresponding iso-aspartic acid isomer in where both the D- and L-isomer can be formed. The aspartimide intermediate may also lead to the formation of the D-aspartic acid isomer. (Formulation Consideration for Proteins Susceptible to Asparagine Deamidation and Aspartate Isomerization, Wakankar and Borchardt, Journal of Pharmaceutical Sciences, 2006, Vol. 95, no. 11, p 2321). Finally, peptides may also undergo hydrolytic cleavage in which peptide fragments or single amino acids are cleaved by hydrolysis of the peptide bond.

The chemical stability of the composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SE-HPLC and/or RP-UPLC).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

Chemical stability of the derivative may be measured by determination of the chemical degradation in Assay (IV) described herein. In one embodiment the chemically stable derivative has a chemical degradation of less than 5%, such as less than 4%, less than 3% or less than 2%, wherein said chemical degradation may be determined by Assay (IV) described herein. In one embodiment the derivative has a chemical degradation of less than 5%, such as less than 4%, less than 3% or less than 2%, wherein said chemical degradation may be determined by Assay (IV) described herein.

Physical Stability

Peptides may undergo various changes of physical state. Peptides may precipitate due to lack of solubility at a certain set of conditions, e.g. due to neutralization of repulsing charges on amino acid side chains due to a change of pH. Another physical change is the formation of amyloid fibrils, which involves a conformational change into beta-sheet rich macromolecular fibre structures. Other macromolecular structures may be formed by less systematic structural repeats due to aggregation. In the two latter instances peptide substance may eventually be observed as a precipitate. In fact these physical changes may to some extent be interrelated, e.g. solubility versus pH and fibril formation is related [Schmittschmitt and Scholtz, Protein Science, 12, 10, 2374-2378, 2003]. Furthermore, it is very difficult to distinguish these phenomena by visual inspection only, therefore the result of these changes are often described by the general term "precipitate".

Other changes of physical state include adsorption to surfaces observed as a loss of content of peptide from solution, and the change from a liquid solution to a gel. Nevertheless, the observation of a precipitate regardless its nature or formation of a gel is a problem when in a pharmaceutical injectable during its storage and in-use time.

Glucagon has a very low aqueous solubility at neutral pH, which disables pharmaceutical composition at neutral pH. Even when dissolved at acidic pH, glucagon may undergo various phase transitions that depend on concentration and temperature and is thus very physically unstable. After dissolving samples of glucagon in hydrochloric acid a lag-phase may occur where the viscosity of the sample is low and the solution is fully transparent. After some hours the viscosity begins to increase—indicative of a gel formation (Beaven et al, European J. Biochem. 11 (1969) 37-42). After reaching a plateau viscosity may begin to fall again and at the same time fibrils may appear and precipitate out of solution. The process is seedable, addition of a small amount of pre-formed gel reduce the lag-phase. Formation of gels and fibrillation is highly dependent of physical stress, such as heating and shaking, both increasing the rate of the process.

The term "physical stability" of the composition as used herein refers to the tendency of the peptide and/or protein to form biologically inactive and/or insoluble aggregates of the peptide and/or protein as a result of exposure of the peptide and/or protein to thermo-mechanical stresses and/or interaction with interfaces and surfaces that are destabilizing, such as hydrophobic surfaces and interfaces. Physical stability of the aqueous peptide and/or protein compositions is evaluated by means of visual inspection and/or turbidity measurements after exposing the composition filled in suitable containers (e.g. cartridges or vials) to mechanical/physical stress (e.g. agitation) at different temperatures for various time periods. Visual inspection of the compositions is performed in a sharp focused light with a dark background. The turbidity of the composition is characterized by a visual score ranking the degree of turbidity for instance on a scale from 0 to 3 (a composition showing no turbidity corresponds to a visual score 0, and a composition showing visual turbidity in daylight corresponds to visual score 3). A composition is classified physical unstable with respect to protein aggregation, when it shows visual turbidity in daylight. Alternatively, the turbidity of the composition can be evaluated by simple turbidity measurements well-known to the skilled person. Physical stability of the aqueous peptide and/or protein compositions can also be evaluated by using a spectroscopic agent or probe of the conformational status of the peptide and/or protein. The probe is preferably a small molecule that preferentially binds to a non-native conformer of the peptide and/or protein. One example of a small molecular spectroscopic probe of peptide and/or protein structure is Thioflavin T. Thioflavin T is a fluorescent dye that has been widely used for the detection of amyloid fibrils. In the presence of fibrils, and perhaps other peptide and/or protein configurations as well, Thioflavin T gives rise to a new excitation maximum at about 450 nm and enhanced emission at about 482 nm when bound to a fibril peptide and/or protein form. Unbound Thioflavin T is essentially non-fluorescent at these wavelengths.

Other small molecules can be used as probes of the changes in peptide and/or protein structure from native to non-native states. For instance the "hydrophobic patch" probes that bind preferentially to exposed hydrophobic patches of a peptide and/or protein. The hydrophobic patches are generally buried within the tertiary structure of a peptide and/or protein in its native state, but become exposed as a peptide and/or protein begins to unfold or denature. Examples of these small molecular, spectroscopic probes are aromatic, hydrophobic dyes, such as antrhacene, acridine, phenanthroline or the like.

Physical stability of the derivative may be determined by the recovery and/or lag time in Assay (III) described herein, i.e. the ThT fibrillation assay. In one embodiment the physically stable derivative has more than 70% recovery and/or more than 7 hours lag time in Assay (III) described herein.

In one embodiment the derivative has more than 70% recovery in a ThT fibrillation assay, such as Assay (III) described herein. In one embodiment the derivative has more than 90%, such as more than 95% or more than 98%, recovery in a ThT fibrillation assay, such as Assay (III) described herein. In one embodiment the derivative has about 100% recovery in a ThT fibrillation assay, such as Assay (III) described herein.

In one embodiment the derivative has more than 7 hours, such as more than 20 hours or more than 45 hours, lag time in a ThT fibrillation assay, such as Assay (III) described herein.

Receptor Binding and Potency

The derivatives of the invention are glucagon receptor agonists. A receptor agonist may be defined as a derivative that binds to a receptor and elicits a response typical of the natural ligand. In one embodiment the term "glucagon receptor" as used herein means the human glucagon receptor.

In one embodiment the derivative of the invention is a glucagon receptor agonist and/or has glucagon receptor activity. In one embodiment the glucagon analogue of the invention is a glucagon receptor agonist and/or has glucagon receptor activity. In one embodiment the glucagon peptide is a glucagon receptor agonist and/or has glucagon receptor activity. The term "glucagon receptor activity" refers to the ability to bind to the glucagon receptor and activate intracellular signal transduction pathways, such as activation of adenylate cyclase and increased levels of intracellular cAMP, mediating the physiological effects as is known in the art. For example, the derivatives or analogues of the invention can be tested for glucagon receptor activity using Assay (I)(b) or Assay (II)(b) described herein.

In one embodiment the derivative is an agonist of the glucagon receptor, with an EC50 of no more than 200 pM. In one embodiment the derivative is an agonist of the glucagon receptor having an EC50 below 200 pM, such as below 100 pM or below 20 pM, as determined by e.g. Assay (I)(b) described herein. In another embodiment the derivative is an agonist of the glucagon receptor having an EC50 below 10 pM, such as below 5 pm, as determined by e.g. Assay (I)(b) described herein.

In one embodiment the derivative has a ratio between its EC50 on the GLP-1 receptor and its EC50 on the glucagon receptor of at least 50, such as at least 100, 1000 or 5000, wherein said potencies (i.e. EC50) may be determined using Assay (I)(a) and Assay (I)(b) described herein.

In one embodiment the derivative of the invention has an IC50 of below 100 nM, such as below 50 nM, below 10 nM or below 2 nM, as determined by Assay (II)(b) described herein.

Fast-Acting Derivative

In one embodiment the derivative is a fast-acting derivative. In one embodiment, as used herein, a "fast-acting derivative" has a fast onset of hyperglycaemic effect. In one embodiment a "fast-acting derivative" has onset of action of the hyperglycemic effect equivalent to that of glucagon (SEQ ID NO: 1) after subcutaneous or intramuscular administration.

In one embodiment the fast-acting derivative has improved bioavailability compared to human glucagon (SEQ ID NO: 1) after subcutaneous or intramuscular administration.

Solubility

The derivatives of the invention may be soluble glucagon receptor agonists. In one embodiment the solubility of the derivative is at least 0.1 mmol/l, at least 0.2 mmol/l or at least 0.5 mmol/l, such as at least 2 mmol/l, at least 4 mmol/l or at least 8 mmol/l, or such as at least 10 mmol/l or at least 15 mmol/l. In one embodiment the terms "soluble", "solubility" and "aqueous solubility", when used in relation to a derivative of the invention, refer to the solubility of a the derivative 1) in water or 2) in an aqueous salt or aqueous buffer solution, for example a 10 mM phosphate solution, or 3) in an aqueous solution containing other compounds, and wherein said solubility may be determined at a pH in the range between 6.5 and 8.5, such as between 7.0 and 8.5 or between 7.4 and 8.2.

In one embodiment the soluble derivative has a solubility in 10 mM phosphate solution with pH in the range of 7.0-8.5, such as 7.4-8.2, of at least 0.1 mmol/l.

In one embodiment the derivative has a solubility of at least 0.1 mmol/l. In one embodiment the solubility of the derivative may be determined in a composition comprising said derivative in 10 mM phosphate buffer at a pH in the range of 7.4-8.2.

Pharmaceutical Compositions

In one embodiment the invention relates to a pharmaceutical composition comprising the derivative of the invention and one or more pharmaceutically acceptable excipients. In one embodiment the composition is suited for parenteral administration, such as SC, IM or IV administration. The terms "pharmaceutical composition" and "composition" are used interchangeably herein.

Pharmaceutical compositions containing a derivative of the invention may be prepared by conventional techniques, e.g. as described in Remington's Pharmaceutical Sciences, 1985 or in Remington: The Science and Practice of Pharmacy, 19th edition, 1995.

In one embodiment the invention relates to a pharmaceutical composition comprising a derivative of the invention, wherein said derivative is present in a concentration from about 0.01 mg/mL to about 25 mg/mL, such as from about 0.05 mg/mL to about 5 mg/mL and from about 0.1 mg/mL to about 2 mg/mL, and wherein said composition has a pH from 2.0 to 10.0. The pharmaceutical composition may comprise a derivative of the invention, wherein said derivative is present in a concentration from about 0.01 mg/mL to about 50 mg/mL, and wherein said composition has a pH from 2.0 to 10.0.

In one embodiment the pharmaceutical composition comprises an aqueous solution of a derivative of the invention, and a buffer, wherein said derivative is present in a concentration from 0.01 mg/mL or above, and wherein said composition has a pH from about 2.0 to about 10.0. In another embodiment the pharmaceutical composition comprises an aqueous solution of a derivative of the invention, and a buffer, wherein said derivative is present in a concentration from 0.01 mg/mL or above, and wherein said composition has a pH from about 6.5 to about 8.5.

In one embodiment the composition of the invention has a pH from about 2.0 to about 10.0. In another embodiment the composition has a pH from about 6.5 to about 8.5. In a further embodiment the composition has a pH from about 7.0 to about 8.5, such as from about 7.2 to about 8.2.

The composition may further comprise a buffer system, preservative(s), isotonicity agent(s), chelating agent(s), stabilizers and surfactants. In one embodiment the pharmaceutical composition is an aqueous composition, i.e. a composition comprising water. Such composition is typically a solution or a suspension. In a further embodiment of the invention the pharmaceutical composition is an aqueous solution. The term "aqueous composition" is defined as a composition comprising at least 50% w/w water. Likewise, the term "aqueous solution" is defined as a solution comprising at least 50% w/w water. In one embodiment the composition comprises a non-aqeuous organic solvent.

In another embodiment the pharmaceutical composition is a freeze-dried composition to which solvents and/or diluents are added prior to use, e.g. by the physician or the patient.

In another embodiment the pharmaceutical composition is a dried composition (e.g. freeze-dried or spray-dried) ready for use without any prior dissolution.

In one embodiment the invention relates to a composition comprising the derivative of the invention and one or more other active ingredients, such as GLP-1, insulin or analogues and/or derivatives thereof. In one embodiment the invention relates to a composition comprising the derivative of the invention and GLP-1 or analogues and/or derivatives thereof. In one embodiment the invention relates to a composition comprising the derivative of the invention and insulin or analogues and/or derivatives thereof. A composition comprising the derivative of the invention and one or more other active ingredients may be referred to as a "co-formulation". In one embodiment such co-formulations are physically stable and/or chemically stable compositions.

The fact that the derivatives of the invention may be soluble at neutral pH, may allow a co-formulation with insulin and allow for more stable blood glucose levels and a reduced number of hypoglycaemic episodes, as well as a reduced risk of diabetes related complications.

Pharmaceutical Administration

The derivative of the invention may be administered parenterally to a patient. The route of administration of the derivative may be intramuscular (IM), subcutaneous (SC), or intravenous (IV). It is recommended that the dosage of the compositions comprising the derivative of this invention which is to be administered to the patient be selected by a physician.

Parenteral administration may be performed by subcutaneous, intramuscular, intraperitoneal or intravenous injection by means of a syringe, optionally a pen-like syringe. In one embodiment the compositions comprising the derivative of the invention can be used in ready to use pen devices for glucagon administration. Alternatively, parenteral administration can be performed by means of an infusion pump. In one embodiment the compositions comprising the derivative of the invention can be used in pumps for glucagon administration. Parenteral administration may be nasal administration. As a further option, the glucagon preparations containing the derivative of the invention can also be adapted to transdermal administration, e.g. by needle-free injection or from a patch, optionally an iontophoretic patch, or transmucosal, e.g. buccal, administration.

A typical dosage of a derivative or composition of the invention when employed in a method according to the invention is in the range of from about 0.0001 to about 1 mg/kg body weight per day, preferably from about 0.001 to about 1 mg/kg body weight, more preferably from about 0.005 to about 0.02 mg/kg body. As described above, derivatives of the invention may be administered or applied in combination with one or more additional therapeutically active compounds or substances, and suitable additional compounds or substances may be selected, for example, from antidiabetic agents, antihyperlipidemic agents, anti-obesity agents, antihypertensive agents and agents for the treatment of complications resulting from, or associated with, diabetes.

Suitable antidiabetic agents include insulin, insulin derivatives or analogues, GLP-1 (glucagon like peptide-1) derivatives or analogues [such as those disclosed in WO 98/08871 (Novo Nordisk A/S), or other GLP-1 analogues such as exenatide (Byetta, Eli Lilly/Amylin; AVE0010, Sanofi-Aventis), taspoglutide (Roche), albiglutide (Syncria, GlaxoSmithKline)], amylin, amylin analogues (e.g. Symlin/Pramlintide) as well as orally active hypoglycemic agents.

Pharmaceutical Indications

The present invention also relates to a derivative of the invention, for use in medicine. In one embodiment the derivative is used for treating and/or preventing hypoglycaemia.

In one embodiment the invention relates to a method for treating and/or preventing hypoglycaemia comprising administering a therapeutically effective amount of the derivative of the invention to a patient in need thereof.

In one embodiment the derivative of the invention is used for treatment or prevention of hypoglycaemia, insulin induced hypoglycaemia, reactive hypoglycaemia, diabetic hypoglycaemia, non-diabetic hypoglycaemia, fasting hypoglycaemia, drug-induced hypoglycaemia, gastric by-pass induced hypoglycaemia, hypoglycaemia in pregnancy, alcohol induced hypoglycaemia, insulinoma and/or Von Girkes disease.

In one embodiment the derivatives of the invention are for use in inhibition of the motility of the gastrointestinal tract, which is useful in connection with investigations of the gastrointestinal tract using techniques such as x-ray, CT- and NMR-scanning.

In one embodiment the derivative is for use in treatment of beta-blocker poisoning. In one embodiment the derivative is for use in treatment or prevention of hepatic steatosis. In one embodiment the derivative is for use in treatment or prevention of hypoglycaemia. In one embodiment the derivative is for use in treatment or prevention of insulin induced hypoglycaemia. In one embodiment the derivative is for use in treatment or prevention of reactive hypoglycaemia. In one embodiment the derivative is for use in treatment or prevention of diabetic hypoglycaemia. In one embodiment the derivative is for use in treatment or prevention of non-diabetic hypoglycaemia. In one embodiment the derivative is for use in treatment or prevention of fasting hypoglycaemia. In one embodiment the derivative is for use in treatment or prevention of drug-induced hypoglycaemia. In one embodiment the derivative is for use in treatment or prevention of gastric by-pass induced hypoglycaemia. In one embodiment the derivative is for use in treatment or prevention of hypoglycaemia in pregnancy. In one embodiment the derivative is for use in treatment or prevention of alcohol-induced hypoglycaemia. In one embodiment the derivative is for use in treatment or prevention of insulinoma. In one embodiment the derivative is for use in treatment or prevention of Von Girkes disease.

In one embodiment the derivative is administered in a dosage regime which provides a therapeutically effective amount of said derivative. As used herein, the term "therapeutically effective amount" of a derivative of the invention refers to an amount sufficient to cure, alleviate or partially arrest the clinical manifestations of a given disease and/or its complications. An amount adequate to accomplish this is defined as a "therapeutically effective amount". Effective amounts for each purpose will depend on the severity of the disease or injury, as well as on the weight and general state of the patient. It will be understood that determination of an appropriate dosage may be achieved using routine experimentation, by constructing a matrix of values and testing different points in the matrix, all of which is within the level of ordinary skill of a trained physician or veterinarian.

The terms "treatment", "treating" and other variants thereof as used herein refer to the management and care of a patient or patient for the purpose of combating a condition, such as a disease or a disorder. The terms are intended to include the full spectrum of treatments for a given condition from which the patient is suffering, such as administration of the active compound(s) in question to alleviate symptoms or complications thereof, to delay the progression of the disease, disorder or condition, to cure or eliminate the disease, disorder or condition, and/or to prevent the condition, in that prevention is to be understood as the management and care of a patient for the purpose of combating the disease, condition, or disorder, and includes the administration of the active compound(s) in question to prevent the onset of symptoms or complications. The patient to be treated is preferably a mammal, in particular a human being, but treatment of other animals, such as dogs, cats, cows, horses, sheep, goats or pigs, is within the scope of the invention.

Additional particular embodiments of the derivatives of the invention are described in the section headed "Particular Embodiments".

Particular Embodiments

The following are non-limiting particular embodiments of the invention:

1. A derivative of a glucagon analogue comprising formula I (SEQ ID NO: 21):

```
Imp-X2-His-Gly-Thr-Phe-Thr-Ser-Asp-X10-Ser-X12-

Tyr-Leu-X15-X16-Arg-Arg-Ala-X20-X21-Phe-Val-X24-

Trp-Leu-X27-X28-X29-X30    [I]
``` wherein
$X_2$ is Ser or Aib;
$X_{10}$ is Tyr, Leu, Ile or Val;
$X_{12}$ is Lys or Arg;
$X_{15}$ is Asp or Glu;
$X_{16}$ is Ser, Ala, Leu, Thr, Aib, Ile, Val or Lys;
$X_{20}$ is Gln, Glu, Aib or Lys;
$X_{21}$ is Asp, Glu or Lys;
$X_{24}$ is Gln, Ala, Glu, Aib or Lys;
$X_{27}$ is Met, Leu or Val;
$X_{28}$ is Asn, Ser, Thr, Gln, Ala, Gly, Glu or Lys;
$X_{29}$ is Thr, Gly, Ser, Gln, Ala, Glu or Lys; and
$X_{30}$ is absent or is Lys;
and wherein said derivative comprises a substituent covalently attached to the nitrogen atom of the side chain of a lysine in position $X_{12}$, $X_{16}$, $X_{20}$, $X_{21}$, $X_{24}$, $X_{28}$, $X_{29}$ or $X_{30}$ of formula I,
wherein said substituent has the formula II:

$$Y_1\text{-}Y_2\text{-}Y_3\text{-}Y_4\text{-}Y_5\text{-}Y_6\text{-}Y_7\text{-}Y_8\text{-}Y_9\text{-}Y_{10}\text{-}Y_{11}\text{-}Y_{12}\text{-} \quad [II]$$

wherein $Y_1$ is hydrogen or represents a $C_{2-6}$ acyl group or a succinoyl moiety, and
wherein $Y_2$, $Y_3$, $Y_4$, $Y_5$, $Y_6$, $Y_7$, $Y_8$, $Y_9$, $Y_{10}$, $Y_{11}$ or $Y_{12}$ is individually absent or individually represents an amino acid residue selected from the group consisting of a Ser residue, an Ala residue, a Gly residue, formula i, formula ii, formula iii, formula iv and formula v:

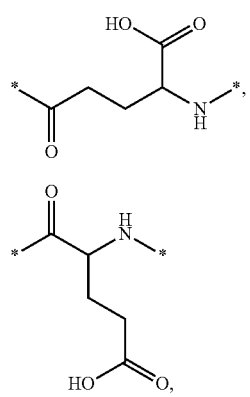

[i]

[ii]

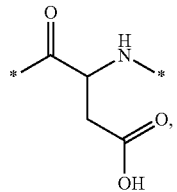

[iii]

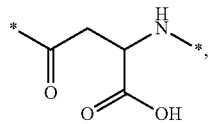

[iv]

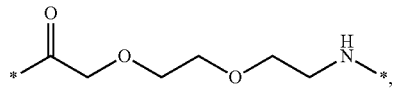

[v]

wherein formula i, ii, iii, and iv individually has the stereochemistry L or D, and provided that said substituent has three to ten negatively charged moieties, or a pharmaceutically acceptable salt, amide, or ester of said derivative.

2. A derivative according to any one of the preceding embodiments, wherein said glucagon analogue consists of formula I.

3. A derivative according to any one of the preceding embodiments, wherein said glucagon analogue or derivative comprises no amino acid residues added to the C-terminal of $X_{30}$.

4. The derivative according to any one of the preceding embodiments, wherein said derivative is a pharmaceutically acceptable salt, amide, or ester of said derivative.

5. The derivative according to any one of the preceding embodiments, wherein said glucagon analogue comprises 3-15 amino acid residue modifications, such as substitutions or additions, in said glucagon analogue as compared to glucagon (SEQ ID NO: 1).

6. The derivative according to any one of the preceding embodiments, wherein said derivative comprises up to 14, such as up to 13 or up to 12, amino acid residue modifications, such as substitutions or additions, in said glucagon analogue as compared to glucagon (SEQ ID NO: 1).

7. The derivative according to any one of the preceding embodiments, wherein said glucagon analogue comprises up to 11, such as up to 10 or up to 9, amino acid residue modifications, such as substitutions or additions, in said glucagon analogue as compared to glucagon (SEQ ID NO: 1).

8. The derivative according to any one of the preceding embodiments, wherein said glucagon analogue comprises up to 8, such as up to 7 or up to 6, amino acid residue modifications, such as substitutions or additions, in said glucagon analogue as compared to glucagon (SEQ ID NO: 1).

9. The derivative according to any one of the preceding embodiments, wherein $X_2$ is Ser.

10. The derivative according to any one of the preceding embodiments, wherein $X_{10}$ is Tyr.

11. The derivative according to any one of the preceding embodiments, wherein $X_{12}$ is Lys.

12. The derivative according to any one of the preceding embodiments, wherein $X_{15}$ is Asp.

13. The derivative according to any one of the preceding embodiments, wherein $X_{16}$ is Ser.

14. The derivative according to any one of the preceding embodiments, wherein $X_{20}$ is Gln.
15. The derivative according to any one of the preceding embodiments, wherein $X_{21}$ is Asp.
16. The derivative according to any one of the preceding embodiments, wherein $X_{24}$ is Gln.
17. The derivative according to any one of the preceding embodiments, wherein $X_{27}$ is Met.
18. The derivative according to any one of the preceding embodiments, wherein $X_{28}$ is Asn.
19. The derivative according to any one of the preceding embodiments, wherein $X_{29}$ is Thr.
20. The derivative according to any one of the preceding embodiments, wherein $X_{30}$ is absent.
21. The derivative according to any one of the preceding embodiments, wherein $X_2$ is Aib.
22. The derivative according to any one of the preceding embodiments, wherein $X_{10}$ is Leu.
23. The derivative according to any one of the preceding embodiments, wherein $X_{15}$ is Glu.
24. The derivative according to any one of the preceding embodiments, wherein $X_{16}$ is Leu.
25. The derivative according to any one of the preceding embodiments, wherein $X_{16}$ is Val.
26. The derivative according to any one of the preceding embodiments, wherein $X_{20}$ is Lys.
27. The derivative according to any one of the preceding embodiments, wherein $X_{21}$ is Glu.
28. The derivative according to any one of the preceding embodiments, wherein $X_{24}$ is Lys.
29. The derivative according to any one of the preceding embodiments, wherein $X_{24}$ is Ala.
30. The derivative according to any one of the preceding embodiments, wherein $X_{27}$ is Leu.
31. The derivative according to any one of the preceding embodiments, wherein $X_{28}$ is Ser.
32. The derivative according to any one of the preceding embodiments, wherein $X_{28}$ is Lys.
33. The derivative according to any one of the preceding embodiments, wherein $X_{29}$ is Lys.
34. The derivative according to any one of the preceding embodiments, wherein $Y_{12}$ is attached to said nitrogen atom of the side chain of a lysine in position $X_{12}$, $X_{16}$, $X_{20}$, $X_{21}$, $X_{24}$, $X_{28}$, $X_{29}$ or $X_{30}$ of said derivative.
35. The derivative according to any one of the preceding embodiments, wherein said substituent is covalently attached to the epsilon-nitrogen atom of the side chain of a lysine.
36. The derivative according to any one of the preceding embodiments, wherein said substituent is attached to a lysine in position $X_{12}$, $X_{16}$ or $X_{20}$.
37. The derivative according to any one of the preceding embodiments, wherein said substituent is attached to a lysine in position $X_{21}$, $X_{24}$ or $X_{28}$.
38. The derivative according to any one of the preceding embodiments, wherein said substituent is attached to a lysine in position $X_{29}$ or $X_{30}$.
39. The derivative according to any one of the preceding embodiments, wherein said substituent is attached to a lysine in position $X_{24}$.
40. The derivative according to any one of the preceding embodiments, wherein said substituent has 3, 4, 5, 6, 7, 8, 9 or 10 negatively charged moieties.
41. The derivative according to any one of the preceding embodiments, wherein said substituent comprises 3-10, such as 3-5 or 4, residues of formula i.
42. The derivative according to any one of the preceding embodiments, wherein $Y_1$ of said substituent is an acetyl group.
43. The derivative according to any one of the preceding embodiments, wherein said substituent is selected from the group of consisting of the moieties:

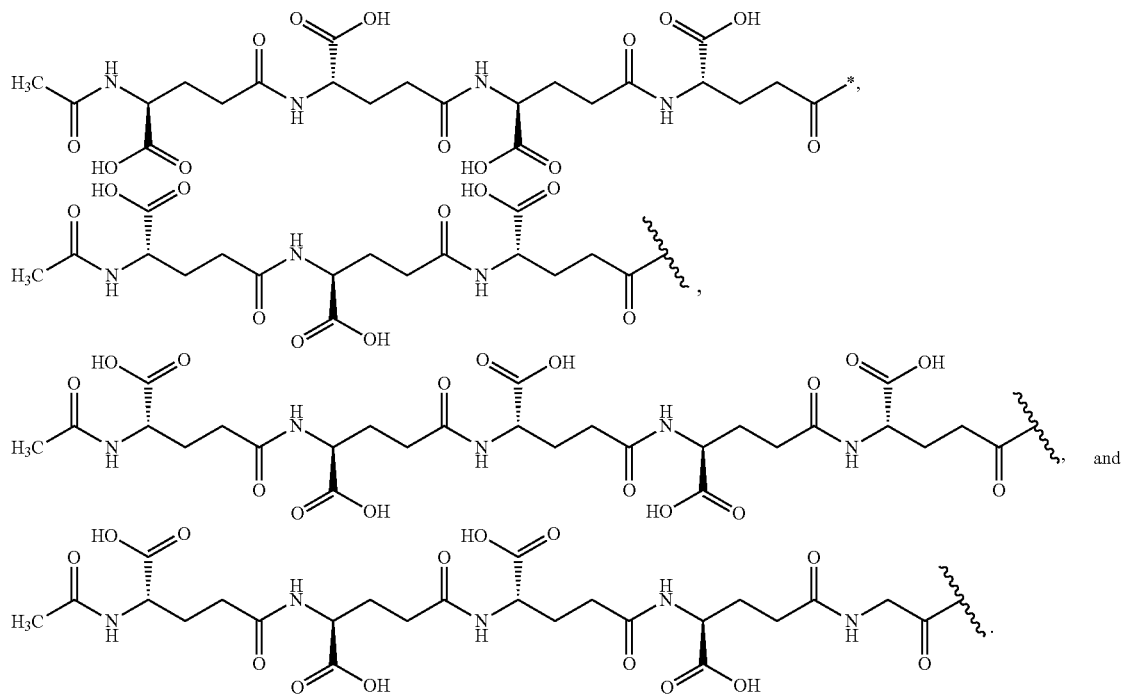

44. The derivative according to any one of the preceding embodiments, wherein said substituent is the moiety

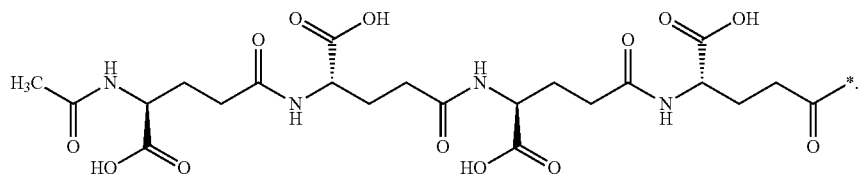

45. The derivative according to any one of the preceding embodiments, wherein said derivative is selected from the group consisting of
N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Leu16, Lys24, Leu27, Ser28]-Glucagon

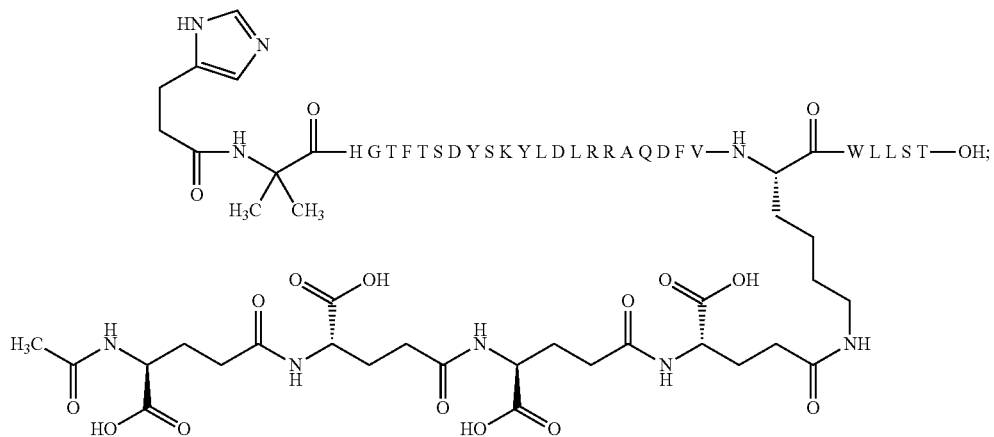

Chem. 1 (SEQ ID NO: 2)

N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Lys24, Leu27, Ser28]-Glucagon

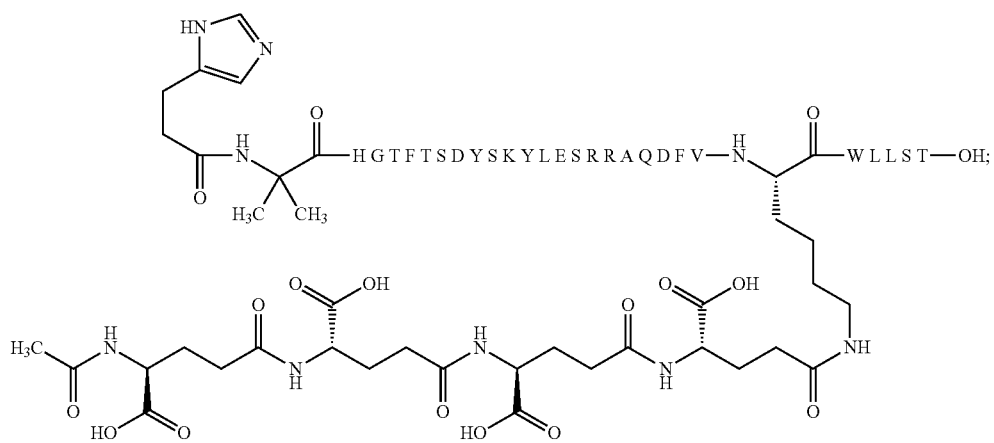

Chem. 2 (SEQ ID NO: 3)

N^ε24-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Leu10, Glu15, Lys24, Leu27, Ser28]-Glucagon Chem. 3 (SEQ ID NO: 4)

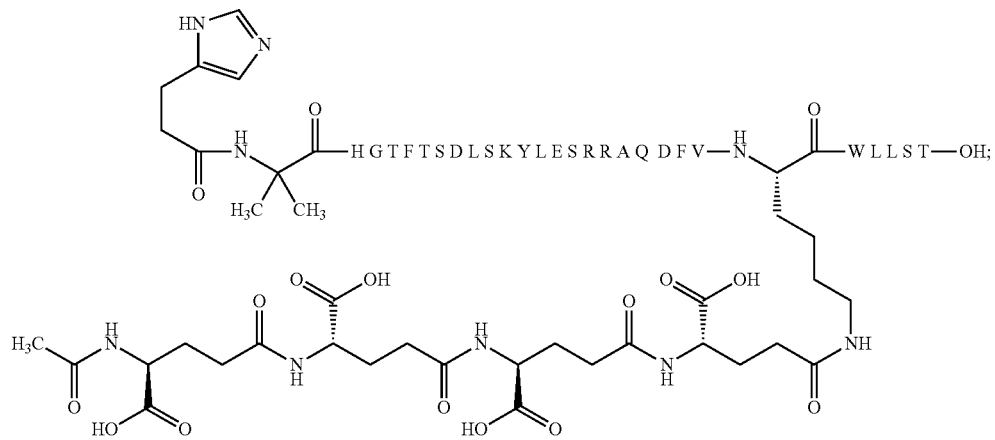

N^ε28-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Ala24, Leu27, Lys28]-Glucagon Chem. 4 (SEQ ID NO: 5)

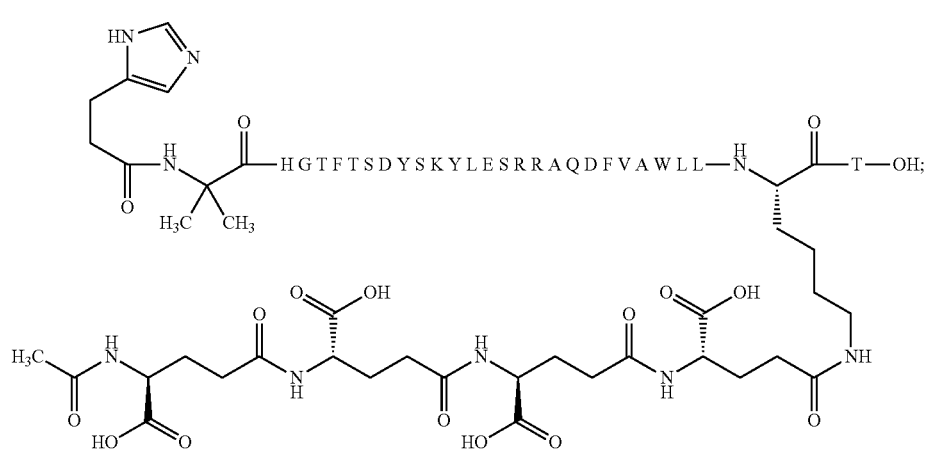

N^ε24-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys24, Leu27, Ser28]-Glucagon Chem. 5 (SEQ ID NO: 6)
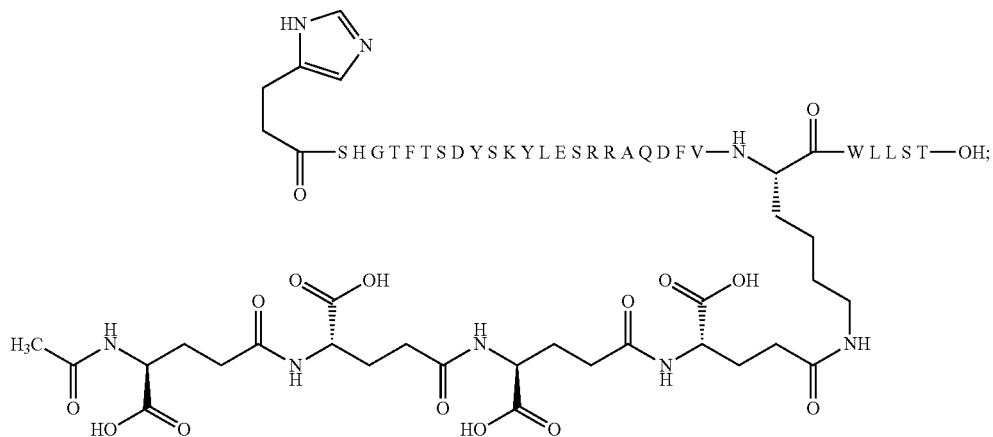
$N^{\varepsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Ser28]-Glucagon
Chem. 6 (SEQ ID NO: 7)
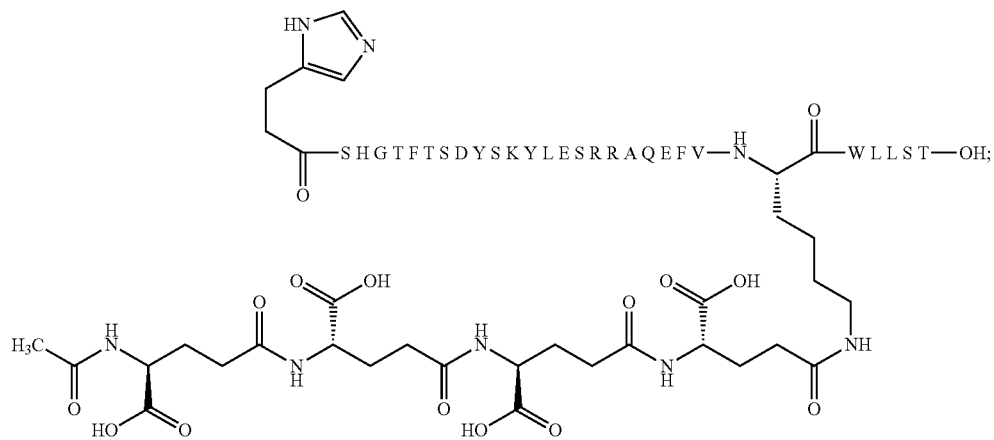
$N^{\varepsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Glu21, Lys24, Leu27, Ser28]-Glucagon Chem. 7 (SEQ ID NO: 8)
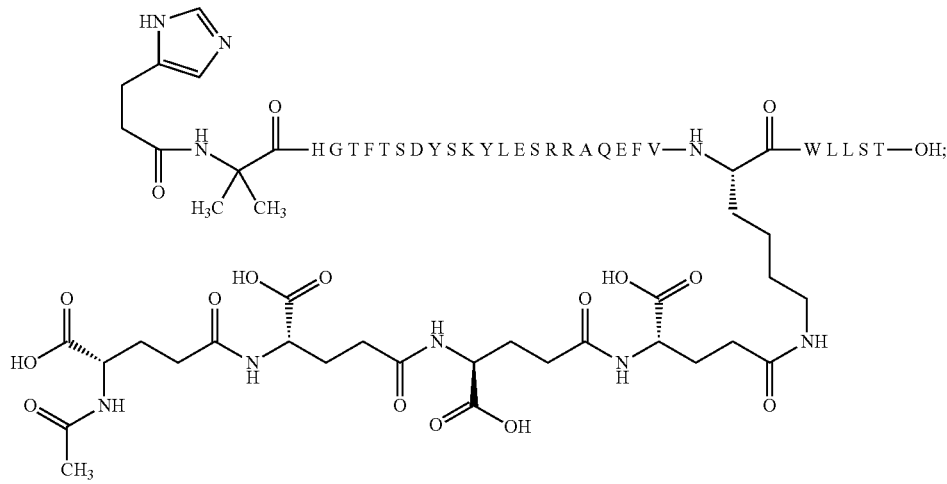
N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Leu16, Glu21, Lys24, Leu27, Ser28]-Glucagon
Chem. 8 (SEQ ID NO: 9)
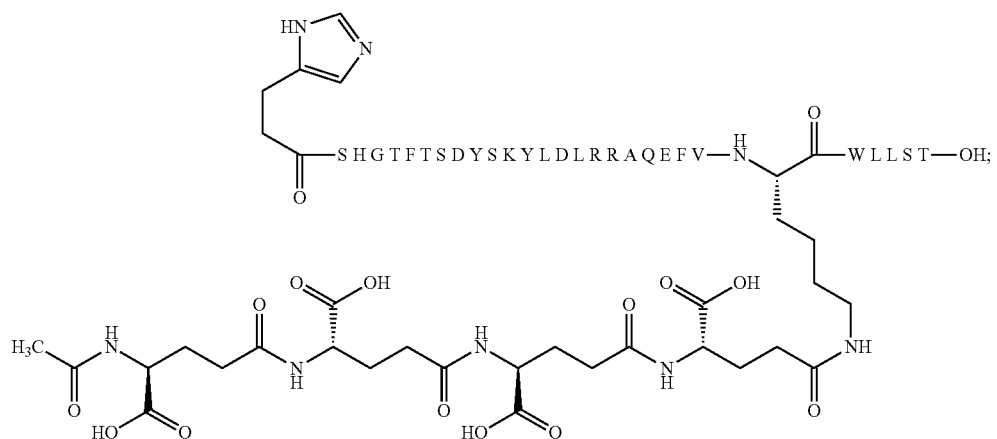
N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Leu16, Lys24, Leu27, Ser28]-Glucagon Chem. 9 (SEQ ID NO: 10)
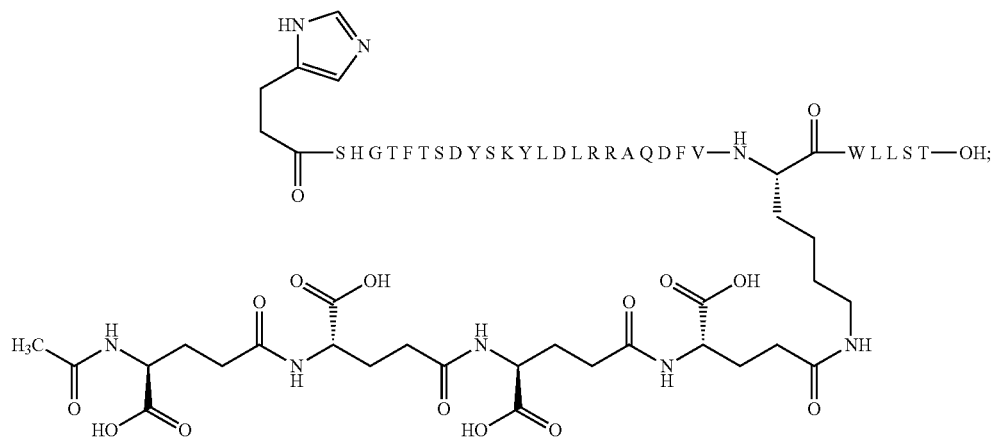
N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Val16, Lys24, Leu27, Ser28]-Glucagon
Chem. 10 (SEQ ID NO: 11)
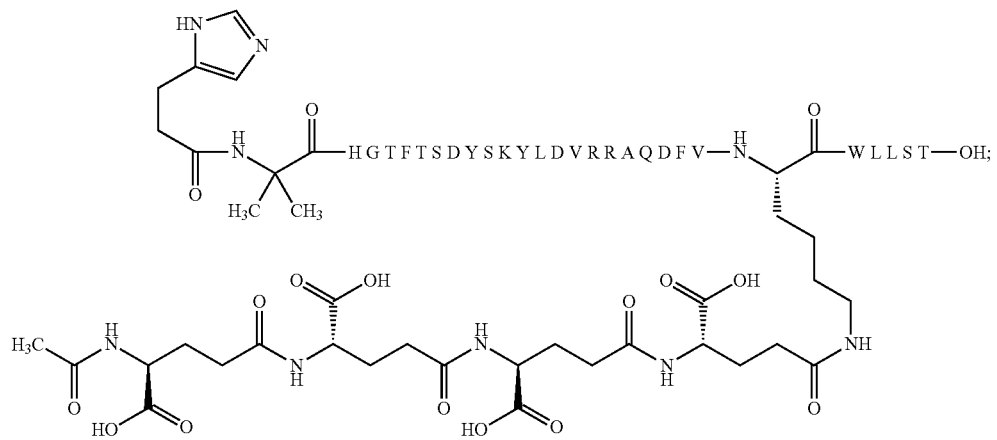
N$^{\epsilon 16}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys16, Glu21, Leu27, Ser28]-Glucagon Chem. 11 (SEQ ID NO: 12)
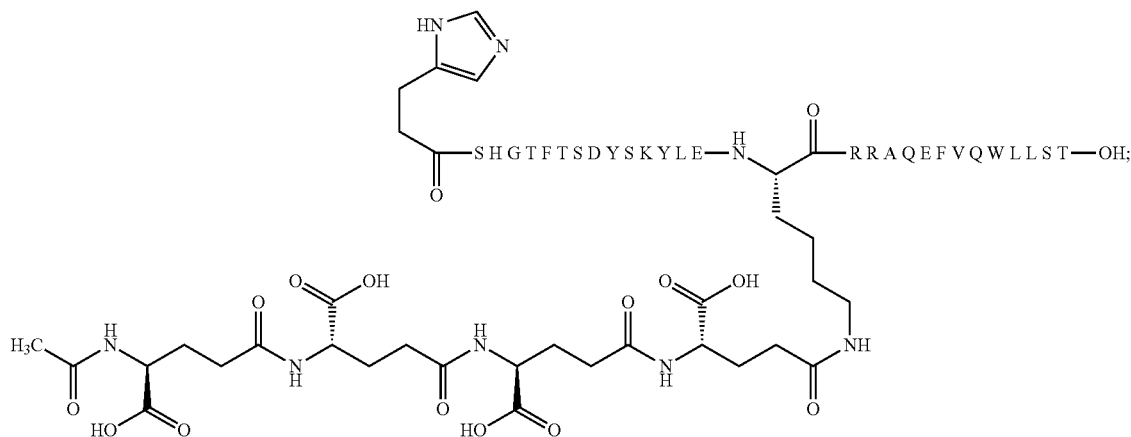
$N^{\epsilon 20}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys20, Glu21, Leu27, Ser28]-Glucagon
Chem. 12 (SEQ ID NO: 13)
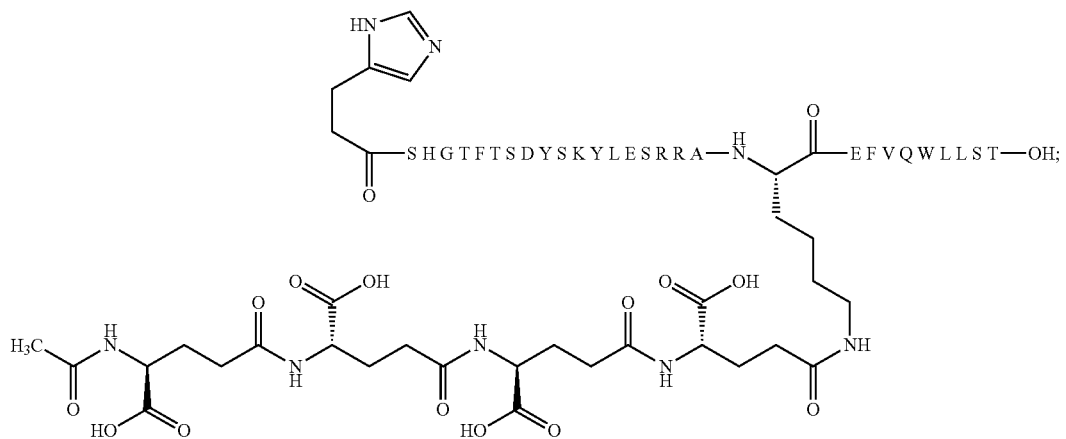
$N^{\epsilon 21}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys21, Leu27, Ser28]-Glucagon Chem. 13 (SEQ ID NO: 14)
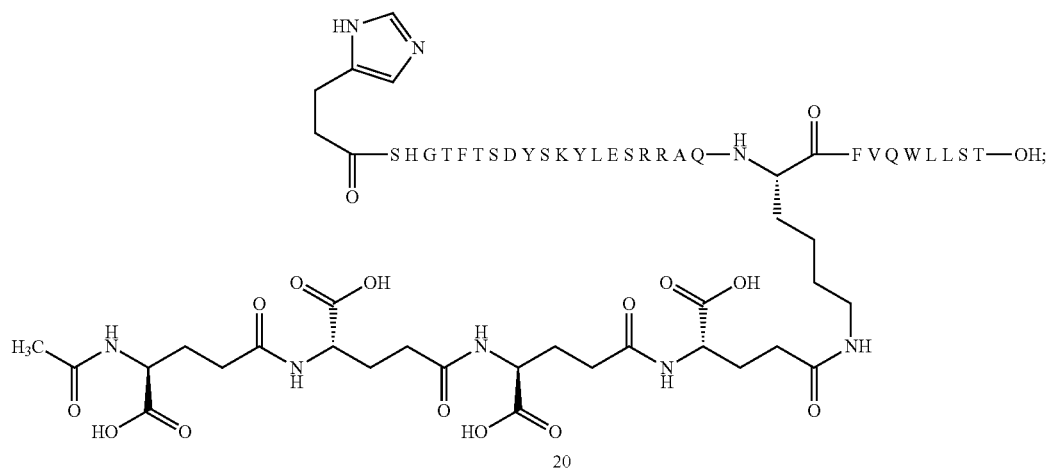
$N^{\varepsilon 28}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Leu27, Lys28]-Glucagon
Chem. 14 (SEQ ID NO: 15)
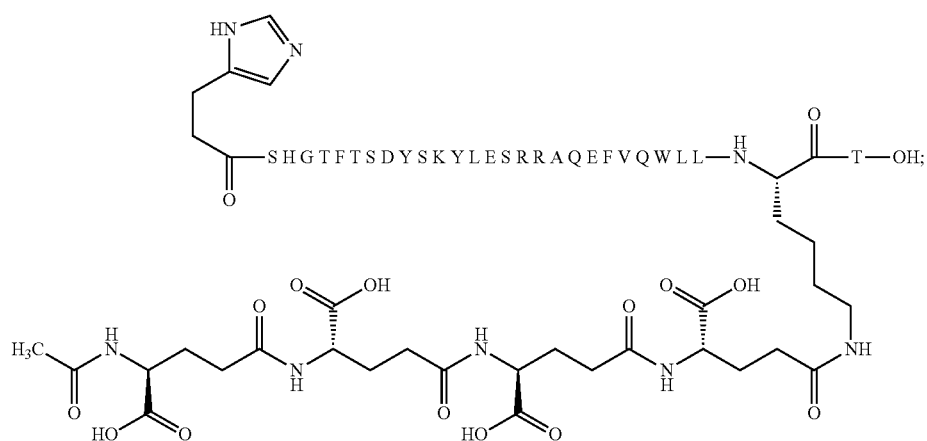
$N^{\varepsilon 29}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Leu27, Ser28, Lys29]-Glucagon
Chem. 15 (SEQ ID NO: 16)
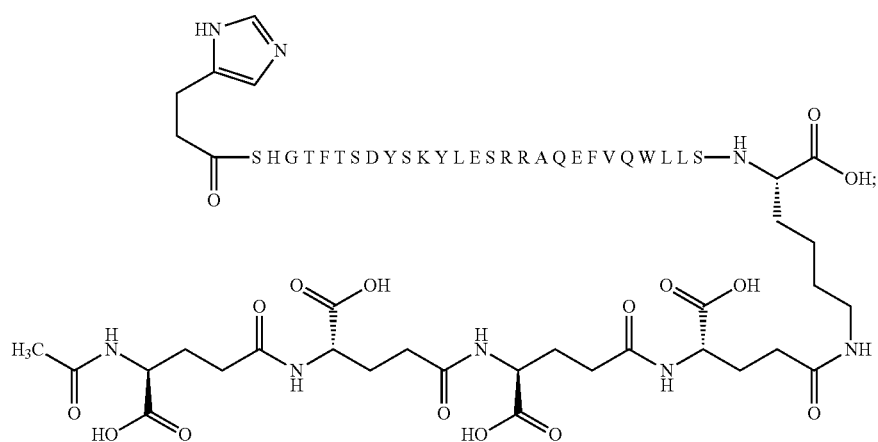

N$^\alpha$([Imp1, His3, Glu15, Glu21, Leu27, Ser28]-Glucagonyl)-N$^\epsilon$[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]Lys Chem. 16 (SEQ ID NO: 17)

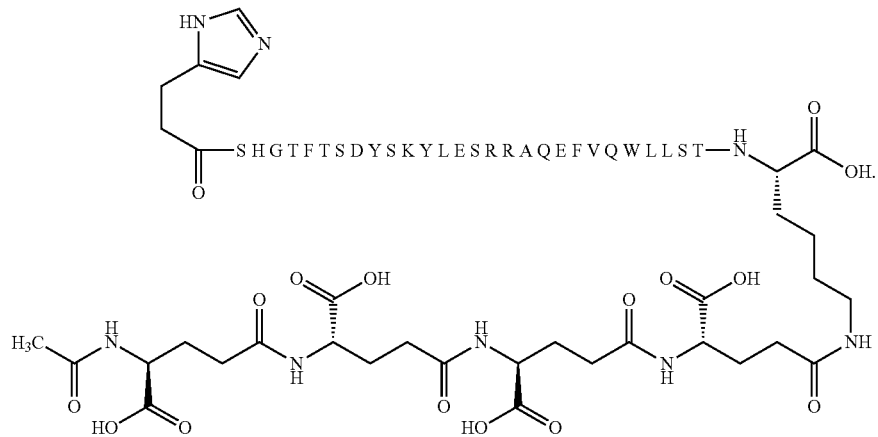

46. The derivative according to any one of the preceding embodiments, wherein said derivative is selected from the group consisting of
N$^{\epsilon 24}$-[2-[[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]amino]acetyl]-[Imp1, His3, Glu15, Glu21, Lys24, Leu27, Ser28]-Glucagon Chem. 17 (SEQ ID NO: 7)

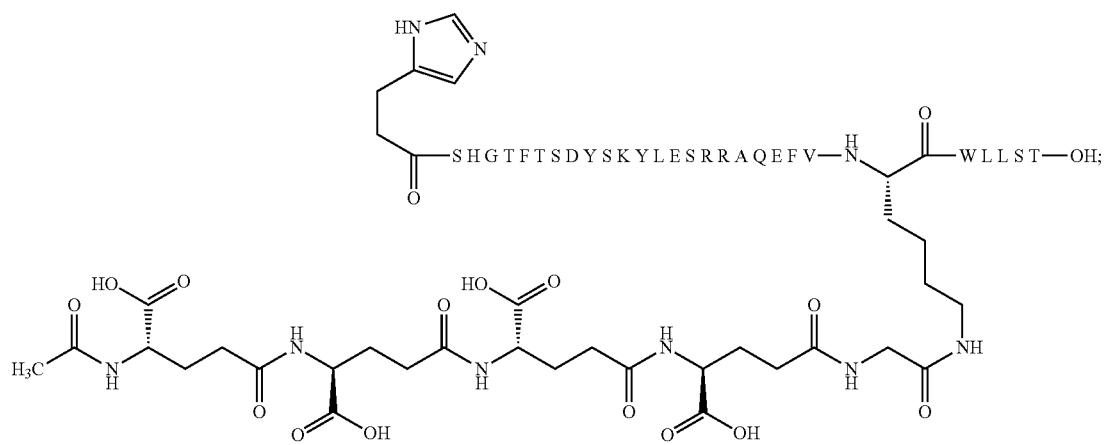

N$^{\epsilon 24}$-[(4S)-4-[[(4S)-4-[[(4S)-4-acetamido-4-carboxybutanoyl]amino]-4-carboxybutanoyl]amino]-4-carboxybutanoyl]-[Imp1, His3, Glu15, Glu21, Lys24, Leu27, Ser28]-Glucagon Chem. 18 (SEQ ID NO: 7)
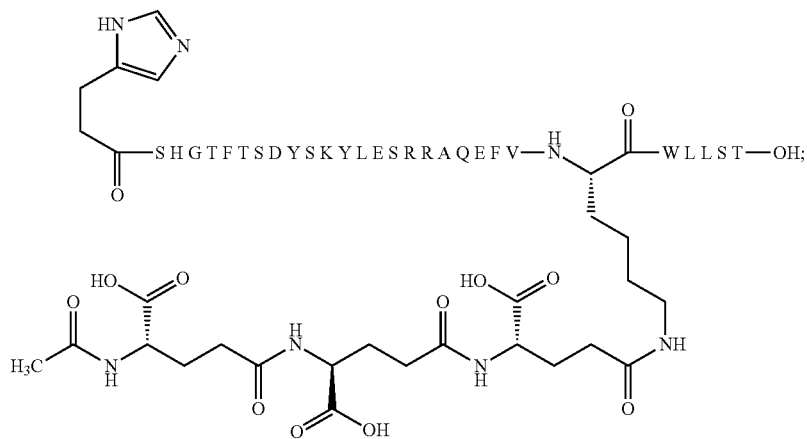
$N^{\epsilon 24}$-[(4S)-4-[[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Ser28]-Glucagon
Chem. 19 (SEQ ID NO: 7)
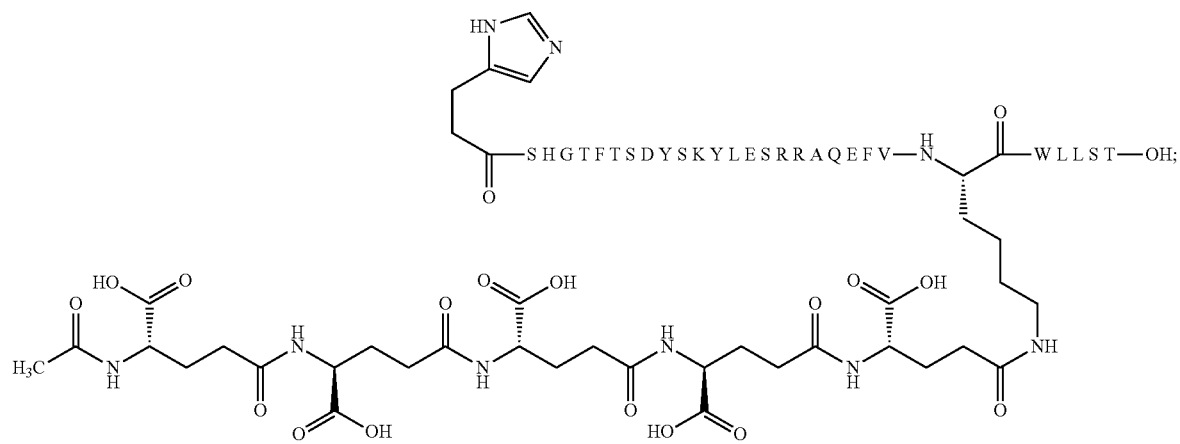
$N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Ala16, Lys24, Leu27, Ser28]-Glucagon Chem. 20 (SEQ ID NO: 18)
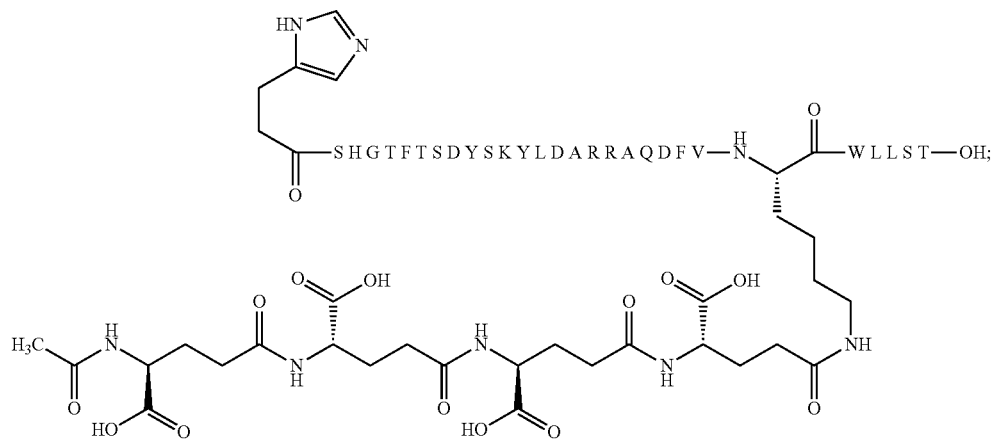
$N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Aib16, Lys24, Leu27, Ser28]-Glucagon
Chem. 21 (SEQ IS NO: 19)
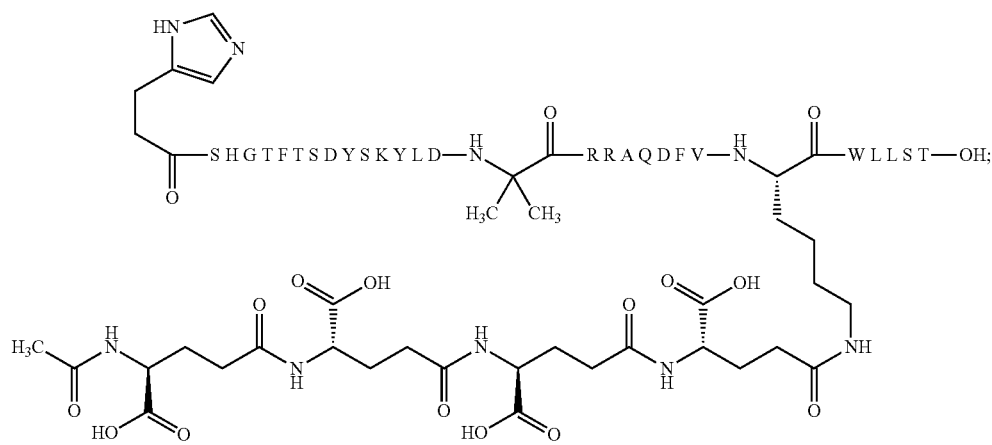
and
$N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Glu28]-Glucagon
Chem. 22 (SEQ ID NO: 20)
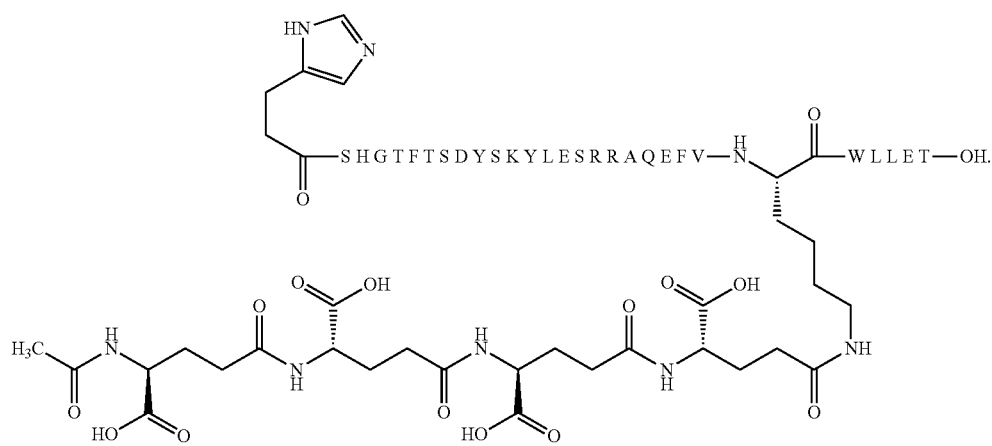

47. The derivative according to any one of the preceding embodiments, wherein said glucagon analogue does not comprise a C-terminal amide.
48. The derivative according to any one of the preceding embodiments, wherein said derivative is an agonist of the glucagon receptor, with an EC50 of no more than 200 pM.
49. The derivative according to any one of the preceding embodiments, wherein said derivative has more than 70% recovery in a ThT fibrillation assay, such as Assay (III) described herein.
50. The derivative according to any one of the preceding embodiments, wherein said derivative has more than 7 hours lag time in a ThT fibrillation assay, such Assay (III) described herein.
51. The derivative according to any one of the preceding embodiments, wherein said derivative has a chemical degradation of less than 5% as determined by Assay (IV) described herein.
52. The derivative according to any one of the preceding embodiments, wherein said derivative has a solubility of at least 0.1 mmol/l.
53. The derivative according to any one of the preceding embodiments, wherein said solubility may be determined in a composition comprising said derivative in 10 mM phosphate buffer at a pH in the range of 7.4-8.2.
54. The derivative according to any one of the preceding embodiments, wherein said derivative has a ratio between its EC50 potency on the GLP-1 receptor and its EC50 potency on the glucagon receptor of at least 50, wherein said potencies may be determined using Assay (I)(a) and Assay (I)(b) described herein.
55. An intermediate product in the form of a glucagon analogue which comprises the following modifications as compared to glucagon (SEQ ID NO: 1):
(i) [Imp1, Aib2, His3, Leu16, Lys24, Leu27, Ser28]-Glucagon;
(ii) [Imp1, Aib2, His3, Glu15, Lys24, Leu27, Ser28]-Glucagon;
(iii) [Imp1, Aib2, His3, Leu10, Glu15, Lys24, Leu27, Ser28]-Glucagon;
(iv) [Imp1, Aib2, His3, Glu15, Ala24, Leu27, Lys28]-Glucagon;
(v) [Imp1, His3, Glu15, Lys24, Leu27, Ser28]-Glucagon;
(vi) [Imp1, His3, Glu15, Glu21, Lys24, Leu27, Ser28]-Glucagon;
(vii) [Imp1, Aib2, His3, Glu15, Glu21, Lys24, Leu27, Ser28]-Glucagon;
(viii) [Imp1, His3, Leu16, Glu21, Lys24, Leu27, Ser28]-Glucagon;
(ix) [Imp1, His3, Leu16, Lys24, Leu27, Ser28]-Glucagon;
(x) [Imp1, Aib2, His3, Val16, Lys24, Leu27, Ser28]-Glucagon;
(xi) [Imp1, His3, Glu15, Lys16, Glu21, Leu27, Ser28]-Glucagon;
(xii) [Imp1, His3, Glu15, Lys20, Glu21, Leu27, Ser28]-Glucagon;
(xiii) [Imp1, His3, Glu15, Lys21, Leu27, Ser28]-Glucagon;
(xiv) [Imp1, His3, Glu15, Glu21, Leu27, Lys28]-Glucagon;
(xv) [Imp1, His3, Glu15, Glu21, Leu27, Ser28, Lys29]-Glucagon;
(xvi) [Imp1, His3, Glu15, Glu21, Leu27, Ser28, Lys30]-Glucagon;
or a pharmaceutically acceptable salt, amide, or ester thereof.
56. An intermediate product in the form of a glucagon analogue which comprises the following modifications as compared to glucagon (SEQ ID NO: 1):
(xvii) [Imp1, His3, Ala16, Lys24, Leu27, Ser28]-Glucagon;
(xviii) [Imp1, His3, Aib16, Lys24, Leu27, Ser28]-Glucagon;
(xix) [Imp1, His3, Glu15, Glu21, Lys24, Leu27, Glu28]-Glucagon;
or a pharmaceutically acceptable salt, amide, or ester thereof.
57. The intermediate product according to any one of the preceding embodiments, wherein the glucagon analogue is selected from the following analogues of glucagon (SEQ ID NO: 1):
(i-a) [Imp1, Aib2, His3, Leu16, Lys24, Leu27, Ser28]-Glucagon;
(ii-a) [Imp1, Aib2, His3, Glu15, Lys24, Leu27, Ser28]-Glucagon;
(iii-a) [Imp1, Aib2, His3, Leu10, Glu15, Lys24, Leu27, Ser28]-Glucagon;
(iv-a) [Imp1, Aib2, His3, Glu15, Ala24, Leu27, Lys28]-Glucagon;
(v-a) [Imp1, His3, Glu15, Lys24, Leu27, Ser28]-Glucagon;
(vi-a) [Imp1, His3, Glu15, Glu21, Lys24, Leu27, Ser28]-Glucagon;
(vii-a) [Imp1, Aib2, His3, Glu15, Glu21, Lys24, Leu27, Ser28]-Glucagon;
(viii-a) [Imp1, His3, Leu16, Glu21, Lys24, Leu27, Ser28]-Glucagon;
(ix-a) [Imp1, His3, Leu16, Lys24, Leu27, Ser28]-Glucagon;
(x-a) [Imp1, Aib2, His3, Val16, Lys24, Leu27, Ser28]-Glucagon;
(xi-a) [Imp1, His3, Glu15, Lys16, Glu21, Leu27, Ser28]-Glucagon;
(xii-a) [Imp1, His3, Glu15, Lys20, Glu21, Leu27, Ser28]-Glucagon;
(xiii-a) [Imp1, His3, Glu15, Lys21, Leu27, Ser28]-Glucagon;
(xiv-a) [Imp1, His3, Glu15, Glu21, Leu27, Lys28]-Glucagon;
(xv-a) [Imp1, His3, Glu15, Glu21, Leu27, Ser28, Lys29]-Glucagon;
(xvi-a) [Imp1, His3, Glu15, Glu21, Leu27, Ser28, Lys30]-Glucagon;
or a pharmaceutically acceptable salt, amide, or ester thereof.
58. The intermediate product according to any one of the preceding embodiments, wherein the glucagon analogue is selected from the following analogues of glucagon (SEQ ID NO: 1):
(xvii) [Imp1, His3, Ala16, Lys24, Leu27, Ser28]-Glucagon;
(xviii) [Imp1, His3, Aib16, Lys24, Leu27, Ser28]-Glucagon;
(xix) [Imp1, His3, Glu15, Glu21, Lys24, Leu27, Glu28]-Glucagon;
or a pharmaceutically acceptable salt, amide, or ester thereof.
59. A composition comprising the derivative as defined in any one of the preceding embodiments and one or more pharmaceutically acceptable excipients.
60. A derivative as defined in any one of the preceding embodiments for use in medicine.
61. The derivative according to embodiment 60 for use in treating and/or preventing hypoglycaemia.
62. A method for treating and/or preventing hypoglycaemia comprising administering a therapeutically effective amount of the derivative as defined in any one of the preceding embodiments to a patient in need thereof.

EXAMPLES

The invention is further illustrated with reference to the following examples, which are not intended to be in any way limiting to the scope of the invention as claimed.

LIST OF ABBREVIATIONS

BOC: tert-Butyl oxycarbonyl
DCM: Dichloromethane
DIC: Diisopropylcarbodiimide
Fmoc: 9-fluorenylmethyloxycarbonyl
HOAt: 1-hydroxy-7-azabenzotriazole
HPLC: High Performance Liquid Chromatography
LCMS: Liquid Chromatography Mass Spectroscopy
MeCN: Acetonitrile
Min: Minutes
Mtt: 4-Methyltrityl
NMP: N-methyl pyrrolidone
Oxyma Pure: Cyano-hydroxyimino-acetic acid ethyl ester
RP: Reverse Phase
RP-HPLC: Reverse Phase High Performance Liquid Chromatography
RT: Room Temperature
Rt: Retention time
SPPS: Solid Phase Peptide Synthesis
TFA: Trifluoroacetic acid
TIPS: Triisopropylsilane
UPLC: Ultra Performance Liquid Chromatography
10EE: 10 to the power (e.g. "10EE(X)" refers to the number 10 to the power (X), or simply the number $10^{(X)}$, i.e. $5\times10EE3$ is $5\times10^3$)

General Methods

This section relates to methods for synthesising resin bound peptide (SPPS methods, including methods for de-protection of amino acids, methods for cleaving the peptide from the resin, and for its purification), as well as methods for detecting and characterising the resulting peptide (LCMS and UPLC methods).

SPPS General Methods

This section relates to methods for solid phase peptide synthesis (SPPS methods, including methods for de-protection of amino acids, methods for cleaving the peptide from the resin, and for its purification), as well as methods for detecting and characterising the resulting peptide (LCMS and UPLC methods). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids were used. The N-terminal Imp was incorporated using 3-(N-1-Trityl-imidazol-4-yl)-propionic acid.

All operations in this section "SPPS general methods" stated below were performed at 100-µmol synthesis scale.

A suitable resin for the preparation of C-terminal carboxylic acids was a Wang resin preloaded with an amino acid such as Fmoc-Thr(tBu)-Wang resin (Low Load, 0.35 mmol/g). In cases where the substituent was attached to the C-terminal lysine, a suitable resin was a pre-loaded fmoc-Lys(Mtt)-Wang.

SPPS was performed on a Prelude Solid Phase Peptide Synthesizer from Protein Technologies (Tucson, Ariz. 85714 U.S.A.) at 100-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 20% piperidine in NMP. Coupling was performed using 3:3:3:4 amino acid/Oxyma Pure®/DIC/collidine in NMP. NMP and DCM top washes (2×2 each) were performed between deprotection and coupling steps. Coupling times were generally 60 or 120 minutes. Some amino acids were "double coupled", meaning that after the first coupling, the resin was drained and more reagents were added (amino acid, (HOAt or Oxyma Pure®), DIC, and collidine), and the mixture allowed to react again.

Attachment of the Substituent to Resin Bound Protected Peptide Backbone

The epsilon amino group of the lysine to be acylated was protected with Mtt. Mtt-deprotection was performed by treatment with hexafluoroisopropanol/DCM (75:25, 5×20 ml, each 10 min) followed by washings as described above in the section "SPPS general methods".

The chemical modification of the lysine was performed by one or more automated steps on the Prelude peptide synthesiser using Fmoc-Glu-OtBu or building blocks as described above. Double couplings were performed with 120 minutes reaction time per coupling. Acetylation was achieved using acetic anhydride.

Cleavage from the Resin

After synthesis the resin was washed with DCM, and the peptide was cleaved from the resin by a 2-3 hour treatment with TFA/TIS/water (95/2.5/2.5) followed by precipitation with diethylether. The precipitate was washed with diethylether.

Purification and Quantification

The crude peptide was dissolved in a suitable mixture of water and MeCN, such as water/MeCN (9:1), and purified by reversed-phase preparative HPLC (Waters Deltaprep 4000 or Gilson) on a column containing C18-silica gel. Elution was performed with an increasing gradient of MeCN in water containing 0.1% TFA. Relevant fractions were checked by analytical HPLC or UPLC. Fractions containing the pure target peptide were mixed and concentrated under reduced pressure. The resulting solution was analyzed (HPLC, LCMS) and the product was quantified using a chemiluminescent nitrogen specific HPLC detector (Antek 8060 HPLC-CLND) or by measuring UV-absorption at 280 nm. The product was dispensed into glass vials. The vials were capped with Millipore glassfibre prefilters. Freeze-drying afforded the peptide trifluoroacetate as a white solid.

Methods for Detection and Characterization

| Method: LCMS01 | |
|---|---|
| System | LC-system: Waters Acquity UPLC<br>Column:: Waters Acquity UPLC BEH, C-18, 1.7 µm, 2.1 mm × 50 mm<br>Detector:: Waters (Micromass) LCT Premier XE |

| Method: LCMS01 | |
|---|---|
| Detector setup | Ionisation method: ES<br>Scanning range: 500-2000 amu<br>Operating mode: W mode<br>positive/negative: positive mode<br>Cone Voltage: 50 V<br>Scantime 1<br>Interscandelay: 0.0 |
| Conditions | Linear gradient: 5% to 95% B<br>Gradient run-time: 4.0 minutes<br>Total run-time: 7.0 minutes<br>Flow rate: 0.4 mL/min<br>Column temperature: 40° C. |
| Eluents | Solvent A: 99.90% MQ-water, 0.1% formic acid<br>Solvent B: 99.90% acetonitrile, 0.1% formic acid<br>Solvent C: NA |
| Results specification and validation | Mass found is the mass found of the compound<br>M/z found is the molecular ion found ((M + z)/z) of the compound<br>Calculated Mass is the molecular weight of the desired compound<br>Calculated M/z is the molecular weight (M + z)/z of the desired compound |

| Method: UPLC01 | |
|---|---|
| System | System: Waters Acquity UPLC system<br>Column: ACQUITY UPLC BEH C18, 1.7 um, 2.1 mm × 150 mm column<br>Detectors: Waters Acquity TUV Detector |
| Detector setup | 214 nm and 254 nm |
| Conditions | Linear gradient: 5% to 60% B<br>Gradient run-time: 16 minutes<br>Total run-time: 20 minutes<br>Flow rate: 0.40 mL/min fixed<br>Column temperature: 40° C. |
| Eluents | Solvent A: 99.95% Water, 0.05% Trifluoroacetic acid<br>Solvent B: 99.95% Acetonitrile, 0.05% Trifluoroacetic acid |

| Method: UPLC02 | |
|---|---|
| System | System: Waters Acquity UPLC system<br>Column: ACQUITY UPLC BEH C18, 1.7 um, 2.1 mm × 150 mm column<br>Detectors: Waters Acquity TUV Detector |
| Detector setup | 214 nm and 254 nm |
| Conditions | Linear gradient: 5% to 95% B<br>Gradient run-time: 16 minutes<br>Flow rate: 0.40 mL/min fixed<br>Column temperature: 40° C. |
| Eluents | Solvent A: 99.95% Water, 0.05% Trifluoroacetic acid<br>Solvent B: 99.95% Acetonitrile, 0.05% Trifluoroacetic acid |

Example 1

$N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Leu16, Lys24, Leu27, Ser28]-Glucagon

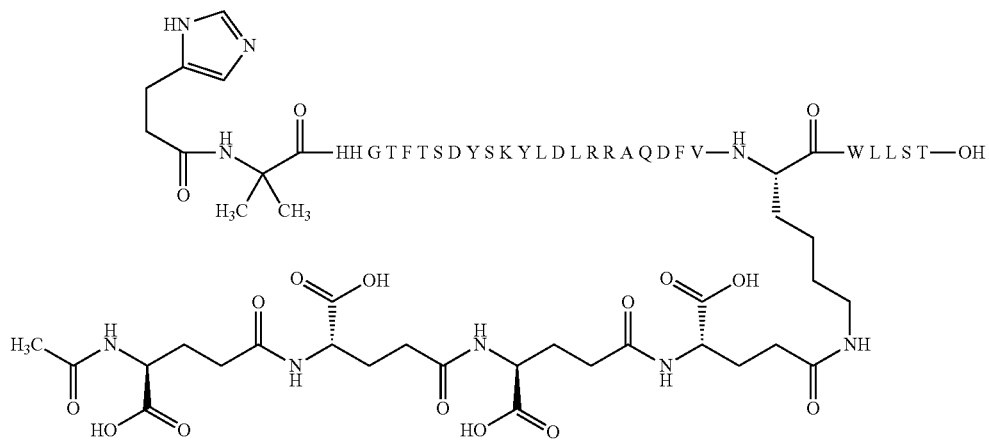

Chem. 1 (SEQ ID NO: 2)

UPLC01: Rt=10.2 min
LCMS01: Rt=1.99 min; Calc m/z=4014.3. Found m/3=1339. Found m/4=1004. Found m/5=803.

Example 2

N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Lys24, Leu27, Ser28]-Glucagon Chem. 2 (SEQ ID NO: 3)

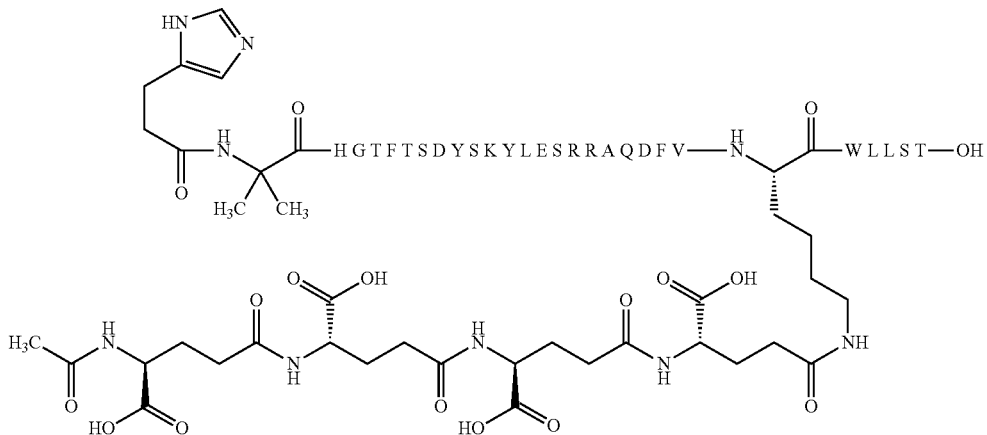

UPLC02: Rt=6.3 min
LCMS01: Rt=1.75 min; Calc m/z=4002.3. Found m/3=1335. Found m/4=1001. Found m/5=801.

Example 3

N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Leu10, Glu15, Lys24, Leu27, Ser28]-Glucagon Chem. 3 (SEQ ID NO: 4)

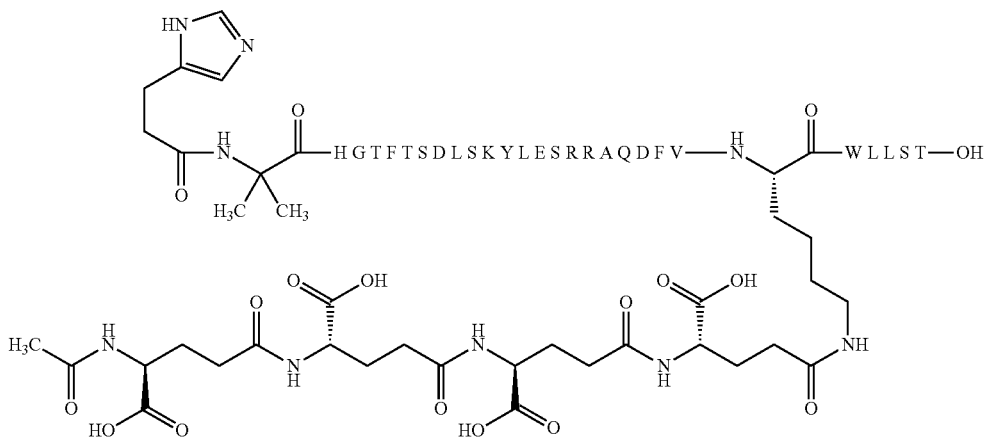

UPLC02: Rt=6.7 min
LCMS01: Rt=1.8 min. Found m/1=3952.3. Found m/3=1318. Found m/4=989. Found m/5=791.

Example 4

$N^{\epsilon 28}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Ala24, Leu27, Lys28]-Glucagon

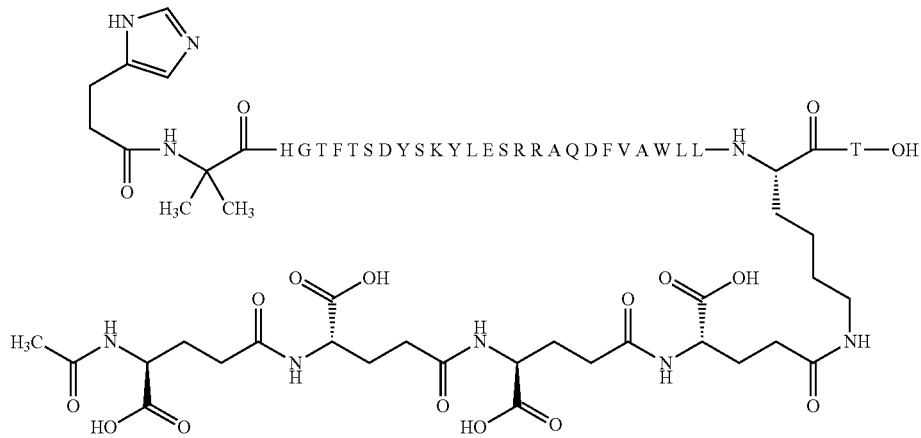

Chem. 4 (SEQ ID NO: 5)

UPLC02: Rt=6.2 min
LCMS01: Rt=1.7 min; Calc m/z=3986.3. Found m/3=1329. Found m/4=997. Found m/5=798.

Example 5

$N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys24, Leu27, Ser28]-Glucagon

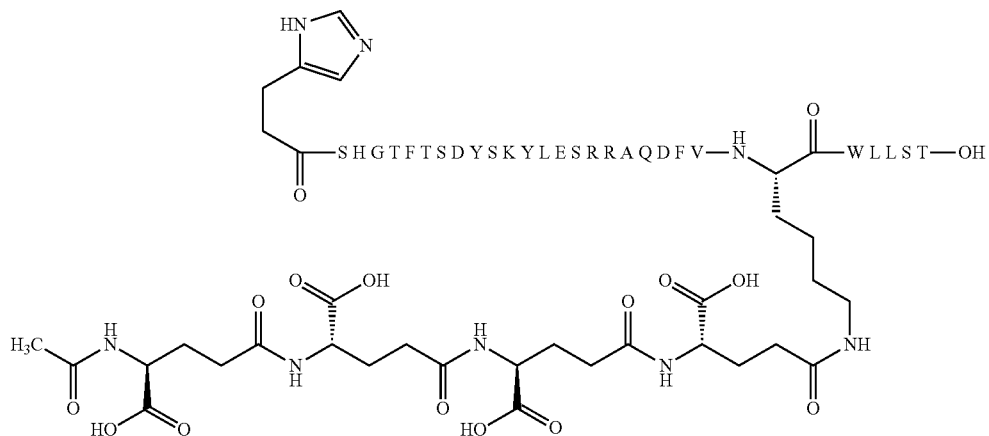

Chem. 5 (SEQ ID NO: 6)

UPLC01: Rt=9.2 min
LCMS01: Rt=1.8 min; Calc m/z=4004.2. Found m/3=1336. Found m/4=1002. Found m/5=801.

Example 6

N^ε24-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Ser28]-Glucagon Chem. 6 (SEQ ID NO: 7)

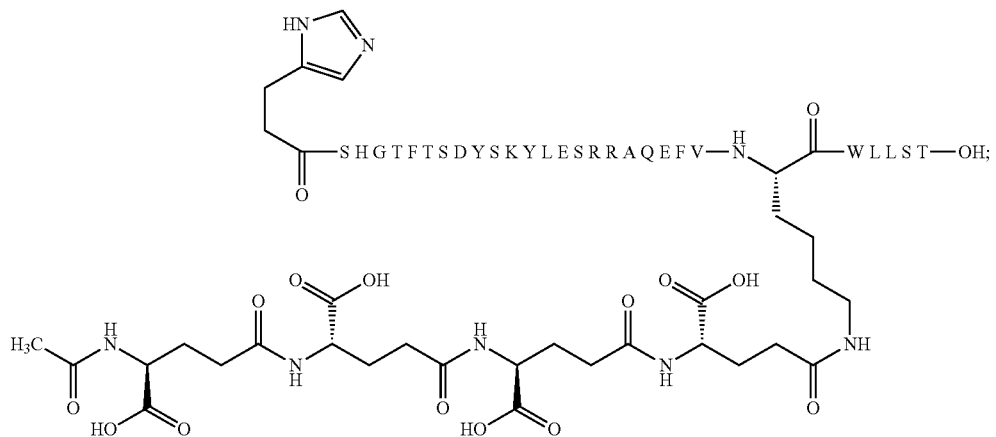

UPLC01: Rt=9.4 min
LCMS01: Rt=1.82 min; Calc m/z=4018.3. Found m/3=1340. Found m/4=1005. Found m/5=804.

Example 7

N^ε24-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Glu15, Glu21, Lys24, Leu27, Ser28]-Glucagon Chem. 7 (SEQ ID NO: 8)

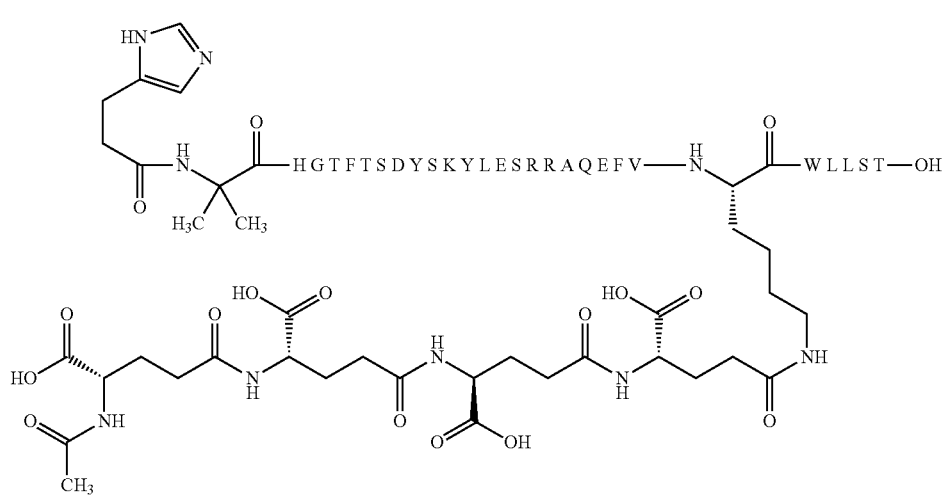

UPLC02: Rt=6.4 min
LCMS01: Rt=1.7 min; Calc m/z=4016.3. Found m/3=1339. Found m/4=1005. Found m/5=804.

Example 8

N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Leu16, Glu21, Lys24, Leu27, Ser28]-Glucagon Chem. 8 (SEQ ID NO: 9)

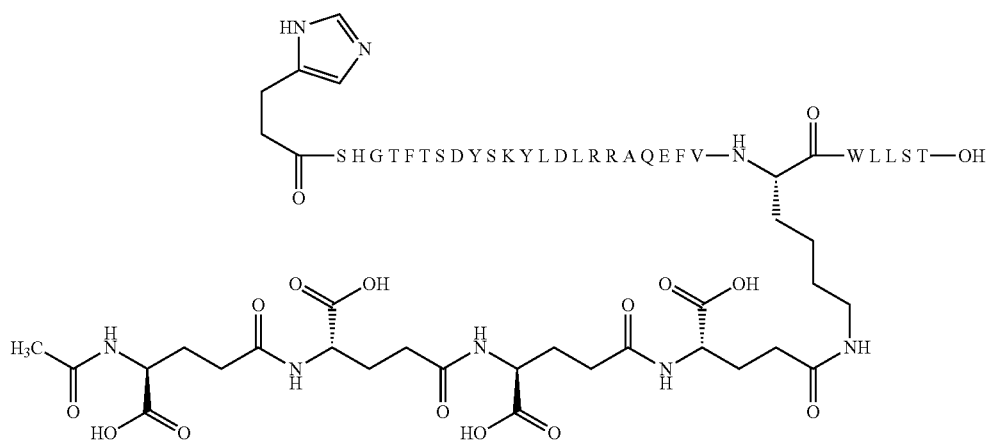

UPLC01: Rt=10.8 min
LCMS01: Rt=1.9 min; Calc m/z=4030.3. Found m/3=1344. Found m/4=1008. Found m/5=807.

Example 9

N$^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Leu16, Lys24, Leu27, Ser28]-Glucagon Chem. 9 (SEQ ID NO: 10)

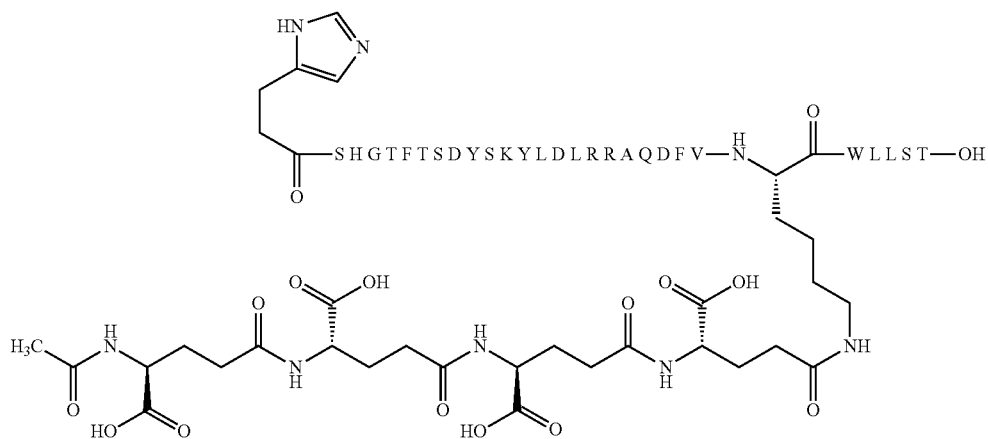

UPLC01: Rt=10.5 min
LCMS01: Rt=1.9 min; Calc m/z=4016.3. Found m/3=1340. Found m/4=1005. Found m/5=804.

Example 10

N$^{\epsilon24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, Aib2, His3, Val16, Lys24, Leu27, Ser28]-Glucagon Chem. 10 (SEQ ID NO: 11)

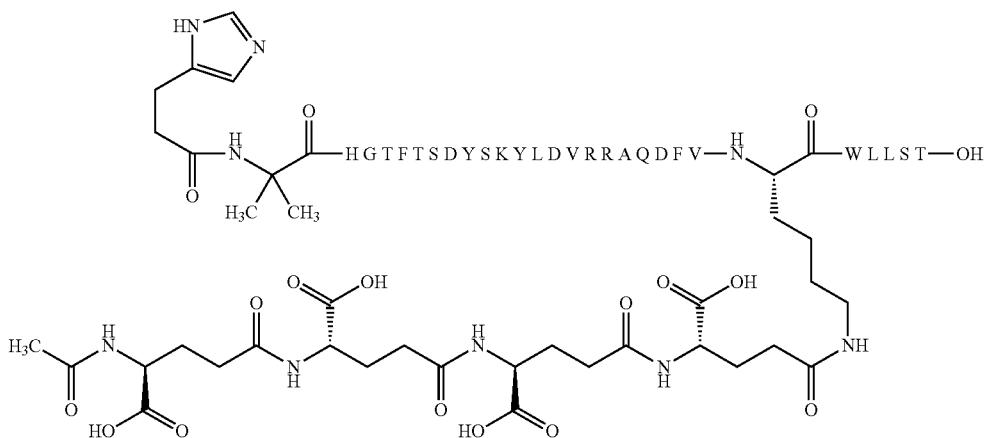

UPLC01: Rt=10.3 min
LCMS01: Rt=1.9 min; Calc m/z=4000.3. Found m/3=1334. Found m/4=1001. Found m/5=801.

Example 11

N$^{\epsilon16}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys16, Glu21, Leu27, Ser28]-Glucagon Chem. 11 (SEQ ID NO: 12)

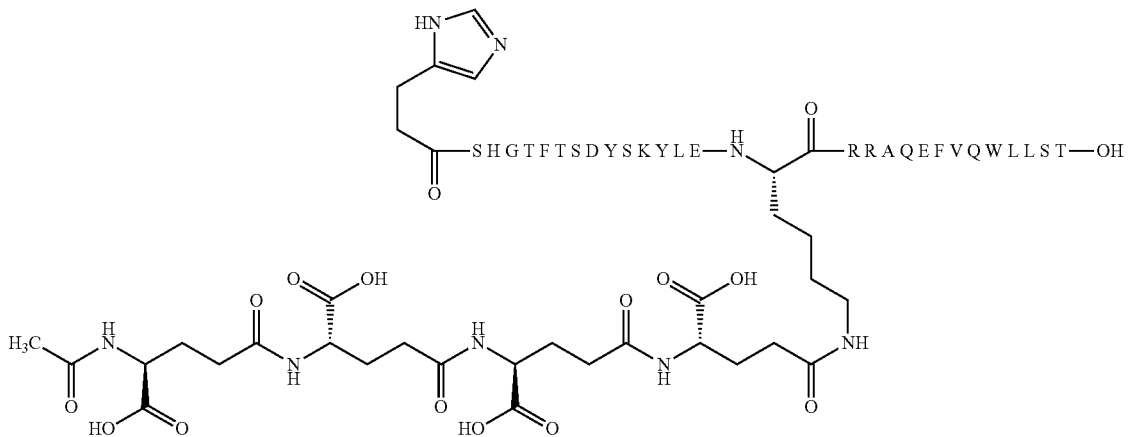

UPLC02: Rt=6.4 min
LCMS01: Rt=3.1 min; Calc m/z=4059.3. Found m/3=1354. Found m/4=1015. Found m/5=812.

Example 12

$N^{\epsilon 20}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys20, Glu21, Leu27, Ser28]-Glucagon Chem. 12 (SEQ ID NO: 13)

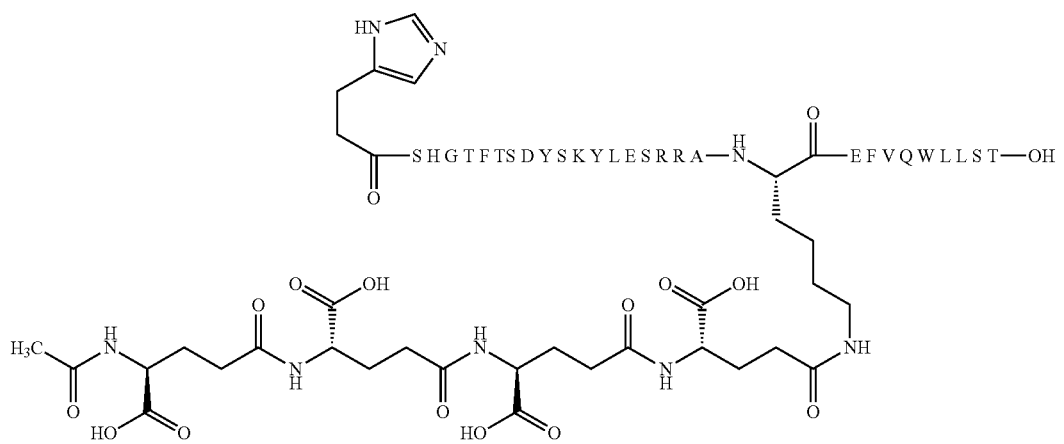

UPLC02: Rt=6.4 min
LCMS01: Rt=3.2 min; Calc m/z=4018.3. Found m/3=1340. Found m/4=1005. Found m/5=804.

Example 13

$N^{\epsilon 21}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Lys21, Leu27, Ser28]-Glucagon Chem. 13 (SEQ ID NO: 14)

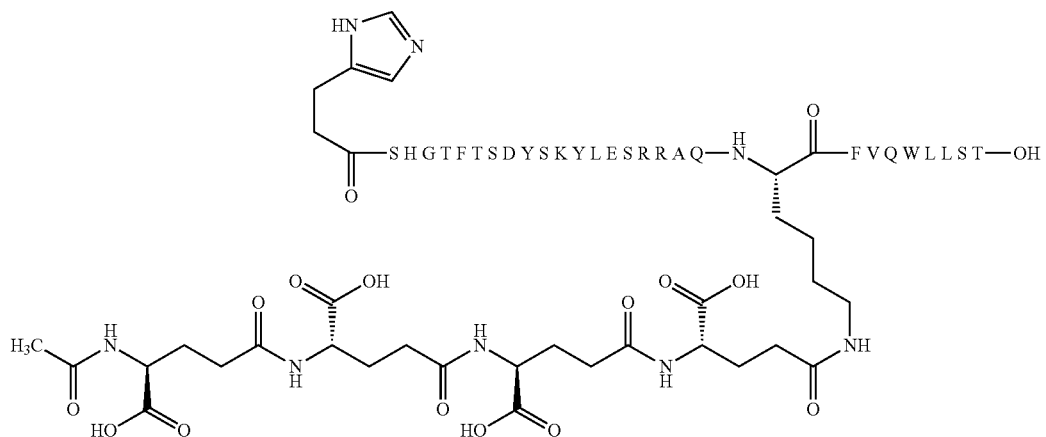

UPLC01: Rt=9.5 min
LCMS01: Rt=3.1 min; Calc m/z=4017.3. Found m/3=1340. Found m/4=1005. Found m/5=804.

Example 14

N$^{\epsilon 28}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Leu27, Lys28]-Glucagon

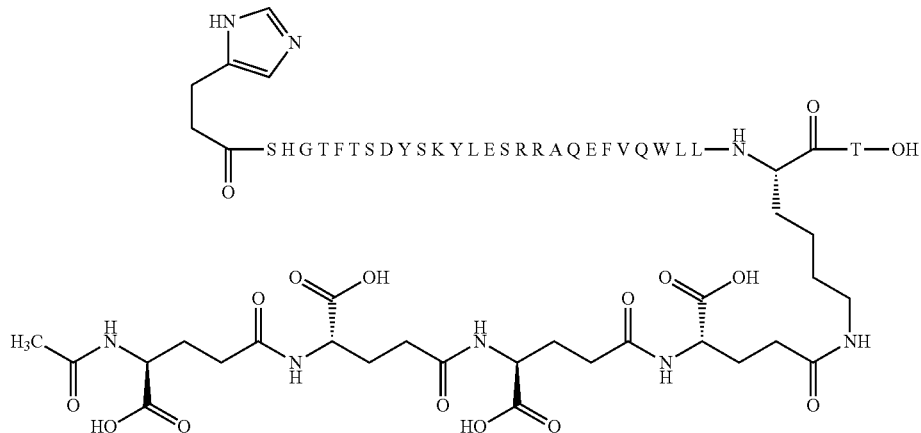

Chem. 14 (SEQ ID NO: 15)

UPLC02: Rt=6.2 min
LCMS01: Rt=3.2 min; Calc m/z=4059.3. Found m/3=1354. Found m/4=1015. Found m/5=812.

Example 15

N$^{\epsilon 29}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Leu27, Ser28, Lys29]-Glucagon

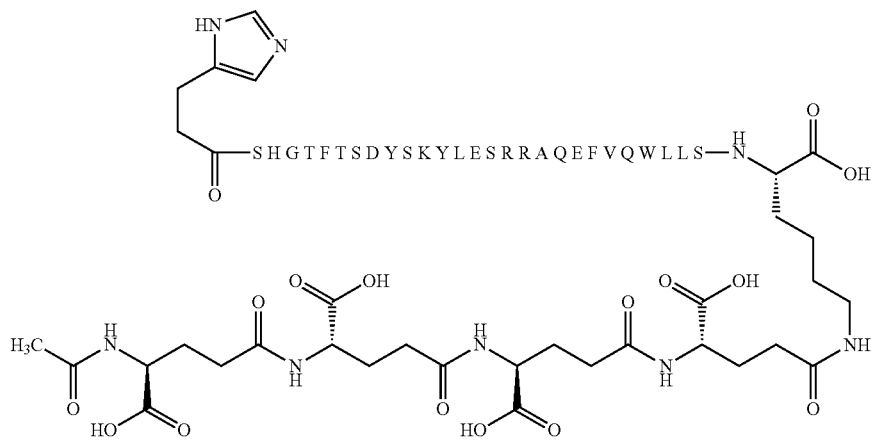

Chem. 15 (SEQ ID NO: 16)

UPLC01: Rt=9.4 min
LCMS01: Rt=4.1 min; Calc m/z=4045.3. Found m/3=1349. Found m/4=1012. Found m/5=810.

Example 16

N$^\alpha$([Imp1, His3, Glu15, Glu21, Leu27, Ser28]-Glucagonyl)-N{Epsilon}[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]Lys Chem. 16

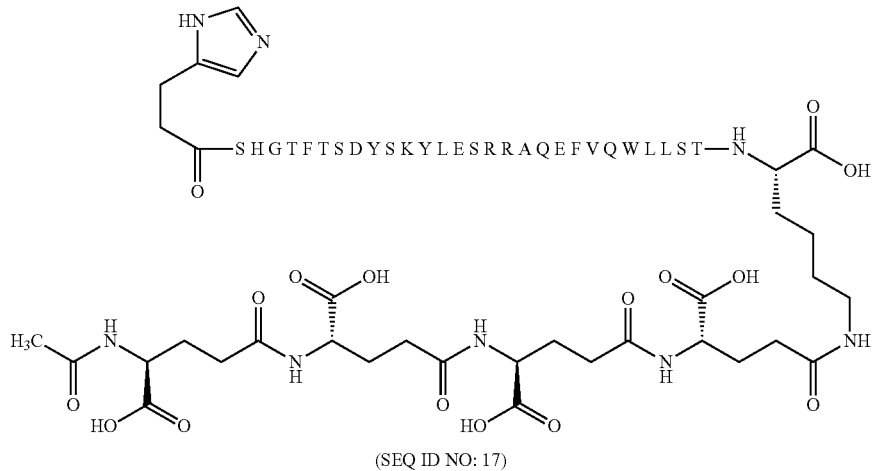

(SEQ ID NO: 17)

UPLC01: Rt=9.2 min
LCMS01: Rt=4.1 min; Calc m/z=4146.4. Found m/3=1383. Found m/4=1037. Found m/5=830.

Example 17

N$^{\epsilon 24}$-[2-[[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]amino]acetyl]-[Imp1, His3, Glu15, Glu21, Lys24, Leu27, Ser28]-Glucagon Chem. 17

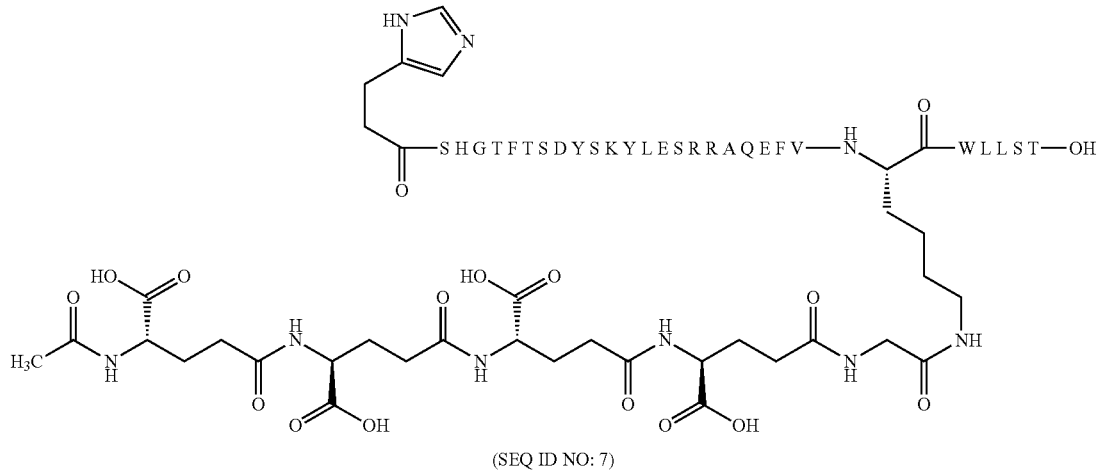

(SEQ ID NO: 7)

UPLC01: Rt=9.6 min
LCMS01: Rt=1.8 min; Calc m/z=4075.3. Found m/3=1359.7. Found m/4=1020.0. Found m/5=816.2.

Example 18

N^ε24-[(4S)-4-[[(4S)-4-[[(4S)-4-acetamido-4-carboxybutanoyl]amino]-4-carboxybutanoyl]amino]-4-carboxybutanoyl]-[Imp1, His3, Glu15, Glu21, Lys24, Leu27, Ser28]-Glucagon

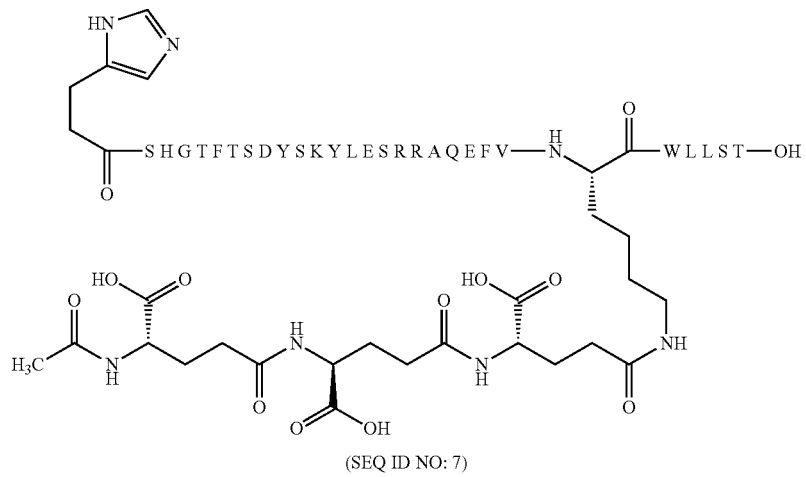

Chem. 18

(SEQ ID NO: 7)

UPLC01: Rt=9.8 min
LCMS01: Rt=1.8 min; Calc m/z=3889.2. Found m/3=1297.3. Found m/4=973.2. Found m/5=1178.8.

Example 19

N^ε24-[(4S)-4-[[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Ser28]-Glucagon

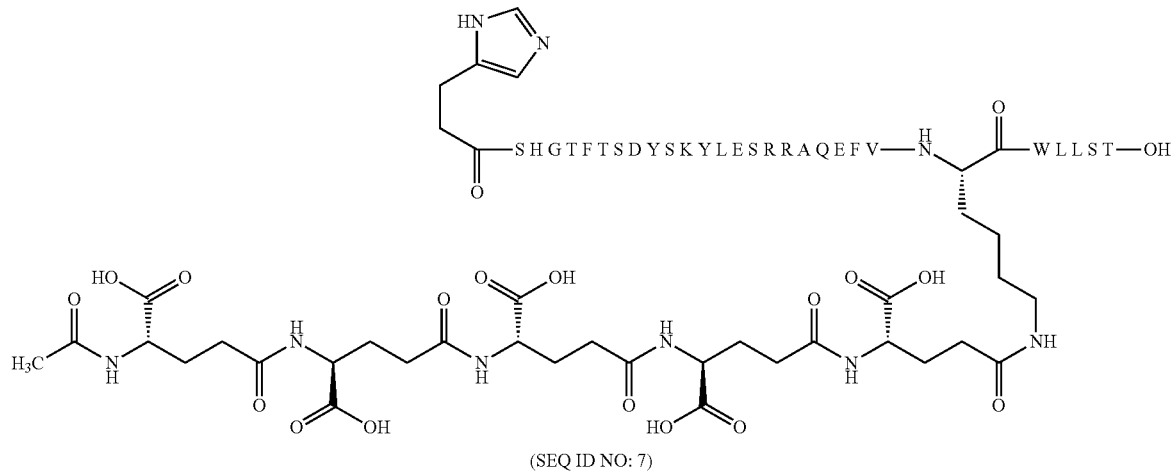

Chem. 19

(SEQ ID NO: 7)

UPLC01: Rt=9.8 min
LCMS01: Rt=1.8 min; Calc m/z=4147.4. Found m/3=1383.4. Found m/4=1037.7. Found m/5=830.4.

Example 20

N^ε24-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Ala16, Lys24, Leu27, Ser28]-Glucagon Chem. 20

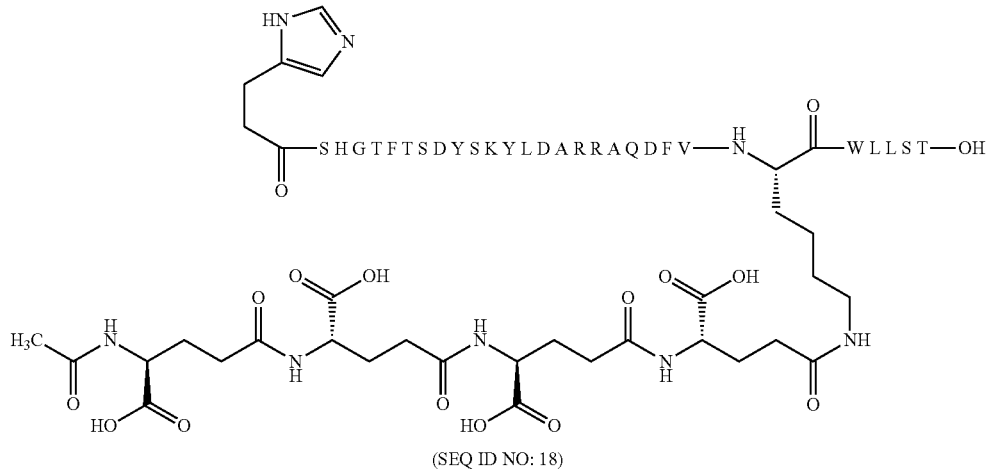

(SEQ ID NO: 18)

UPLC01: Rt=10.2 min
LCMS01: Rt=1.9 min; Calc m/z=3974.2. Found m/3=1325.6. Found m/4=994.5. Found m/5=795.8.

Example 21

N^ε24-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Aib16, Lys24, Leu27, Ser28]-Glucagon Chem. 21

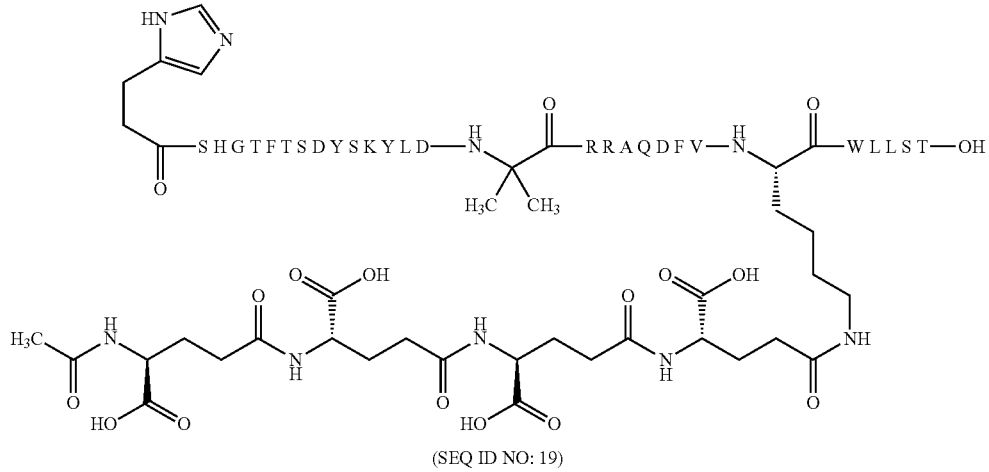

(SEQ ID NO: 19)

UPLC01: Rt=10.6 min
LCMS01: Rt=2.0 min; Calc m/z=3988.2. Found m/3=1330.0. Found m/4=998.0. Found m/5=798.6.

Example 22

$N^{\epsilon 24}$-[(4S)-4-[[(4S)-4-[[(4S)-4-[[(4S)-4-acetamido-4-carboxybutanoyl]amino]-4-carboxybutanoyl]amino]-4-carboxybutanoyl]amino]-4-carboxybutanoyl]-[Imp1, His3, Glu15, Glu21, Lys24, Leu27, Glu28]-Glucagon Chem. 22 (SEQ ID NO: 20)

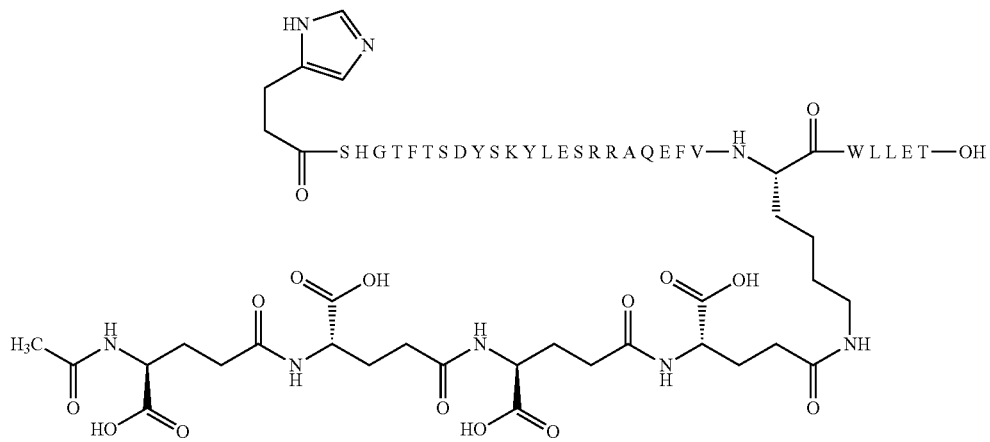

UPLC01: Rt=10.0 min
LCMS01: Rt=1.8 min; Calc m/z=4060.3. Found m/3=1354.3. Found m/4=1016.0. Found m/5=813.0.

Assay (I): GLP-1 and Glucagon Receptor Potency

The purpose of this assay is to test the activity, or potency, of the derivatives of the invention, in vitro. The in vitro potency is the measure of human GLP-1 receptor and/or glucagon receptor activation, respectively, in a whole cell assay.

Principle

In vitro potency was determined by measuring the response of human GLP-1 or glucagon receptor, respectively, in a reporter gene assay. The assay was performed in a stably transfected BHK cell line that expressed either the human GLP-1 receptor or the human glucagon receptor and contained the DNA for the cAMP response element (CRE) coupled to a promoter and the gene for firefly luciferase (CRE luciferase). When the human GLP-1 or glucagon receptor, respectively, was activated it resulted in the production of cAMP, which in turn resulted in the luciferase protein being expressed. When assay incubation was completed, the luciferase substrate (luciferin) was added and the enzyme converted luciferin to oxyluciferin and produced bioluminescence. The luminescence was measured as the readout for the assay.

(a) GLP-1 Receptor Activation
Cell Culture and Preparation

The cells used in this assay (clone FCW467-12A/KZ10-1) were BHK cells with BHKTS13 as a parent cell line. The cells were derived from a clone (FCW467-12A) that expressed the human GLP-1 receptor and were established by further transfection with CRE luciferase to obtain the current clone.

The cells were cultured at 5% CO2 in DMEM medium with 10% FBS, 1× GlutaMAX, 1 mg/mL G418, 240 nM MTX (methotrexate) and 1% pen/strep (penicillin/streptomycin). They were aliquoted and stored in liquid nitrogen. Before each assay, an aliquot was taken up and washed three times in PBS before being suspended at the desired concentration in assay buffer. For 96-well plates the suspension was made to give a final concentration of 5×10 EE3 cells/well.

Materials

The following chemicals were used in the assay: Pluronic F-68 (10%) (Gibco 2404), ovalbumin (Sigma A5503), DMEM w/o phenol red (Gibco 11880-028), 1 M Hepes (Gibco 15630), Glutamax 100× (Gibco 35050) and steady-lite plus (PerkinElmer 6016757).

Assay Medium consisted of DMEM w/o phenol red, 10 mM Hepes, 1× GlutaMAX, 2% Ovalbumin and 0.2% Pluronic F-68.

Procedure

Cell stocks were thawed in a 37° C. water bath. Cells were washed three times in PBS. The cells were counted and adjusted to 5×10 EE3 cells/50 µl (1×10 EE5 cells/mL) in Assay Medium. A 50 µl aliquot of cells was transferred to each well in the assay plate.

Stocks of the test compounds and reference compounds were diluted to a concentration of 0.2 µM in Assay Medium. Compounds were diluted 10-fold to give the following concentrations: 2×10 EE-6 M, 2×10 EE-7 M, 2×10 EE-8 M; 2×10 EE-9 M, 2×10 EE-10 M, 2×10 EE-11 M, 2×10 EE-12 M and 2×10 EE-13 M. For each compound a blank assay buffer control was also included.

A 50 µl aliquot of compound or blank was transferred from the dilution plate to the assay plate. Compounds were tested at the following final concentrations: 1×10 EE-6 M, 1×10 EE-7 M, 1×10 EE-8 M; 1×10 EE-9 M, 1×10 EE-10 M, 1×10 EE-11 M and 1×10 EE-12 M and 1×10 EE-13 M.

The assay plate was incubated for 3 h in a 5% CO2 incubator at 37° C. The assay plate was removed from the incubator and allowed to stand at room temperature for 15 min. A 100 µl aliquot of steadylite plus reagent was added to each well of the assay plate (reagent is light sensitive). Each assay plate was covered with aluminum foil to protect it from light and shaken for 30 min at room temperature. Each assay plate was read in a Packard TopCount NXT instrument.

Calculations

The data from the TopCount instrument was transferred to GraphPad Prism software. The software performed a non-linear regression (log(agonist) vs response-Variable slope (four parameter)). EC50 values were calculated by the software and reported in pM.

(b) Glucagon Receptor Activation
Cell Culture and Preparation

The cells used in this assay (clone pLJ6'-4-25) were BHK cells with BHK570 as a parent cell line expressing the CRE luciferase gene (clone BHK/KZ10-20-48) and were established by further transfection with the human glucagon receptor (clone pLJ6' in pHZ-1 vector).

The cells were cultured at 5% CO2 in DMEM medium with 10% FBS, 1× GlutaMAX, 1 mg/mL G418, 240 nM MTX (methotrexate) and 1% pen/strep (penicillin/streptomycin). They were aliquoted and stored in liquid nitrogen. Before each assay, an aliquot was taken up and washed three times in PBS before being suspended at the desired concentration in assay buffer. For 96-well plates the suspension was made to give a final concentration of $5 \times 10^{3}$ cells/well.

Materials

The following chemicals were used in the assay: Pluronic F-68 (10%) (Gibco 2404), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Assay Medium consisted of DMEM w/o phenol red, 10 mM Hepes, 1x GlutaMAX, 2% Ovalbumin and 0.2% Pluronic F-68.

Procedure

Cell stocks were thawed in a 37° C. water bath. Cells were washed three times in PBS. The cells were counted and adjusted to $5 \times 10^{3}$ cells/50 μl ($1 \times 10^{5}$ cells/mL) in Assay Medium. A 50 μl aliquot of cells was transferred to each well in the assay plate.

Stocks of the test compounds and reference compounds were diluted to a concentration of 0.2 μM in Assay Medium. Compounds were diluted 10-fold to give the following concentrations: $2 \times 10^{-6}$ M, $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M and $2 \times 10^{-13}$ M. For each compound a blank assay buffer control was also included.

A 50 μl aliquot of compound or blank was transferred from the dilution plate to the assay plate. Compounds were tested at the following final concentrations: $1 \times 10^{-6}$ M, $1 \times 10^{-7}$ M, $1 \times 10^{-8}$ M; $1 \times 10^{-9}$ M, $1 \times 10^{-10}$ M, $1 \times 10^{-11}$ M and $1 \times 10^{-12}$ M and $1 \times 10^{-13}$ M.

The assay plate was incubated for 3 h in a 5% CO2 incubator at 37° C. The assay plate was removed from the incubator and allowed to stand at room temperature for 15 min. A 100 μl aliquot of steadylite plus reagent was added to each well of the assay plate (reagent is light sensitive). Each assay plate was covered with aluminum foil to protect it from light and shaken for 30 min at room temperature. Each assay plate was read in a Packard TopCount NXT instrument.

Calculations

The data from the TopCount instrument was transferred to GraphPad Prism software. The software performed a non-linear regression (log(agonist) vs response-Variable slope (four parameter)). EC50 values were calculated by the software and reported in pM.

Assay (II): GLP-1 and Glucagon Receptor Binding
(a) GLP-1 Receptor Binding

The purpose of this assay is to test the in vitro receptor binding activity of the glucagon derivatives of the invention. The receptor binding is a measure of affinity of a compound for the human GLP-1 receptor.

Principle

The receptor binding of each compound to the human GLP-1 receptor was measured in a displacement binding assay. In this type of assay a labelled ligand (in this case 125I-GLP-1) is bound to the receptor. Each derivative is added in a series of concentrations to isolated membranes containing the human GLP-1 receptor and displacement of the labelled ligand is monitored. The receptor binding is reported as the concentration at which half of the labelled ligand is displaced from the receptor, the IC50 value.

Materials

The following chemicals were used in the assay: DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, MgCl2 (Merck 1.05832.1000), Tween 20 (Amresco 0850C335), SPA particles (wheat germ agglutinin (WGA) SPA beads, Perkin Elmer RPNQ0001), [125I]-GLP-1]-(7-36)NH2 (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM MgCl2, 0.005% Tween 20 and pH was adjusted to 7.4.

Cell Culture and Membrane Preparation

The cells used in this assay (clone FCW467-12A) were BHK cells with BHKTS13 as a parent cell line. The cells express the human GLP-1 receptor.

The cells were grown at 5% CO2 in DMEM, 10% fetal calf serum, 1% Pen/Strep (Penicillin/Streptomycin) and 1.0 mg/mL of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX dispersing instrument for 20-30 seconds in a suitable amount of buffer 1 (e.g., 10 mL). The homogenate was centrifuged for 15 minutes. The pellet was re-suspended (homogenised) in 10 mL buffer 2 and centrifuged. This step was repeated once more. The resulting pellet was re-suspended in buffer 2 and the protein concentration was determined. The membranes were aliquoted and stored at minus 80° C.

Procedure
1. For the receptor binding assay 50 μl of the assay buffer was added to each well of an assay plate.
2. Test compounds were serially diluted to give the following concentrations: $8 \times 10^{-7}$ M, $8 \times 10^{-8}$ M, $8 \times 10^{-9}$ M, $8 \times 10^{-10}$ M, $8 \times 10^{-11}$ M, $8 \times 10^{-12}$ M and $8 \times 10^{-13}$ M. Twenty-five μl were added to appropriate wells in the assay plate.
3. Cell membrane aliquots were thawed and diluted to their working concentration. Fifty μl were added to each well in the assay plate.
4. WGA SPA beads were suspended in assay buffer at 20 mg/mL. The suspension was diluted to 10 mg/mL in assay buffer just prior to addition to the assay plate. Fifty μl were added to each well in the assay plate.
5. The incubation was started by adding 25 μl of 480 pM solution of [125I]-GLP-1]-(7-36)NH2 to each well of the assay plate. A 25 μl aliquot was reserved for measuring total counts/well.
6. The assay plate was incubated for 2 h at 30° C.
7. The assay plate was centrifuged for 10 min.
8. The assay plate was read in a Packard TopCount NXT instrument.

Calculations

The data from the TopCount instrument were transferred to GraphPad Prism software. The software averaged the values for the replicates and performed a non-linear regression. IC50 values were calculated by the software and reported in nM.

(b) Glucagon Receptor Binding

The purpose of this assay was to test the in vitro receptor binding activity of the glucagon derivatives of the invention. The receptor binding activity is a measure of affinity of a derivative for the human glucagon receptor.

Principle

The receptor binding of each compound to the human glucagon receptor was measured in a displacement binding assay. In this type of assay a labelled ligand (in this case 125I-glucagon) is bound to the receptor. Each derivative is added in a series of concentrations to isolated membranes containing the human glucagon receptor and displacement of the labelled ligand is monitored. The receptor binding is reported as the concentration at which half of the labelled ligand is displaced from the receptor, the IC50 value.

Materials

The following chemicals were used in the assay: DMEM w Glutamax (Gibco 61965-026), Pen/strep (Invitrogen 15140-122), G418 (Invitrogen 10131-027), Versene (Gibco 15040), 1 M Hepes (Gibco 15630), PBS (Invitrogen 14190-094), fetal calf serum (Invitrogen 16140-071), MgCl2 (Merck 1.05832.1000), EDTA (Invitrogen 15575-038), CaCl2 (Sigma, C5080), Tween 20 (Amresco 0850C335), ovalbumin (Sigma A5503), SPA particles (wheat germ agglutinin (WGA) SPA beads, Perkin Elmer RPNQ0001), [125I]-glucagon (produced in-house), OptiPlate™-96 (Packard 6005290).

HME buffer consisted of 25 mM HEPES, 2 mM MgCl2 and 1 mM EDTA, and pH was adjusted to 7.4. Binding buffer consisted of 50 mM HEPES supplemented with 5 mM MgCl2, 1 mM CaCl2, 0.02% Tween 20 and 0.1% Ovalbumin, and pH was adjusted to 7.4.

Cell Culture and Membrane Preparation.

The cells used in this assay (clone BHK hGCGR A3*25) were BHK cells stable transfected with an expression plasmid containing the cDNA encoding the human glucagon receptor.

The cells were grown at 5% $CO_2$ in DMEM, 10% fetal calf serum, 1% Pen/Strep (Penicillin/Streptomycin) and 1.0 mg/mL of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. The cells were lysed by adding approx. 5 mL HME buffer, mix by pipetting and snap freeze in liquid nitrogen. The cell lysate was quickly thawed and HME buffer added to 10 mL. The cell pellet was homogenised with an ULTRA-THUR-RAX dispersing instrument for 20-30 seconds. The homogenate was centrifuged at 20,000×G, 4° C. for 10 minutes. The pellet was resuspended (homogenised) in 1-2 mL HME buffer. The protein concentration was determined. The membranes were aliquoted and snap frozen in liquid nitrogen and stored at minus 80° C.

Procedure

1. For the receptor binding assay 50 µl of the assay buffer was added to each well of an assay plate.
2. Test compounds were serially diluted to give the following concentrations: 8×10 EE-7 M, 8×10 EE-8 M, 8×10 EE-9 M, 8×10 EE-10 M, 8×10 EE-11 M, 8×10 EE-12 M and 8×10 EE-13 M. Twenty-five µl were added to appropriate wells in the assay plate.
3. Cell membrane aliquots were thawed and diluted to their working concentration. Fifty µl were added to each well in the assay plate.
4. WGA SPA beads were suspended in assay buffer at 20 mg/mL. The suspension was diluted to 10 mg/mL in assay buffer just prior to addition to the assay plate. Fifty µl were added to each well in the assay plate.
5. The incubation was started by adding 25 µl of 480 pM solution of [125I]-glucagon to each well of the assay plate. A 25 µl aliquot was reserved for measuring total counts/well.
6. The assay plate was incubated for 2 h at 25° C.
7. The assay plate was centrifuged for 10 min at 1500 rpm.
8. The assay plate was read in a Packard TopCount NXT instrument.

Calculations

The data from the TopCount instrument were transferred to GraphPad Prism software. The software averaged the values for the replicates and performed a non-linear regression.

Assay (III): ThT Fibrillation Assay for the Assessment of Physical Stability of Peptide Compositions The purpose of this assay is to assess the physical stability of the glucagon derivatives of the invention in aqueous solutions.

Low physical stability of a peptide may lead to amyloid fibril formation, which is observed as well-ordered, thread-like macromolecular structures in the sample, which eventually may lead to gel formation. This has traditionally been measured by visual inspection of the sample. However, that kind of measurement is very cumbersome and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \quad \text{Eq. (1)}$$

Here, as depicted in FIG. 1, F is the ThT fluorescence at the time t. The constant t0 is the time needed to reach 50% of maximum fluorescence. The two important parameters describing fibril formation are the lag-time calculated by t0−2τ and the apparent rate constant kapp 1/τ.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Samples were prepared freshly before each assay. Each sample composition is described in the legends. The pH of the sample was adjusted to the desired value using appropriate amounts of concentrated NaOH and HCl. Thioflavin T was added to the samples from a stock solution in $H_2O$ to a final concentration of 1 µM.

Sample aliquots of 200 μl (250 μM of the glucagon derivative/analogue in 10 mM HEPES buffer, pH 7.5) were placed in a 96 well microtiter plate (Packard OptiPlate™-96, white polystyrene). Usually, four or eight replica of each sample (corresponding to one test condition) was placed in one column of wells. The plate was sealed with Scotch Pad (Qiagen).

Incubation at given temperature, shaking and measurement of the ThT fluorescence emission were done in a Fluoroskan Ascent FL fluorescence platereader (Thermo Labsystems). The plate was incubated 37° C. with orbital shaking adjusted to 960 rpm with an amplitude of 1 mm. Fluorescence measurement was done using excitation through a 444 nm filter and measurement of emission through a 485 nm filter. Each run was initiated by incubating the plate at the assay temperature for 10 min. The plate was measured every 20 minutes for a desired period of time. Between each measurement, the plate was shaken and heated as described.

After completion of the ThT assay the four or eight replica of each sample was pooled and centrifuged at 20000 rpm for 30 minutes at 18° C. The supernatant was filtered through a 0.22 μm filter and an aliquot was transferred to a HPLC vial. The concentration of peptide in the initial sample and in the filtered supernatant was determined by reverse phase HPLC using an appropriate standard as reference. The percentage fraction the concentration of the filtered sample constituted of the initial sample concentration was reported as the recovery.

The measurement points were saved in Microsoft Excel format for further processing and curve drawing and fitting was performed using GraphPad Prism. The background emission from ThT in the absence of fibrils was negligible. The data points were typically a mean of four or eight samples and shown with standard deviation error bars. Only data obtained in the same experiment (i.e. samples on the same plate) were presented in the same graph ensuring a relative measure of fibrillation between experiments.

The data set may be fitted to Eq. (1). However, the lag time before fibrillation reported herein was determined by visual inspection of the curve identifying the time point at which ThT fluorescence increases significantly above the background level.

Assay (IV): Chemical Stability Assessment

The purpose of this assay is to assess the chemical stability of the glucagon derivatives of the invention in aqueous solutions.

Chemical stability of glucagon analogues was determined by RP-UPLC. Lyophilized samples were dissolved in a 8 mM phosphate buffer pH 8.6, followed by adjustment to pH 7.3 using HCl to a final concentration of 333 μM. Samples were incubated for 14 days at 5° C. and 37° C. followed by RP-UPLC analysis. Purity was defined as the area percentage of the main peak in relation to the total area of all integrated peaks in each chromatogram. The chemical stability determined as the purity loss (also referred to herein as chemical degradation) after 14 days at 37° C. was determined as the difference in purity between the samples incubated at 5° C. or a start sample (no incubation) and 37° C., divided by the purity of the start sample or after incubation for 14 days at 5° C.

RP-UPLC analysis was performed using a Waters Acquity CSH Fluoro-phenyl 150×2.1 mm, 1.7 μm column operated at 50° C. and a flow rate of 0.3 mL/min using a mobile phase system consisting of A: 0.09 M phosphate buffer pH 3.6 (di-ammoniumhydrogenphosphat), 10% MeCN (v/v %), and B: 60% MeCN (v/v %), 20% Isopropanol (v/v %).

UV-detection was performed at 215 nm. The typical gradient profile used for most of the samples is shown below. For analogues eluting at substantially different retention times compared with the majority of analogues, some adjustments to the gradient profile were made to better enable purity assessment comparison across samples. The data confirmed the improved chemical stability of the glucagon derivatives of this invention.

The high molecular weight protein (HMWP) content was determined by size-exclusion high performance liquid chromatography (SE-HPLC). The analysis was performed using a Waters Insulin HMWP 7.8×300 mm column operated at 50° C. and a flow rate of 0.5 mL/min using a dissociating mobile phase consisting of 500 mM NaCl, 10 mM $NaH_2PO_4$, 5 mM $H_3PO_4$ and 50% (v/v) 2-propanol. UV-detection was performed at 215 nm.

Typical Gradient Profile Used for RP-UPLC Analysis:

| Time (min) | % B |
|---|---|
| Injection | 24.8 |
| 1 | 24.8 |
| 52.5 | 35.8 |
| 54 | 90 |
| 55 | 90 |
| 55.2 | 24.8 |
| 60 | 24.8 |

Example 23: Properties of the Derivatives of the Invention

Derivatives of the invention were tested for potency on the human glucagon receptor (EC50 hGlucagonR), affinity to the human glucagon receptor (IC50 hGlucagonR), physical stability and chemical stability using Assay (I)(b), Assay (II)(b), Assay (III) and Assay (IV) as described herein, respectively. The results are shown in Table 1.

TABLE 1

| Derivative of Example | EC50 hGlucagonR (pM) | IC50 hGlucagonR (nM) | Physical stability: THT assay Lag time (hours) | Physical stability: THT assay Recovery (%) | Chemical stability: Chemical degradation over 14 days at 37° C. (%) |
|---|---|---|---|---|---|
| Example 1 | 1.0 | 0.2 | 45.0 | 101 | 1.9 |
| Example 2 | 5.0 | 1.9 | 45.0 | 104 | 3.0 |
| Example 3 | 10.0 | 4.9 | 45.0 | 100 | 2.5 |
| Example 4 | 5.0 | 1.8 | 45.0 | 100 | 3.8 |
| Example 5 | 12.0 | 6.2 | 45.0 | 100 | 3.1 |
| Example 6 | 4.7 | 1.8 | 45.0 | 101 | 0.6 |
| Example 7 | 2.0 | 1.0 | 36.9 | 100 | 2.1 |
| Example 8 | 1.0 | 0.2 | 45.0 | 103 | 1.7 |
| Example 9 | 3.0 | 0.5 | 45.0 | 100 | 2.1 |

TABLE 1-continued

| Derivative of Example | EC50 hGlucagonR (pM) | IC50 hGlucagonR (nM) | Physical stability: THT assay Lag time (hours) | Physical stability: THT assay Recovery (%) | Chemical stability: Chemical degradation over 14 days at 37° C. (%) |
|---|---|---|---|---|---|
| Example 10 | 2.0 | 0.5 | 45.0 | 100 | 2.8 |
| Example 11 | 105.0 | 24.4 | 1.7 | 98 | −3.3 |
| Example 12 | 41.0 | 7.6 | 6.7 | 88 | 2.5 |
| Example 13 | 17.0 | 5.2 | 0.3 | 39 | −0.3 |
| Example 14 | 6.0 | 2.6 | 1.7 | 98 | n.d.[a] |
| Example 15 | 4.0 | 5.1 | 2.3 | 88 | 2.8 |
| Example 16 | 4.0 | 2.0 | 6.0 | 61 | 5.0 |
| Example 17 | 9.9 | 2.5 | 4.3 | 100 | 0.9 |
| Example 18 | 6.0 | 1.5 | 45.0 | 100 | 1.4 |
| Example 19 | 6.0 | 2.7 | 45.0 | 104 | 1.4 |
| Example 20 | 4.0 | 0.9 | 45.0 | 105 | n.d. |
| Example 21 | 2.0 | 0.3 | 45.0 | 104 | 2.4 |
| Example 22 | 17.0 | 8.7 | 45.0 | 100 | 0.9 |

[a] "n.d." is not determined.

The results show the derivatives of the invention have good potency on the glucagon receptor, a good affinity to the glucagon receptor as well as good or moderate physical stability and good chemical stability.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a glucagon analogue, comprising a peptide and a substituent;
wherein the peptide comprises the amino acid sequence
Imp-$X_2$-His-Gly-Thr-Phe-Thr-Ser-Asp-$X_{10}$-Ser-$X_{12}$-Tyr-Leu-$X_{15}$-$X_{16}$-Arg-Arg-Ala-$X_{20}$-$X_{21}$-Phe-Val-$X_{24}$-Trp-Leu-$X_{27}$-$X_{28}$-$X_{29}$-$X_{30}$;
wherein
$X_2$ is Ser or Aib;
$X_{10}$ is Tyr, Leu, Ile or Val;
$X_{12}$ is Lys or Arg;
$X_{15}$ is Asp or Glu;
$X_{16}$ is Ser, Ala, Leu, Thr, Aib, Ile, Val or Lys;
$X_{20}$ is Gln, Glu, Aib or Lys;
$X_{21}$ is Asp, Glu or Lys;
$X_{24}$ is Gln, Ala, Glu, Aib or Lys;
$X_{27}$ is Met, Leu or Val;
$X_{28}$ is Asn, Ser, Thr, Gln, Ala, Gly, Glu or Lys;
$X_{29}$ is Thr, Gly, Ser, Gln, Ala, Glu or Lys; and
$X_{30}$ is absent or is Lys;
wherein the substituent is covalently attached to the nitrogen atom of the side chain of a lysine in the peptide at a position selected from the group consisting of $X_{12}$, $X_{16}$, $X_{20}$, $X_{21}$, $X_{24}$, $X_{28}$, $X_{29}$ and $X_{30}$;

wherein the substituent comprises the formula $Y_1$-$Y_2$-$Y_3$-$Y_4$-$Y_5$-$Y_6$-$Y_7$-$Y_8$-$Y_9$-$Y_{10}$-$Y_{11}$-$Y_{12}$-;

wherein $Y_1$ is selected from the group consisting of hydrogen, a $C_{2-6}$ acyl group, and a succinoyl moiety;

wherein $Y_2$, $Y_2$, $Y_3$, $Y_4$, $Y_5$, $Y_6$, $Y_7$, $Y_8$, $Y_9$, $Y_{10}$, $Y_{11}$ and $Y_{12}$ individually are absent or represents an amino acid residue selected from the group consisting of Ser, Ala, Gly,

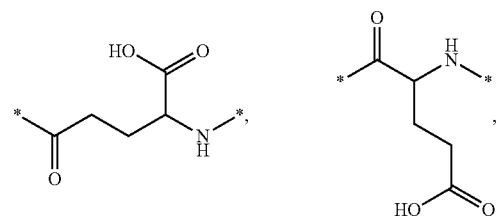

-continued

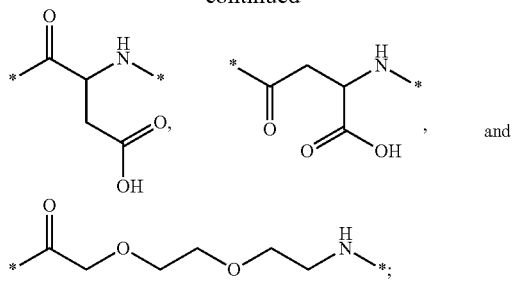

wherein

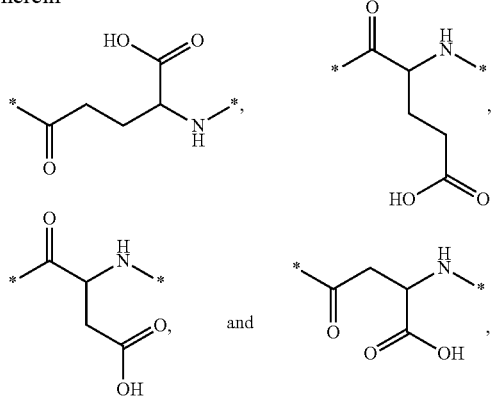

individually has stereochemistry L or D;

or a pharmaceutically acceptable salt, amide, or ester thereof.

2. The derivative according to claim 1, wherein $Y_{12}$ is present and attached to the nitrogen atom of the side chain of the lysine.

3. The derivative according to claim 1, wherein the substituent is covalently attached to the epsilon-nitrogen atom of the side chain of the lysine.

4. The derivative according to claim 1, wherein the substituent is attached to the lysine in position $X_{24}$.

5. The derivative according to claim 1, wherein the substituent has 3, 4, 5, 6, 7, 8, or 9 negatively charged moieties.

6. The derivative according to claim 1, wherein the substituent comprises 3-10 amino acid residues of

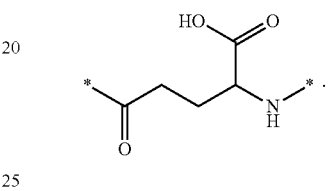

7. The derivative according to claim 1, wherein $Y_1$ is an acetyl group.

8. The derivative according to claim 1, wherein the derivative is selected from the group consisting of (Chem. 1)

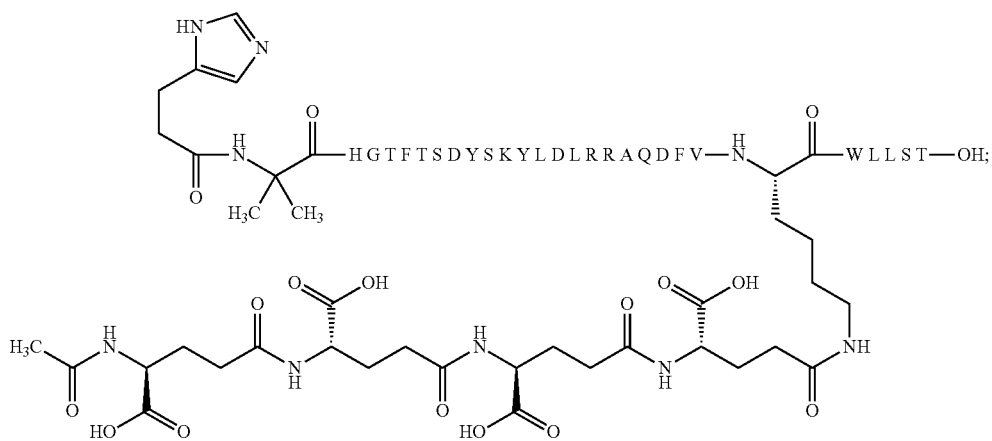

(Chem. 2)

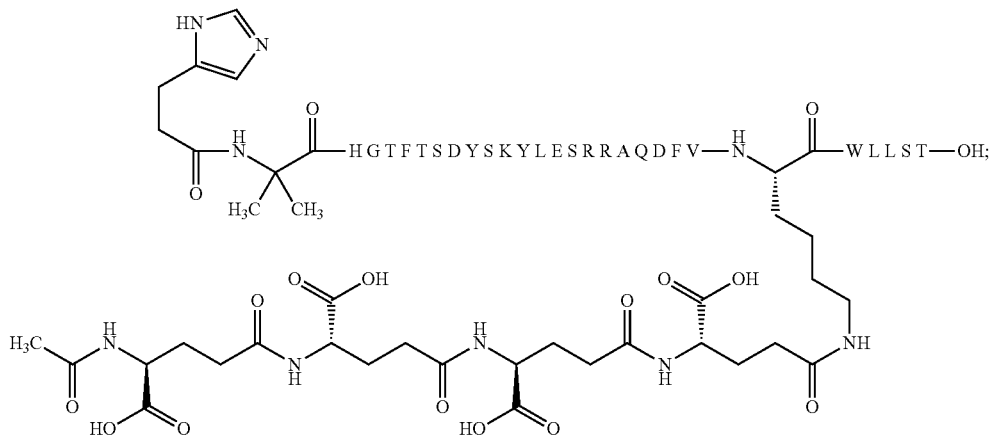

(Chem. 3)
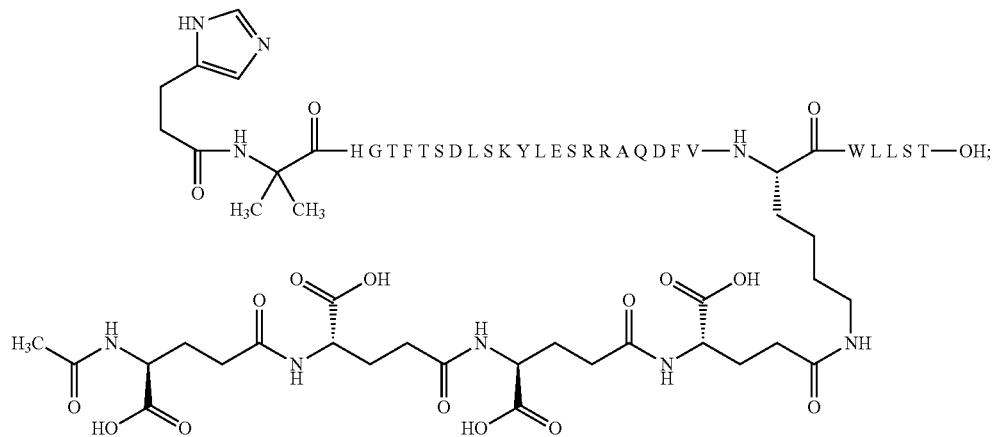
(Chem. 4)
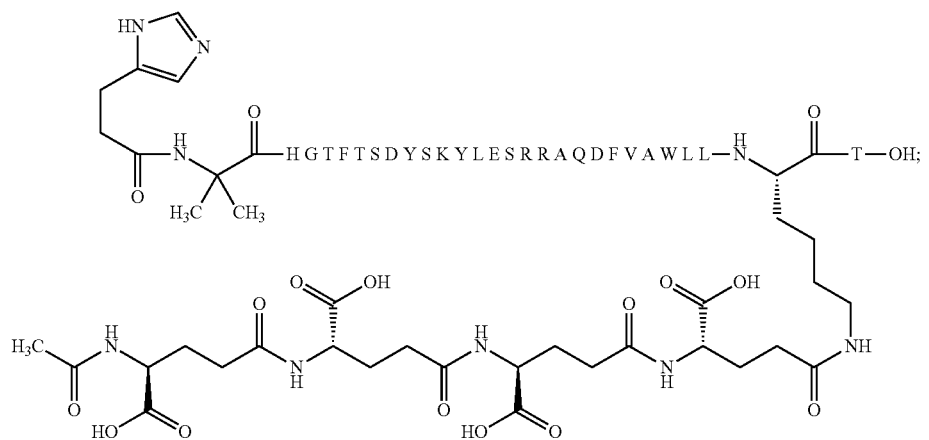
(Chem. 5)
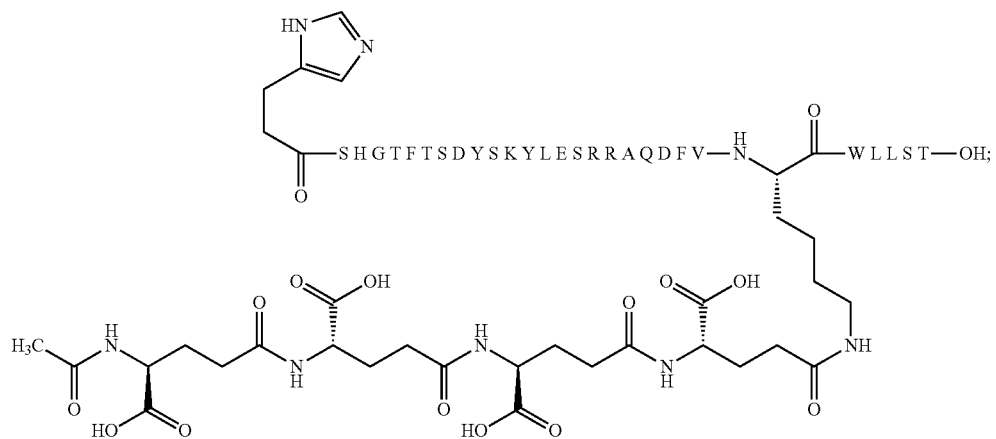

-continued
(Chem. 6)
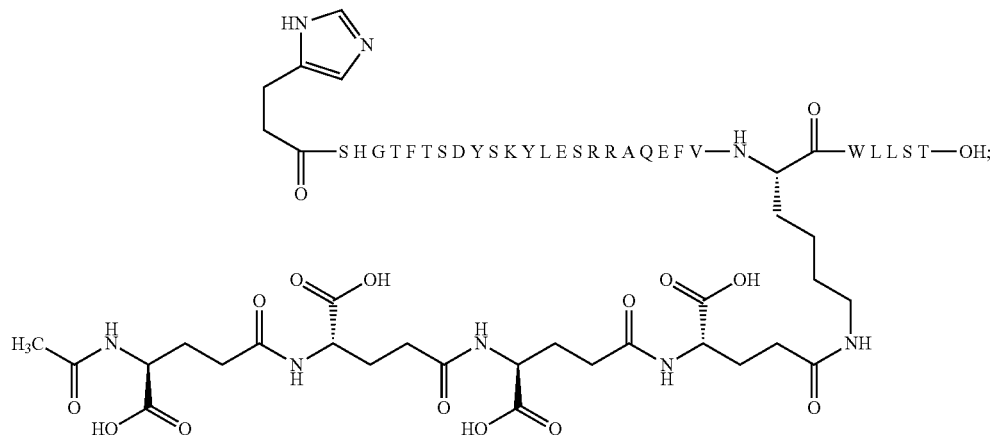
(Chem. 7)
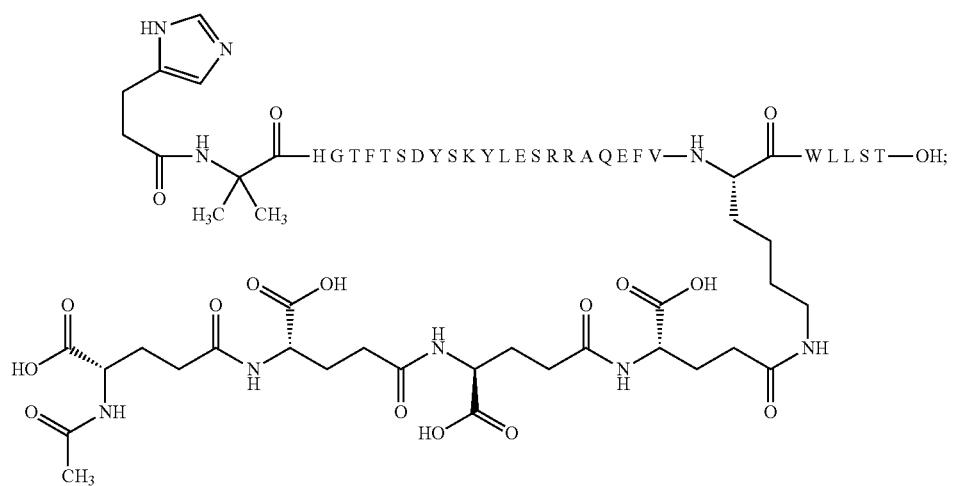
(Chem. 8)
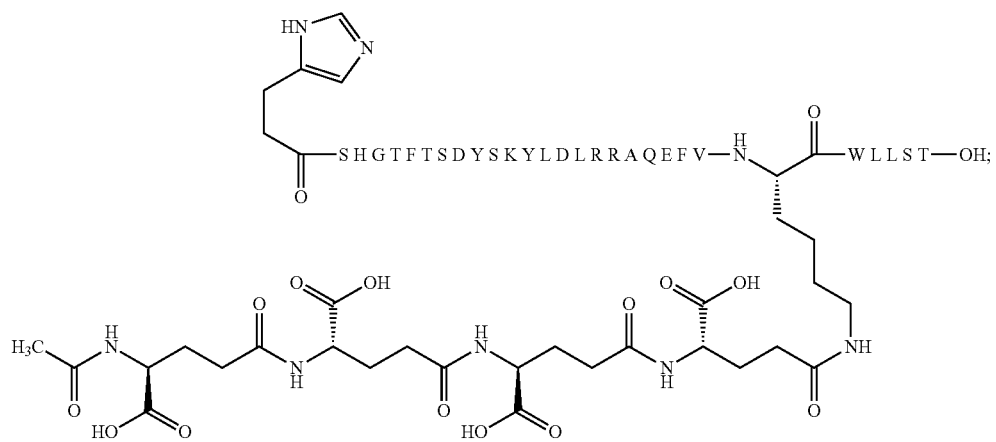

(Chem. 9)
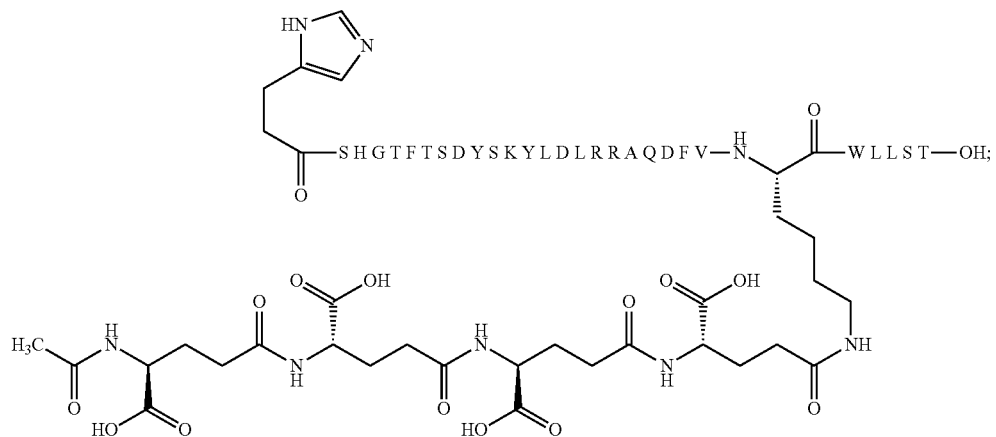
(Chem. 10)
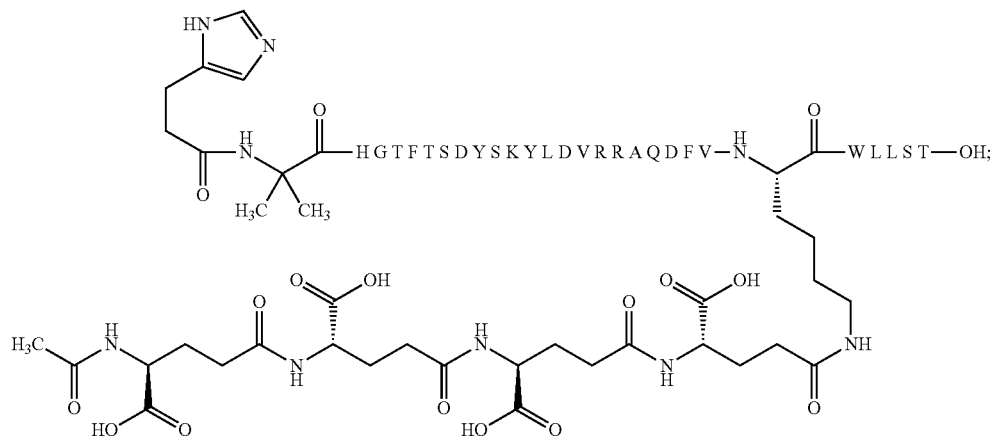
(Chem. 11)
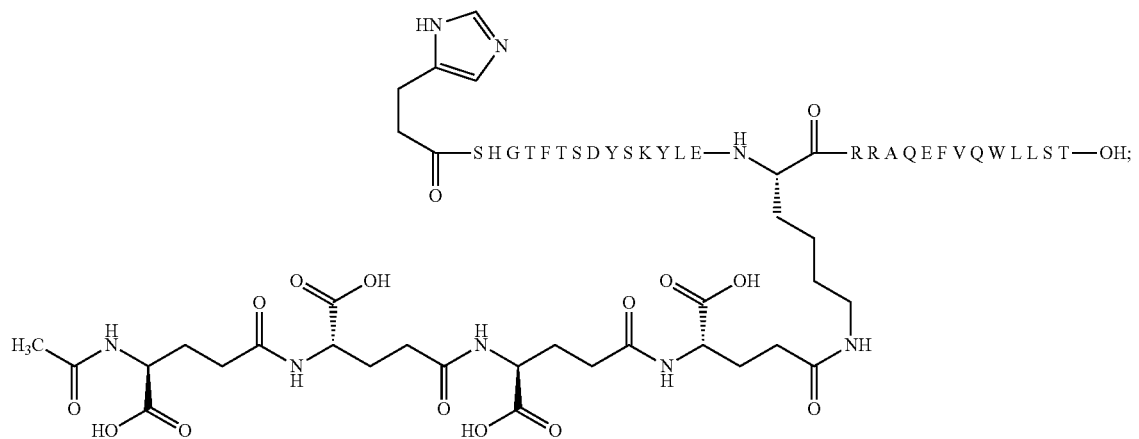

(Chem. 12)
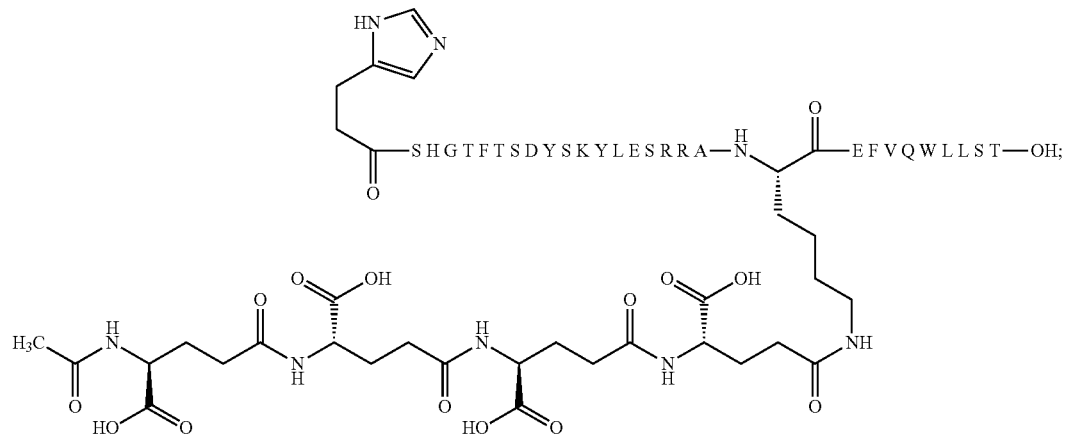
(Chem. 13)
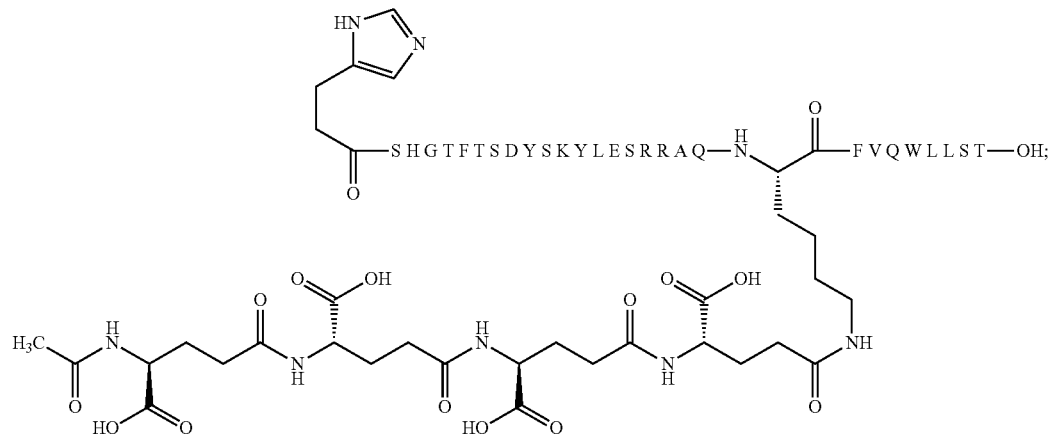
(Chem. 14)
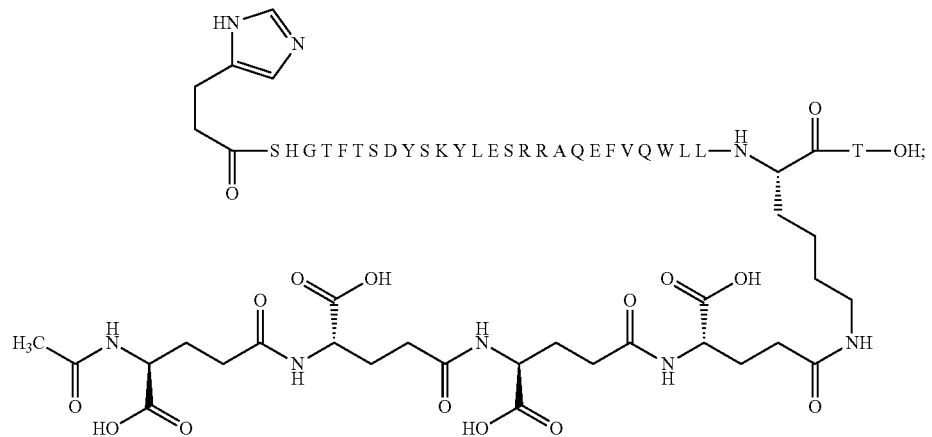

(Chem. 15)
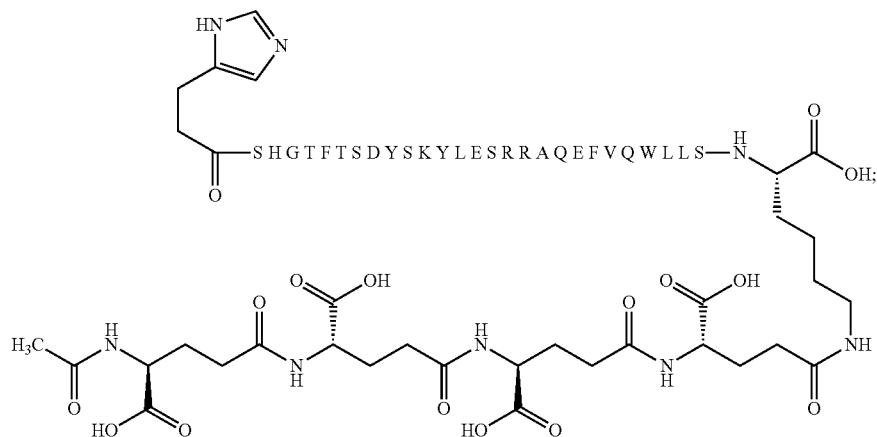
(Chem. 16)
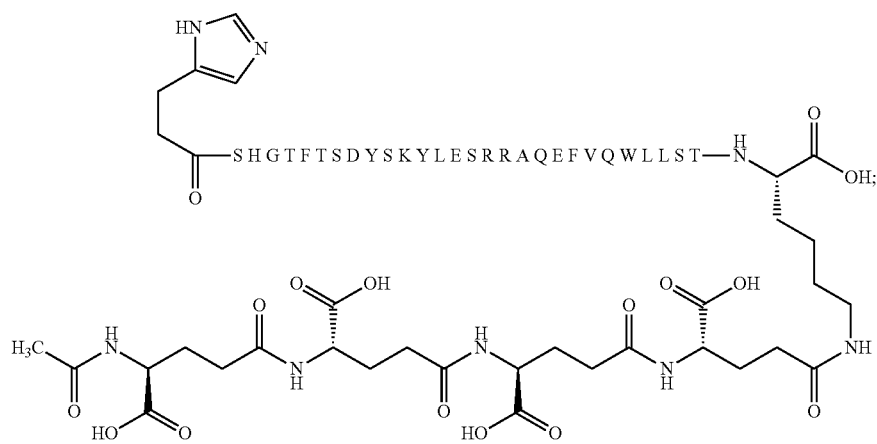
(Chem. 17)
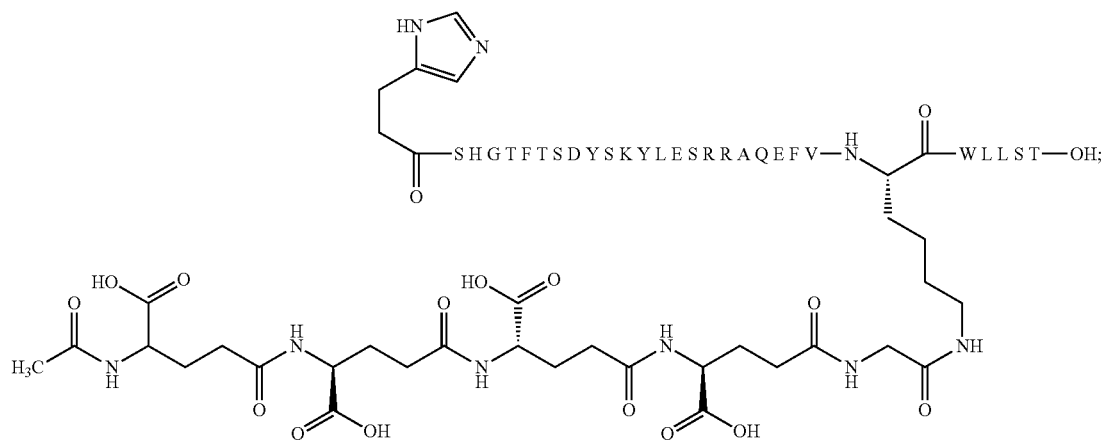

(Chem. 18)
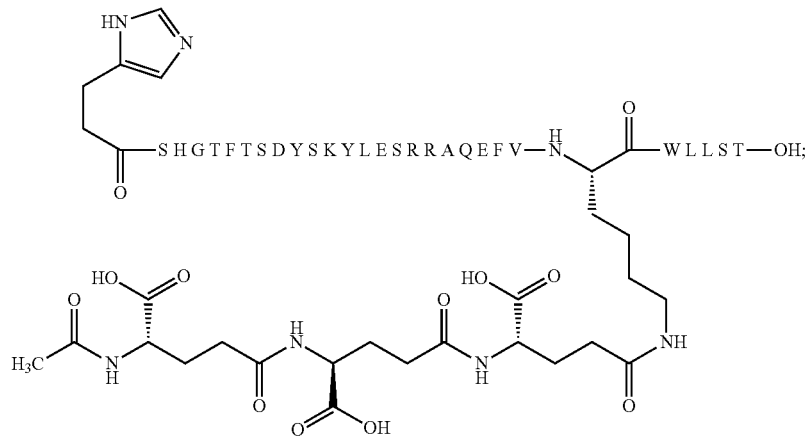
(Chem. 19)
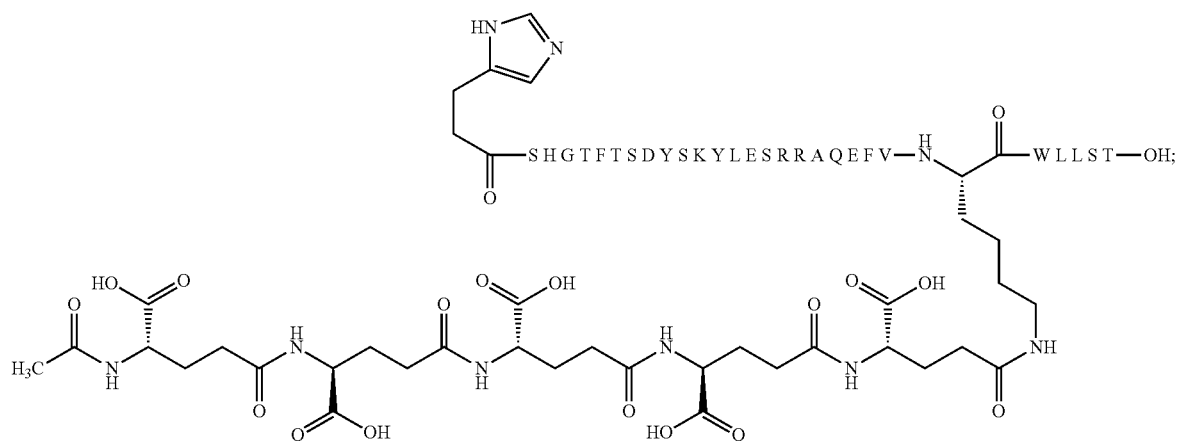
(Chem. 20)
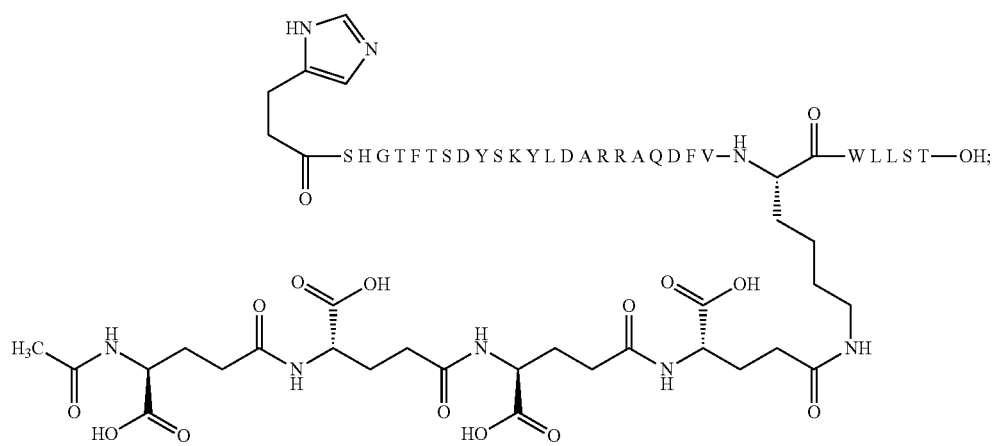

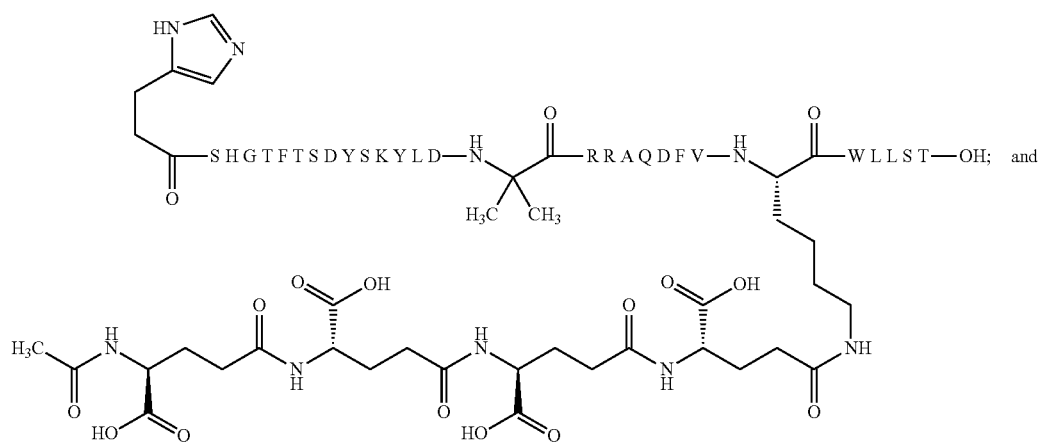

(Chem. 21)

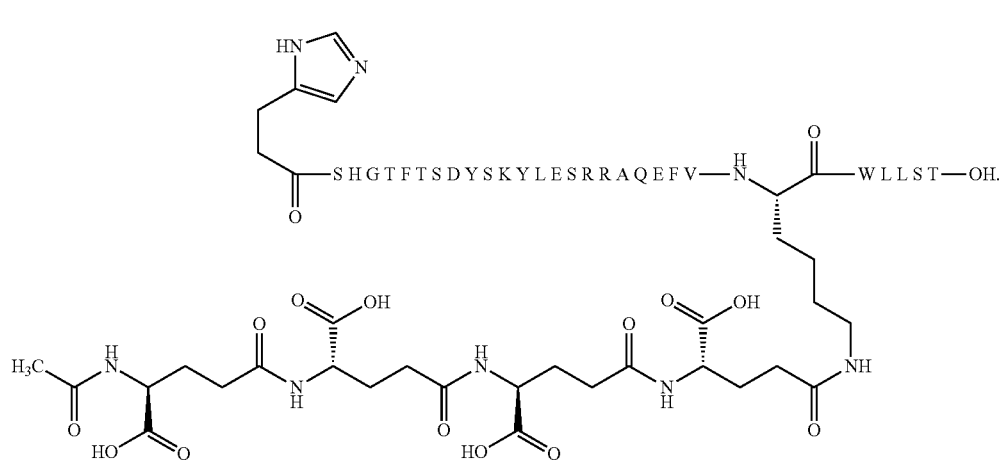

(Chem. 22)

9. A glucagon analogue comprising modifications of SEQ ID NO: 1, wherein the glucagon analogue is selected from the group consisting of
[Imp1, Aib2, His3, Leu16, Lys24, Leu27, Ser28]-Glucagon;
[Imp1, Aib2, His3, Glu15, Lys24, Leu27, Ser28]-Glucagon;
[Imp1, Aib2, His3, Leu10, Glu15, Lys24, Leu27, Ser28]-Glucagon;
[Imp1, Aib2, His3, Glu15, Ala24, Leu27, Lys28]-Glucagon;
[Imp1, His3, Glu15, Lys24, Leu27, Ser28]-Glucagon;
[Imp1, His3, Glu15, Glu21, Lys24, Leu27, Ser28]-Glucagon;
[Imp1, Aib2, His3, Glu15, Glu21, Leu27, Ser28]-Glucagon;
[Imp1, His3, Leu16, Glu21, Lys24, Leu27, Ser28]-Glucagon;
[Imp1, His3, Leu16, Lys24, Leu27, Ser28]-Glucagon;
[Imp1, Aib2, His3, Val16, Lys24, Leu27, Ser28]-Glucagon;
[Imp1, His3, Glu15, Lys16, Glu21, Leu27, Ser28]-Glucagon;
[Imp1, His3, Glu15, Lys20, Glu21, Leu27, Ser28]-Glucagon;
[Imp1, His3, Glu15, Lys21, Leu27, Ser28]-Glucagon;
[Imp1, His3, Glu15, Glu21, Leu27, Lys28]-Glucagon;
[Imp1, His3, Glu15, Glu21, Leu27, Ser28, Lys29]-Glucagon;
[Imp1, His3, Glu15, Glu21, Leu27, Ser28, Lys30]-Glucagon;
[Imp1, His3, Ala16, Lys24, Leu27, Ser28]-Glucagon;
[Imp1, His3, Aib16, Lys24, Leu27, Ser28]-Glucagon; and
[Imp1, His3, Glu15, Glu21, Lys24, Leu27, Glu28]-Glucagon;
or a pharmaceutically acceptable salt, amide, or ester thereof.

10. A pharmaceutical composition comprising the derivative according to claim 1 and one or more pharmaceutically acceptable excipients.

11. The derivative according to claim 8, wherein the derivative is (Chem. 6)
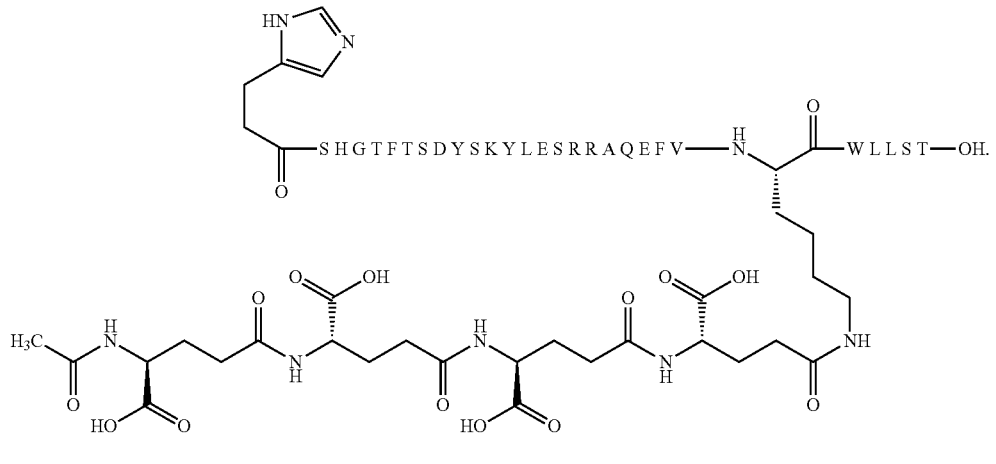
12. The derivative according to claim 8, wherein the derivative is
(Chem. 1)
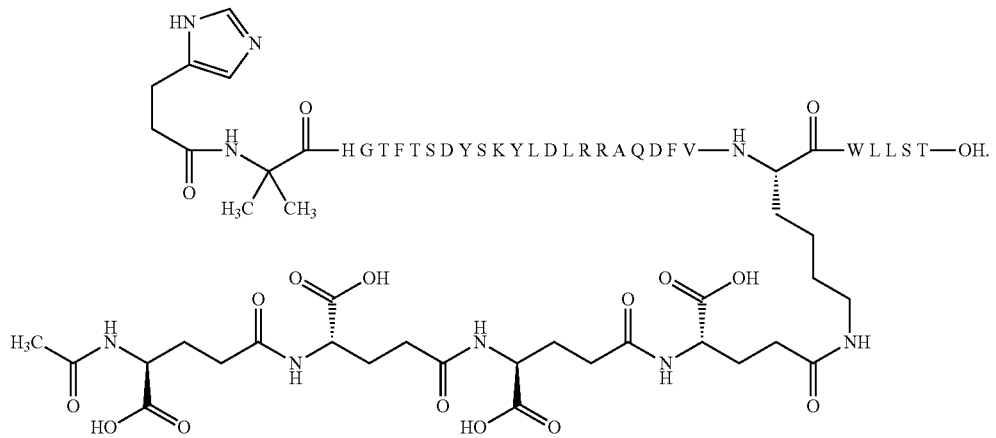
13. The derivative according to claim 8, wherein the derivative is
(Chem. 2)
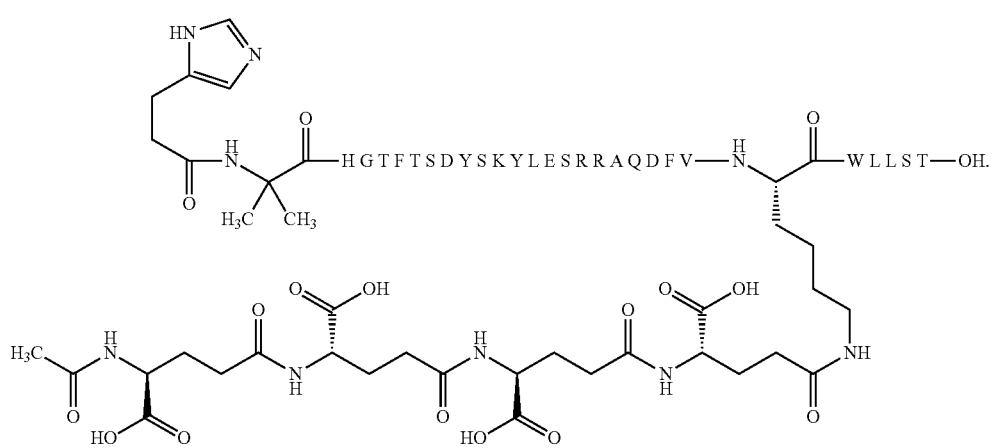

14. The derivative according to claim 8, wherein the derivative is

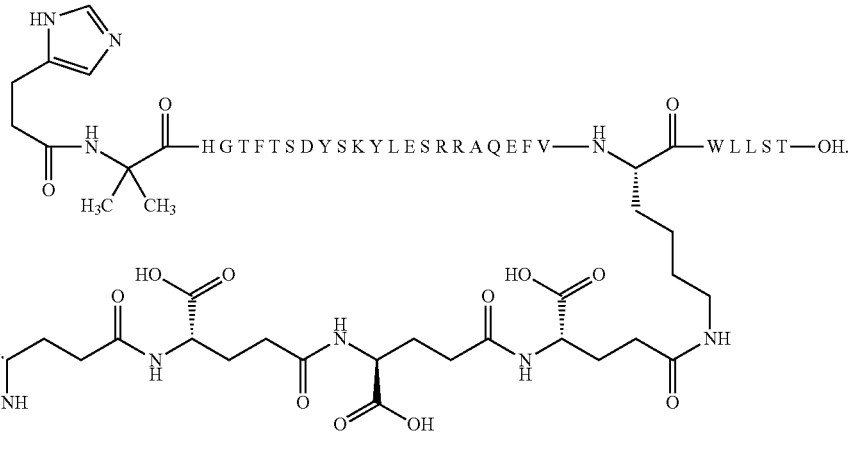

(Chem. 7)

15. The pharmaceutical composition according to claim 10, wherein the peptide is selected from the group consisting of:
  [Imp1, Aib2, His3, Leu16, Lys24, Leu27, Ser28]-Glucagon;
  [Imp1, Aib2, His3, Glu15, Lys24, Leu27, Ser28]-Glucagon;
  [Imp1, Aib2, His3, Leu10, Glu15, Lys24, Leu27, Ser28]-Glucagon;
  [Imp1, Aib2, His3, Glu15, Ala24, Leu27, Lys28]-Glucagon;
  [Imp1, His3, Glu15, Lys24, Leu27, Ser28]-Glucagon;
  [Imp1, His3, Glu15, Glu21, Lys24, Leu27, Ser28]-Glucagon;
  [Imp1, Aib2, His3, Glu15, Glu21, Lys24, Leu27, Ser28]-Glucagon;
  [Imp1, His3, Leu16, Glu21, Lys24, Leu27, Ser28]-Glucagon;
  [Imp1, His3, Leu16, Lys24, Leu27, Ser28]-Glucagon;
  [Imp1, Aib2, His3, Val16, Lys24, Leu27, Ser28]-Glucagon;
  [Imp1, His3, Glu15, Lys16, Glu21, Leu27, Ser28]-Glucagon;
  [Imp1, His3, Glu15, Lys20, Glu21, Leu27, Ser28]-Glucagon;
  [Imp1, His3, Glu15, Lys21, Leu27, Ser28]-Glucagon;
  [Imp1, His3, Glu15, Glu21, Leu27, Lys28]-Glucagon;
  [Imp1, His3, Glu15, Glu21, Leu27, Ser28, Lys29]-Glucagon;
  [Imp1, His3, Glu15, Glu21, Leu27, Ser28, Lys30]-Glucagon;
  [Imp1, His3, Ala16, Lys24, Leu27, Ser28]-Glucagon;
  [Imp1, His3, Aib16, Lys24, Leu27, Ser28]-Glucagon; and
  [Imp1, His3, Glu15, Glu21, Lys24, Leu27, Glu28]-Glucagon;
  or a pharmaceutically acceptable salt, amide, or ester thereof.

16. The pharmaceutical composition according to claim 10, wherein the derivative is

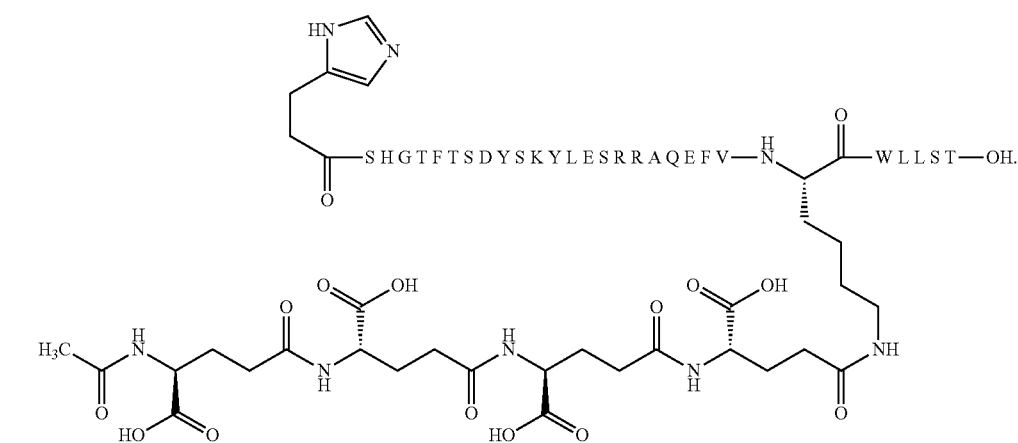

(Chem. 6)

17. The pharmaceutical composition according to claim 10, wherein the derivative is

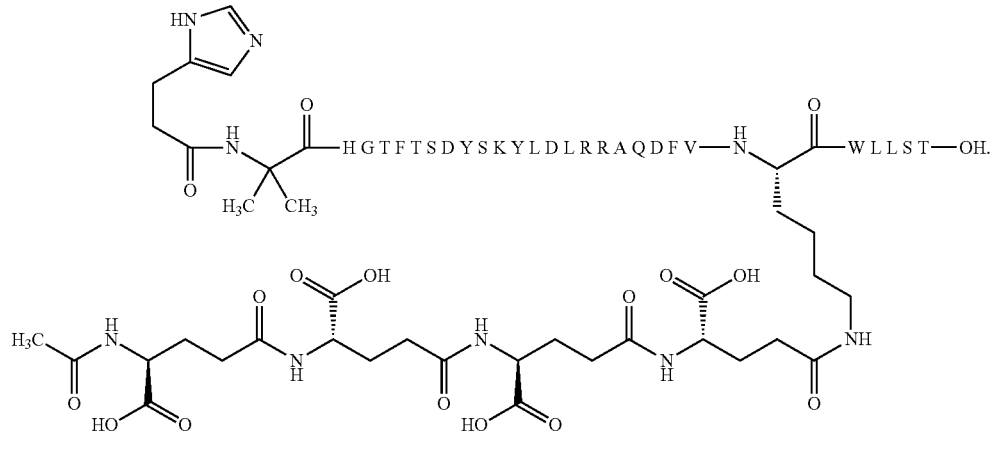
18. The pharmaceutical composition according to claim 10, wherein the derivative is
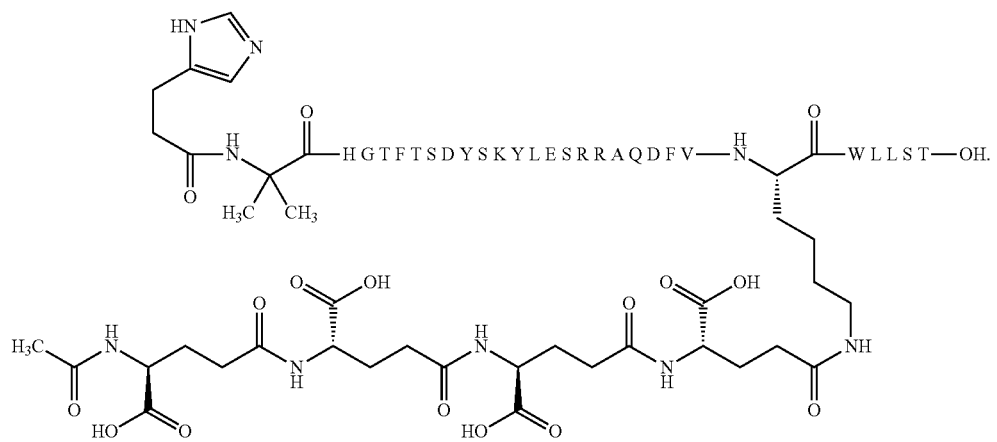
19. The pharmaceutical composition according to claim 10, wherein the derivative is
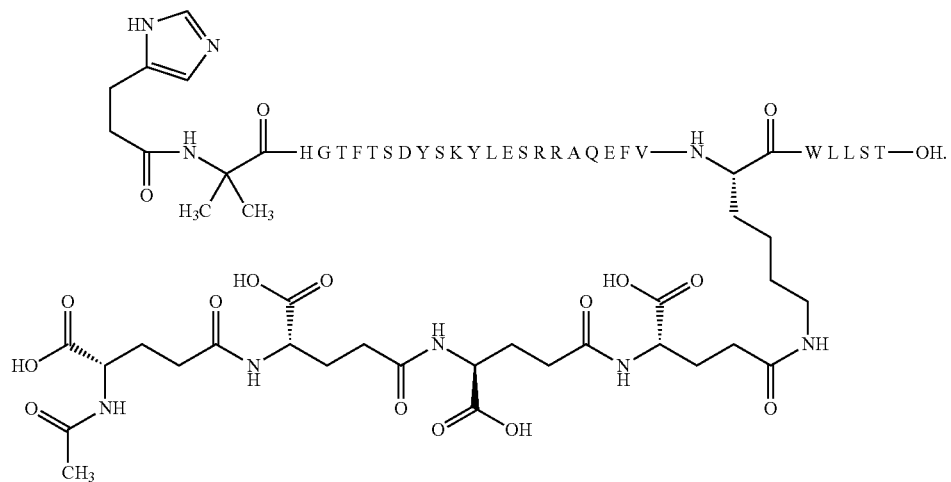

20. A method of treating hypoglycaemia, comprising administering the derivative of claim 1 to a patient in need thereof.

21. The method according to claim 20, wherein the substituent is attached to the lysine in position $X_{24}$.

22. The method according to claim 20, wherein the peptide is selected from the group consisting of:
[Imp1, Aib2, His3, Leu16, Lys24, Leu27, Ser28]-Glucagon;
[Imp1, Aib2, His3, Glu15, Lys24, Leu27, Ser28]-Glucagon;
[Imp1, Aib2, His3, Leu10, Glu15, Lys24, Leu27, Ser28]-Glucagon;
[Imp1, Aib2, His3, Glu15, Ala24, Leu27, Lys28]-Glucagon;
[Imp1, His3, Glu15, Lys24, Leu27, Ser28]-Glucagon;
[Imp1, His3, Glu15, Glu21, Lys24, Leu27, Ser28]-Glucagon;
[Imp1, Aib2, His3, Glu15, Glu21, Lys24, Leu27, Ser28]-Glucagon;
[Imp1, His3, Leu16, Glu21, Lys24, Leu27, Ser28]-Glucagon;
[Imp1, His3, Leu16, Lys24, Leu27, Ser28]-Glucagon;
[Imp1, Aib2, His3, Val16, Lys24, Leu27, Ser28]-Glucagon;
[Imp1, His3, Glu15, Lys16, Glu21, Leu27, Ser28]-Glucagon;
[Imp1, His3, Glu15, Lys20, Glu21, Leu27, Ser28]-Glucagon;
[Imp1, His3, Glu15, Lys21, Leu27, Ser28]-Glucagon;
[Imp1, His3, Glu15, Glu21, Leu27, Lys28]-Glucagon;
[Imp1, His3, Glu15, Glu21, Leu27, Ser28, Lys29]-Glucagon;
[Imp1, His3, Glu15, Glu21, Leu27, Ser28, Lys30]-Glucagon;
[Imp1, His3, Ala16, Lys24, Leu27, Ser28]-Glucagon;
[Imp1, His3, Aib16, Lys24, Leu27, Ser28]-Glucagon; and
[Imp1, His3, Glu15, Glu21, Lys24, Leu27, Glu28]-Glucagon;
or a pharmaceutically acceptable salt, amide, or ester thereof.

23. The method according to claim 20, wherein the derivative is

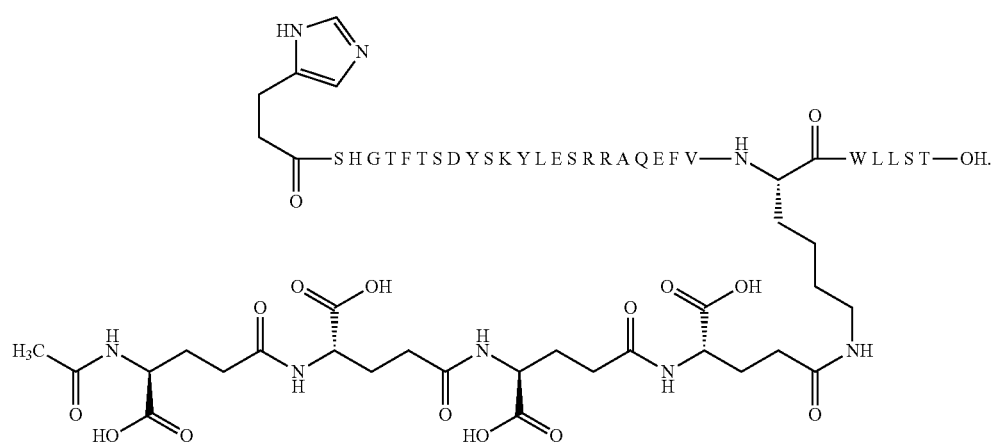

(Chem. 6)

24. The method according to claim 20, wherein the derivative is

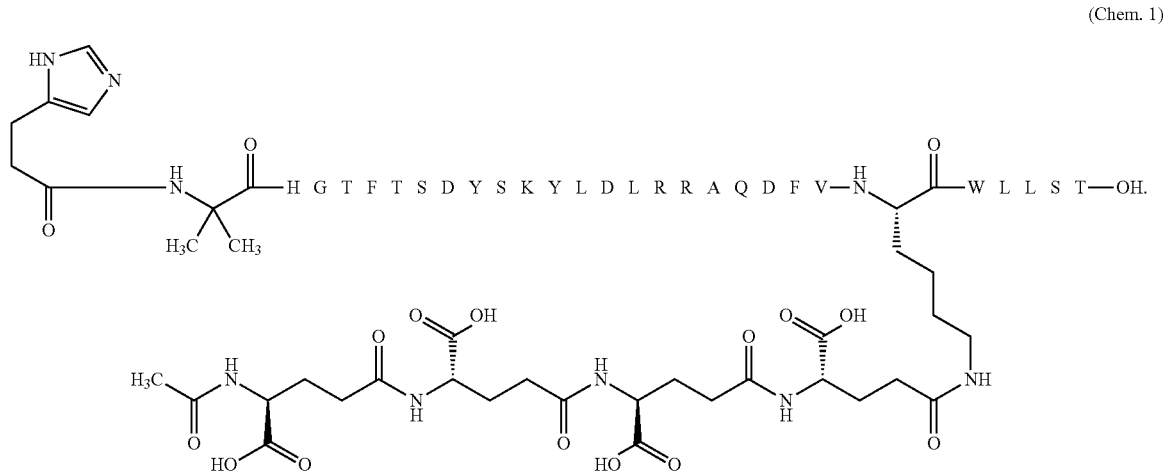

(Chem. 1)

25. The method according to claim 20, wherein the derivative is
(Chem. 2)
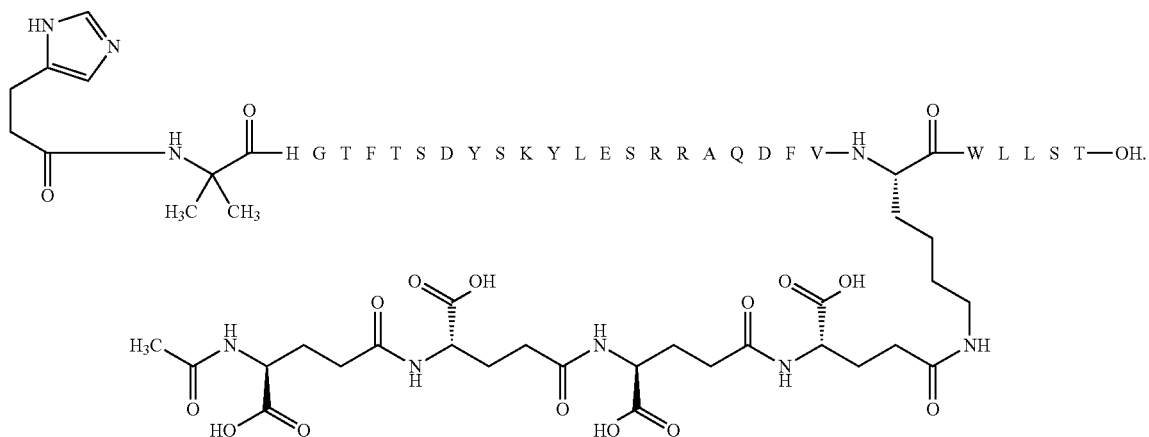
26. The method according to claim 20, wherein the derivative is
(Chem. 7)
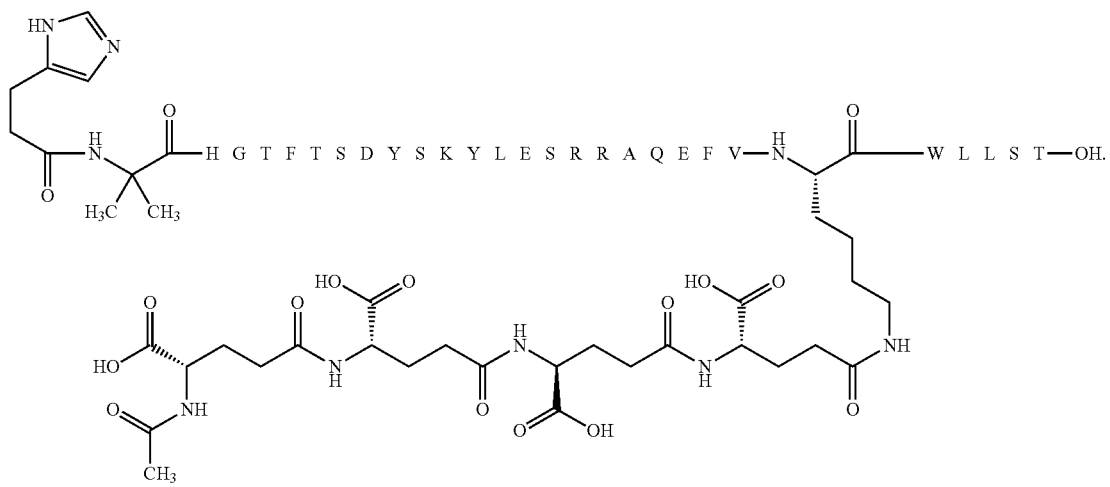
* * * * *

```
                        SEQUENCE LISTING

<160> NUMBER OF SEQ ID NOS: 21

<210> SEQ ID NO 1
<211> LENGTH: 29
<212> TYPE: PRT
<213> ORGANISM: HOMO SAPIENS

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)
<220> FEATURE:
<221> NAME/KEY: MISC_FEATURE
<222> LOCATION: (2)..(2)
<223> OTHER INFORMATION: Xaa = alpha-aminoisobutyric acid (Aib)

<400> SEQUENCE: 2

Xaa Xaa His Gly Thr Phe Thr Ser Asp Tyr Ser Lys Tyr Leu Asp Leu
1               5                   10                  15

Arg Arg Ala Gln Asp Phe Val Lys Trp Leu Leu Ser Thr
            20                  25

<210> SEQ ID NO 3
<211> LENGTH: 29
<212> TYPE: PRT
<213> ORGANISM: ARTIFICIAL
<220> FEATURE:
```

<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)
<220> FEATURE:
<221> NAME/KEY: MISC_FEATURE
<222> LOCATION: (2)..(2)
<223> OTHER INFORMATION: Xaa = alpha-aminoisobutyric acid (Aib)

<400> SEQUENCE: 3

Xaa Xaa His Gly Thr Phe Thr Ser Asp Tyr Ser Lys Tyr Leu Glu Ser
1               5                   10                  15

Arg Arg Ala Gln Asp Phe Val Lys Trp Leu Leu Ser Thr
            20                  25

<210> SEQ ID NO 4
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)
<220> FEATURE:
<221> NAME/KEY: MISC_FEATURE
<222> LOCATION: (2)..(2)
<223> OTHER INFORMATION: Xaa = alpha-aminoisobutyric acid (Aib)

<400> SEQUENCE: 4

Xaa Xaa His Gly Thr Phe Thr Ser Asp Leu Ser Lys Tyr Leu Glu Ser
1               5                   10                  15

Arg Arg Ala Gln Asp Phe Val Lys Trp Leu Leu Ser Thr
            20                  25

<210> SEQ ID NO 5
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)
<220> FEATURE:
<221> NAME/KEY: MISC_FEATURE
<222> LOCATION: (2)..(2)
<223> OTHER INFORMATION: Xaa = alpha-aminoisobutyric acid (Aib)

<400> SEQUENCE: 5

Xaa Xaa His Gly Thr Phe Thr Ser Asp Tyr Ser Lys Tyr Leu Glu Ser
1               5                   10                  15

Arg Arg Ala Gln Asp Phe Val Ala Trp Leu Leu Lys Thr
            20                  25

<210> SEQ ID NO 6
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 6

```
Xaa Ser His Gly Thr Phe Thr Ser Asp Tyr Ser Lys Tyr Leu Glu Ser
1               5                   10                  15

Arg Arg Ala Gln Asp Phe Val Lys Trp Leu Leu Ser Thr
            20                  25

<210> SEQ ID NO 7
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 7

Xaa Ser His Gly Thr Phe Thr Ser Asp Tyr Ser Lys Tyr Leu Glu Ser
1               5                   10                  15

Arg Arg Ala Gln Glu Phe Val Lys Trp Leu Leu Ser Thr
            20                  25

<210> SEQ ID NO 8
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)
<220> FEATURE:
<221> NAME/KEY: MISC_FEATURE
<222> LOCATION: (2)..(2)
<223> OTHER INFORMATION: Xaa = alpha-aminoisobutyric acid (Aib)

<400> SEQUENCE: 8

Xaa Xaa His Gly Thr Phe Thr Ser Asp Tyr Ser Lys Tyr Leu Glu Ser
1               5                   10                  15

Arg Arg Ala Gln Glu Phe Val Lys Trp Leu Leu Ser Thr
            20                  25

<210> SEQ ID NO 9
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 9

Xaa Ser His Gly Thr Phe Thr Ser Asp Tyr Ser Lys Tyr Leu Asp Leu
1               5                   10                  15

Arg Arg Ala Gln Glu Phe Val Lys Trp Leu Leu Ser Thr
            20                  25

<210> SEQ ID NO 10
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
```

```
<221> NAME/KEY: MISC_FEATURE
<222> LOCATION: (1)..(1)
<223> OTHER INFORMATION: Xaa = imidazopropionyl (Imp)

<400> SEQUENCE: 10

Xaa Ser His Gly Thr Phe Thr Ser Asp Tyr Ser Lys Tyr Leu Asp Leu
1               5                   10                  15

Arg Arg Ala Gln Asp Phe Val Lys Trp Leu Leu Ser Thr
            20                  25

<210> SEQ ID NO 11
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)
<220> FEATURE:
<221> NAME/KEY: MISC_FEATURE
<222> LOCATION: (2)..(2)
<223> OTHER INFORMATION: Xaa = alpha-aminoisobutyric acid (Aib)

<400> SEQUENCE: 11

Xaa Xaa His Gly Thr Phe Thr Ser Asp Tyr Ser Lys Tyr Leu Asp Val
1               5                   10                  15

Arg Arg Ala Gln Asp Phe Val Lys Trp Leu Leu Ser Thr
            20                  25

<210> SEQ ID NO 12
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 12

Xaa Ser His Gly Thr Phe Thr Ser Asp Tyr Ser Lys Tyr Leu Glu Lys
1               5                   10                  15

Arg Arg Ala Gln Glu Phe Val Gln Trp Leu Leu Ser Thr
            20                  25

<210> SEQ ID NO 13
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 13

Xaa Ser His Gly Thr Phe Thr Ser Asp Tyr Ser Lys Tyr Leu Glu Ser
1               5                   10                  15

Arg Arg Ala Lys Glu Phe Val Gln Trp Leu Leu Ser Thr
            20                  25

<210> SEQ ID NO 14
<211> LENGTH: 29
```

```
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 14

Xaa Ser His Gly Thr Phe Thr Ser Asp Tyr Ser Lys Tyr Leu Glu Ser
1               5                   10                  15

Arg Arg Ala Gln Lys Phe Val Gln Trp Leu Leu Ser Thr
            20                  25

<210> SEQ ID NO 15
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 15

Xaa Ser His Gly Thr Phe Thr Ser Asp Tyr Ser Lys Tyr Leu Glu Ser
1               5                   10                  15

Arg Arg Ala Gln Glu Phe Val Gln Trp Leu Leu Lys Thr
            20                  25

<210> SEQ ID NO 16
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 16

Xaa Ser His Gly Thr Phe Thr Ser Asp Tyr Ser Lys Tyr Leu Glu Ser
1               5                   10                  15

Arg Arg Ala Gln Glu Phe Val Gln Trp Leu Leu Ser Lys
            20                  25

<210> SEQ ID NO 17
<211> LENGTH: 30
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 17

Xaa Ser His Gly Thr Phe Thr Ser Asp Tyr Ser Lys Tyr Leu Glu Ser
1               5                   10                  15

Arg Arg Ala Gln Glu Phe Val Gln Trp Leu Leu Ser Thr Lys
            20                  25                  30

<210> SEQ ID NO 18
```

```
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 18

Xaa Ser His Gly Thr Phe Thr Ser Asp Tyr Ser Lys Tyr Leu Asp Ala
1               5                   10                  15

Arg Arg Ala Gln Asp Phe Val Lys Trp Leu Leu Ser Thr
            20                  25

<210> SEQ ID NO 19
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)
<220> FEATURE:
<221> NAME/KEY: MISC_FEATURE
<222> LOCATION: (16)..(16)

<400> SEQUENCE: 19

Xaa Ser His Gly Thr Phe Thr Ser Asp Tyr Ser Lys Tyr Leu Asp Xaa
1               5                   10                  15

Arg Arg Ala Gln Asp Phe Val Lys Trp Leu Leu Ser Thr
            20                  25

<210> SEQ ID NO 20
<211> LENGTH: 29
<212> TYPE: PRT
<213> ORGANISM: ARTIFICIAL
<220> FEATURE:
<223> OTHER INFORMATION: Artificial protein based on human glucagon
<220> FEATURE:
<221> NAME/KEY: MISC_FEATURE
<222> LOCATION: (1)..(1)
<223> OTHER INFORMATION: Xaa = imidazopropionyl (Imp)

<400> SEQUENCE: 20

Xaa Ser His Gly Thr Phe Thr Ser Asp Tyr Ser Lys Tyr Leu Glu Ser
1               5                   10                  15

Arg Arg Ala Gln Glu Phe Val Lys Trp Leu Leu Glu Thr
            20                  25

<210> SEQ ID NO 21
<211> LENGTH: 30
<212> TYPE: PRT
<213> ORGANISM: ARTIFICIAL
<220> FEATURE:
<223> OTHER INFORMATION: Artificial sequence based on human glucagon
<220> FEATURE:
<221> NAME/KEY: MISC_FEATURE
<222> LOCATION: (1)..(1)
<223> OTHER INFORMATION: Xaa = Imp (desaminohistidine)
<220> FEATURE:
<221> NAME/KEY: MISC_FEATURE
<222> LOCATION: (2)..(2)
<223> OTHER INFORMATION: Xaa = Ser or Aib
<220> FEATURE:
<221> NAME/KEY: MISC_FEATURE
<222> LOCATION: (10)..(10)
```

```
<223> OTHER INFORMATION: Xaa = Tyr, Leu, Ile or Val
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (15)..(15)
<223> OTHER INFORMATION: Xaa = Asp or Glu
<220> FEATURE:
<221> NAME/KEY: MISC_FEATURE
<222> LOCATION: (16)..(16)
<223> OTHER INFORMATION: Xaa = Ser, Ala, Leu, Thr, Aib, Ile, Val or Lys
<220> FEATURE:
<221> NAME/KEY: MISC_FEATURE
<222> LOCATION: (20)..(20)
<223> OTHER INFORMATION: Xaa = Gln, Glu, Aib or Lys
<220> FEATURE:
<221> NAME/KEY: MISC_FEATURE
<222> LOCATION: (21)..(21)
<223> OTHER INFORMATION: Xaa = Asp, Glu or Lys
<220> FEATURE:
<221> NAME/KEY: MISC_FEATURE
<222> LOCATION: (24)..(24)
<223> OTHER INFORMATION: Xaa = Gln, Ala, Glu, Aib or Lys
<220> FEATURE:
<221> NAME/KEY: MISC_FEATURE
<222> LOCATION: (27)..(27)
<223> OTHER INFORMATION: Xaa = Met, Leu or Val
<220> FEATURE:
<221> NAME/KEY: MISC_FEATURE
<222> LOCATION: (28)..(28)
<223> OTHER INFORMATION: Xaa = Asn, Ser, Thr, Gln, Ala, Gly, Glu or Lys
<220> FEATURE:
<221> NAME/KEY: MISC_FEATURE
<222> LOCATION: (29)..(29)
<223> OTHER INFORMATION: Xaa = Thr, Gly, Ser, Gln, Ala, Glu or Lys
<220> FEATURE:
<221> NAME/KEY: MISC_FEATURE
<222> LOCATION: (30)..(30)
<223> OTHER INFORMATION: Xaa = absent or is Lys

<400> SEQUENCE: 21

Xaa Xaa His Gly Thr Phe Thr Ser Asp Xaa Ser Xaa Tyr Leu Xaa Xaa
1               5                   10                  15

Arg Arg Ala Xaa Xaa Phe Val Xaa Trp Leu Xaa Xaa Xaa Xaa
            20                  25                  30
```